US012601743B2

(12) United States Patent
Cheresh et al.

(10) Patent No.: US 12,601,743 B2
(45) Date of Patent: Apr. 14, 2026

(54) METHODS FOR TREATING DRUG RESISTANT CANCERS

(71) Applicant: The Regents of the University of California, Oakland, CA (US)

(72) Inventors: David Cheresh, Encinitas, CA (US); Sara Weis, San Diego, CA (US); Erika Cosset, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 193 days.

(21) Appl. No.: 18/195,184

(22) Filed: May 9, 2023

(65) Prior Publication Data

US 2023/0417764 A1     Dec. 28, 2023

Related U.S. Application Data

(63) Continuation of application No. 16/622,796, filed as application No. PCT/US2018/037595 on Jun. 14, 2018, now abandoned.

(60) Provisional application No. 62/519,734, filed on Jun. 14, 2017.

(51) Int. Cl.
| | |
|---|---|
| *G01N 33/574* | (2006.01) |
| *A61K 38/12* | (2006.01) |
| *C07K 14/705* | (2006.01) |
| *C07K 16/28* | (2006.01) |
| *C07K 16/30* | (2006.01) |
| *G01N 33/68* | (2006.01) |

(52) U.S. Cl.
CPC ......... *G01N 33/6872* (2013.01); *A61K 38/12* (2013.01); *C07K 14/70546* (2013.01); *C07K 14/70557* (2013.01); *C07K 16/2848* (2013.01); *C07K 16/2863* (2013.01); *C07K 16/30* (2013.01); *G01N 33/574* (2013.01); *G01N 33/57492* (2013.01); *C07K 2317/569* (2013.01); *C07K 2317/622* (2013.01); *G01N 2333/70557* (2013.01)

(58) Field of Classification Search
CPC ............................ C07K 16/2863; C07K 16/28; C07K 16/2848; C07K 16/30; C07K 2317/569; C07K 2317/622; C07K 14/70557; C07K 14/705; C07K 14/70546; G01N 33/68; G01N 33/574; G01N 33/57492; G01N 33/6872
See application file for complete search history.

(56) References Cited

U.S. PATENT DOCUMENTS

| | | |
|---|---|---|
| 2006/0003363 A1 | 1/2006 | Zerangue |
| 2006/0172305 A1 | 8/2006 | Tidmarsh |
| 2014/0073523 A1 | 3/2014 | Onodera et al. |

FOREIGN PATENT DOCUMENTS

WO     2012167028 A2     12/2012

OTHER PUBLICATIONS

Cosset et al., "Glut3 addiction is a druggable vulnerability for a molecularly defined subpopulation of glioblastoma" ancer Cell, 2017, v 32, n 6, p. 856-868.
Stoica et al., "Identification of cancer stem cells in dog glioblastoma" Vet Pathol., 2009, v 46, n 3, p. 391-406.
Franovic et al., "Glioblastoma require integrin alpha.v.beta.3/PAK4 signaling to escape senescence" Cancer Res., 2015, v 75, n 21, p. 4466-4473.
Flavahan et al., "Brain tumor initiating cells adapt to restricted nutrition through preferential glucose uptake" Nat. Neurosci., 2013, v 16, n 10, p. 1373-1382.
"Essentials of Cell Biology; Unit 2: How do Cells Decode Genetic Information into Functional Proteins?", a Nature ebook, https://www.nature.com/scitable/ebooks/essnetial-of-cell-biology-147 49010/122996756 (8 total pages); accessed Jun. 17, 2022.
Gladson, C. Expression of integrin avb3 in small blood vessels of glioblastoma tumors. J Neuropathol Exp Neural 55(11): 1143-1149, 1996.
Paik et al. Ongoing angiogenesis in blood vessels of the abdominal aortic aneurysm. Exp Mol Med 36(6): 524-533, 2004.
Roth et al. Integrin control of the transforming growth factor-pathway in glioblastoma. Brain 136(2): 564-576, 2013.
Son et al. Multiple FAS1 domains and the RGD motif of TGFBI act cooperatively to bind avb3 integrin, leading to anti-angiogenic and anti-tumor effects. Biochim Biophys Acta 1833: 2378-2388, 2013.
Zhang et al. Can an 18F-ALF-NOTA-PRGD2 PET/CT scan predict treatment sensitivity to concurrent chemoradiotherapy in patients with newly diagnosed glioblastoma? J Nucl Med 57: 524-529, 2016.

*Primary Examiner* — Bridget E Bunner
(74) *Attorney, Agent, or Firm* — Gregory P. Einhorn; Greer, Burns & Crain, Ltd.

(57) ABSTRACT

Provided are methods for determining whether a glioblastoma (GBM) tumor or GBM cancer cell will be sensitive to a treatment targeting the integrin avb3 ($\alpha v\beta 3$) pathway, comprising determining whether the GBM tumor or the GBM cancer cell expresses both avb3+ and Glut3+ along with a specific genetic signature associated with Glut3 addiction, where in alternative embodiments a cell is Glut3 addiction if the GBM tumor or the GBM cancer cell has markers consistent with the Classical or the Proneural molecular subtypes of GBM, or, expresses markers consistent with a Glut3-addicted molecular signature, e.g., as listed in FIG. 11 or FIG. 23. Also provided herein are methods of treating glioblastoma (GBM) tumors found to be sensitive to agents targeting or inhibiting the integrin avb3 ($\alpha v\beta 3$) pathway, wherein the sensitivity is determined by methods as provided herein.

9 Claims, 69 Drawing Sheets
(61 of 69 Drawing Sheet(s) Filed in Color)
Specification includes a Sequence Listing.

*ITGB3* (β3)

immune system process
metabolic process                    *
multicellular organismal process
developmental process
response to stimulus
biological regulation
localization
cellular process                     *
cellular organization/biogenesis Percentage of Enrichment

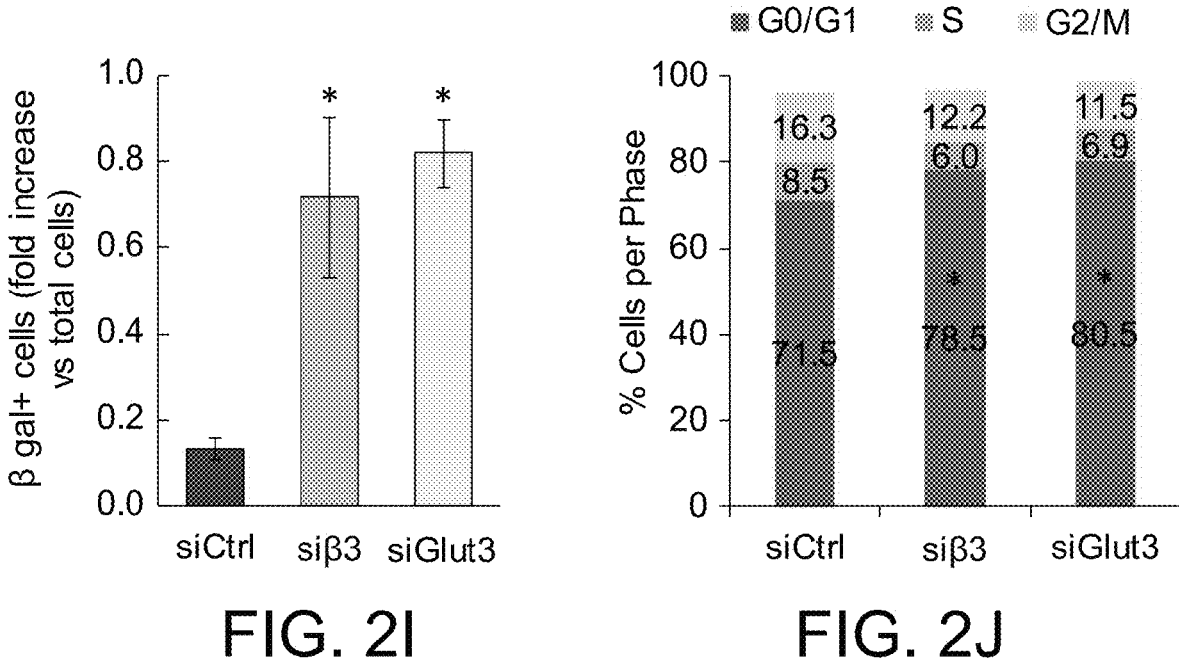
FIG. 2I
FIG. 2J
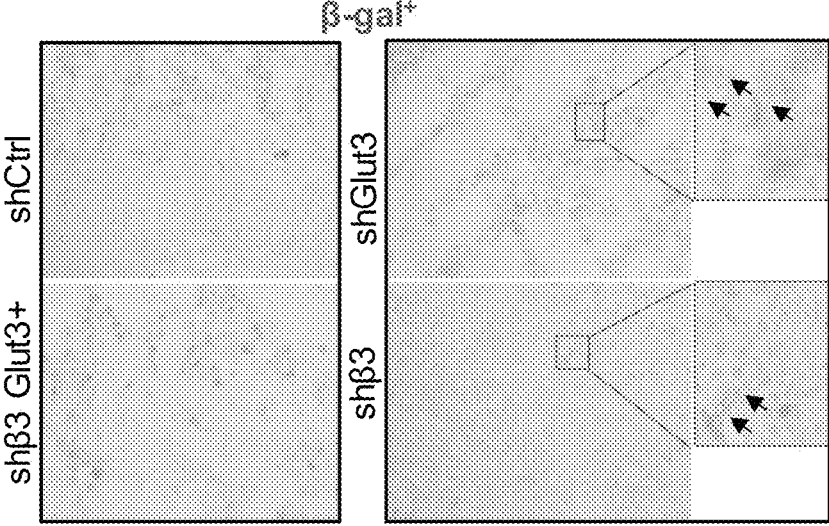
FIG. 2K

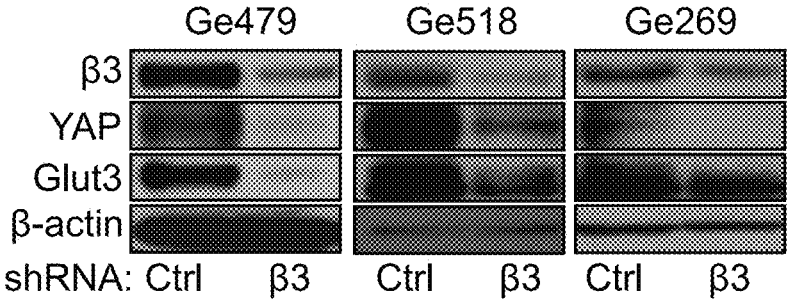
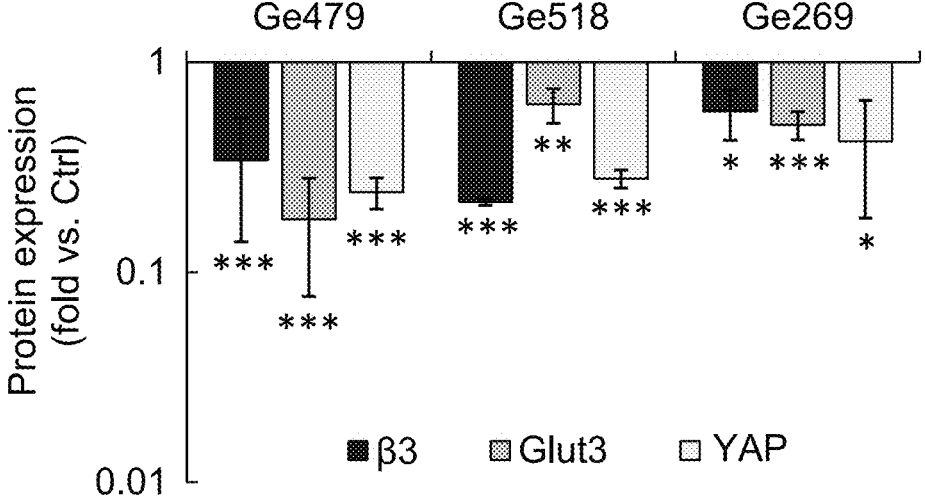
FIG. 4B

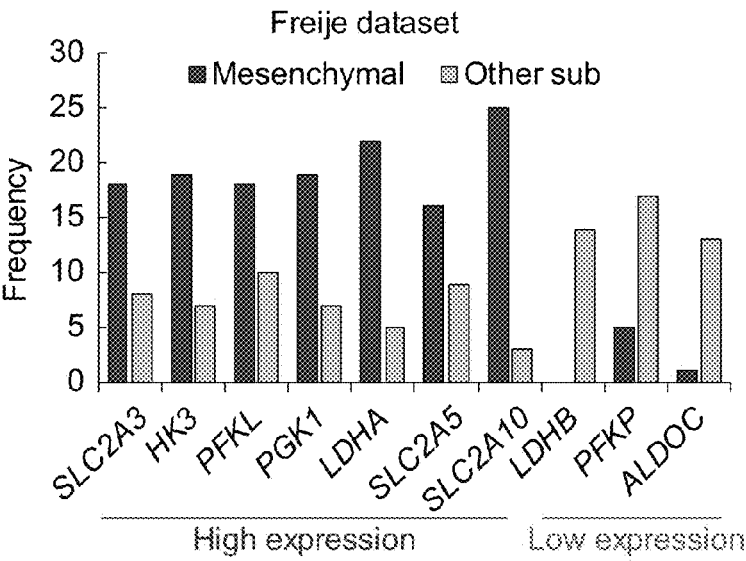
FIG. 5A
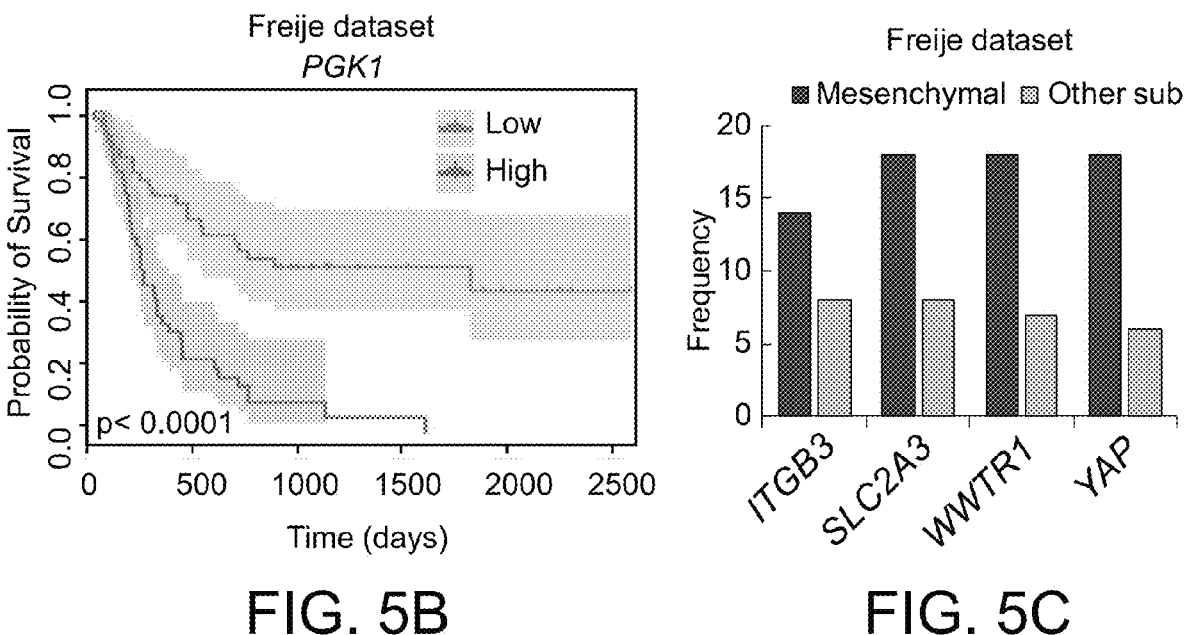
FIG. 5B                    FIG. 5C

| Name | pValue | | |
|------|--------|-----|-------|
|      | Freije | Lee | TCGA* |
| ITGB1 | 0.48 | 0.11 | < 0.001 |
| ITGB2 | 0.59 | 0.54 | 0.51 |
| ITGB3 | 0.03 | 0.01 | 0.008 |
| ITGB4 | 0.06 | 0.13 | 0.58 |
| ITGB5 | 0.61 | 0.05 | 0.36 |
| ITGB6 | 0.15 | 0.13 | 0.99 |
| ITGB7 | 0.84 | 0.84 | 0.004 |
| ITGB8 | 0.62 | 0.86 | < 0.001 |

* TCGA GBM-LGG dataset

FIG. 7

Phillips dataset

| Rank | Gene names | Rank | Gene names | Rank | Gene names | Rank | Gene names |
|---|---|---|---|---|---|---|---|
| 1 | GPR176 | 31 | RPS14 | 61 | MMP14 | 91 | SLC11A2 |
| 2 | PI4K2A | 32 | MLPH | 62 | BACE2 | 92 | SLC2A5 |
| 3 | TRAF6 | 33 | TNFRSF9 | 63 | PHLDA1 | 93 | ELK3 |
| 4 | CCR2 | 34 | MYD88 | 64 | THAP7 | 94 | ELAVL3 |
| 5 | ZC3H12A | 35 | NOD2 | 65 | RAB38 | 95 | CDRT1 |
| 6 | SLC2A3 | 36 | COPS8 | 66 | APOL6 | 96 | FCGR2C |
| 7 | ICAM1 | 37 | RNASE3 | 67 | DOCK5 | 97 | CACYBP |
| 8 | STK10 | 38 | CASP5 | 68 | LONRF3 | 98 | MYOF |
| 9 | IL1B | 39 | ABL2 | 69 | PDCD1LG2 | 99 | FAM98A |
| 10 | ADAM17 | 40 | CYP1A2 | 70 | CHST4 | 100 | ELOVL5 |
| 11 | IL15RA | 41 | NRP2 | 71 | IL1B | 101 | COL8A1 |
| 12 | NFKB1 | 42 | ICAM1 | 72 | STK10 | 102 | IL1RN |
| 13 | FPR2 | 43 | ACPP | 73 | WWTR1 | 103 | LPXN |
| 14 | BCL6 | 44 | MTCP1 | 74 | NEDD9 | 104 | CCL13 |
| 15 | SLC39A8 | 45 | NPAS2 | 75 | SPINT1 | 105 | TP53I11 |
| 16 | NRP2 | 46 | STRN | 76 | MMP7 | 106 | AKTIP |
| 17 | TLR8 | 47 | SLC22A18AS | 77 | CCR4 | 107 | MCTP2 |
| 18 | LEF1 | 48 | HSD3B2 | 78 | NRP2 | 108 | RBM19 |
| 19 | CDK5RAP1 | 49 | ITGA2B | 79 | GALNT4 | 109 | STAT2 |
| 20 | CYP2B6 | 50 | PLA2G10 | 80 | ENG | 110 | VDAC3 |
| 21 | DEFB4A | 51 | RAC2 | 81 | SNORA70 | 111 | PGLYRP4 |
| 22 | CYP2B7P | 52 | SLCO4C1 | 82 | TNFRSF11A | 112 | MME |
| 23 | CSF1 | 53 | SCGB1D1 | 83 | SMG6 | 113 | HOXB3 |
| 24 | TTC21B | 54 | CALM1 | 84 | SIGLEC9 | 114 | CYLD |
| 25 | ADAM12 | 55 | CHST3 | 85 | CALM1 | 115 | SGPL1 |
| 26 | ADAM12 | 56 | MPZL1 | 86 | OSMR | 116 | SLC43A3 |
| 27 | IL13RA1 | 57 | HPS1 | 87 | PML | 117 | DAB2 |
| 28 | PHLDA1 | 58 | SEL1L3 | 88 | SAMD4A | 118 | ITGB1 |
| 29 | CD44 | 59 | DCBLD2 | 89 | DST | 119 | CYP2A7P1 |
| 30 | APAF1 | 60 | HIST1H3E | 90 | PCDHB8 | 120 | BAK1 |

FIG. 8A

Sun dataset

| Rank | Gene names | Rank | Gene names | Rank | Gene names | Rank | Gene names |
|---|---|---|---|---|---|---|---|
| 1 | ITGB3 | 31 | GNAQ | 61 | CHRNA9 | 91 | CD44 |
| 2 | RAB27A | 32 | STOX2 | 62 | ACSS1 | 92 | LOXL2 |
| 3 | THBS1 | 33 | CSMD1 | 63 | MTA3 | 93 | EMP1 |
| 4 | ATP13A3 | 34 | STOX2 | 64 | SYT16 | 94 | FBLIM1 |
| 5 | ELK3 | 35 | SH3BP2 | 65 | RAB27A | 95 | TRAM2 |
| 6 | USP32 | 36 | IQGAP1 | 66 | LYRM7 | 96 | IRF1 |
| 7 | ZBTB47 | 37 | FCGR2C | 67 | FCGR2C | 97 | PGK1 |
| 8 | CD44 | 38 | FNDC3B | 68 | SLC2A3 | 98 | USP32 |
| 9 | PRSS23 | 39 | TOM1L2 | 69 | GRIA3 | 99 | PATL1 |
| 10 | SERPINE1 | 40 | PPP2R1B | 70 | NAMPT | 100 | SRD5A1 |
| 11 | ITGB3 | 41 | TUBB6 | 71 | WDFY3-AS2 | 101 | WDR17 |
| 12 | CA12 | 42 | IDE | 72 | RABGAP1L | 102 | CD44 |
| 13 | CD44 | 43 | ITPRIPL2 | 73 | TSPAN4 | 103 | NRP2 |
| 14 | CD44 | 44 | PXN-AS1 | 74 | TPM4 | 104 | PGK1 |
| 15 | RBM47 | 45 | USP32P2 | 75 | CLEC2B | 105 | SMURF1 |
| 16 | LPP | 46 | ESYT2 | 76 | MALT1 | 106 | MAGI2 |
| 17 | PPP1R3B | 47 | THBS1 | 77 | SP1 | 107 | SLC9A6 |
| 18 | CD44 | 48 | SHC1 | 78 | RAB32 | 108 | S100A11P1 |
| 19 | EPM2A | 49 | IQGAP1 | 79 | CFLAR | 109 | CACYBP |
| 20 | NRP2 | 50 | PGK1 | 80 | CADM2 | 110 | MVP |
| 21 | MAPT | 51 | IL13RA1 | 81 | CEP97 | 111 | SRPX2 |
| 22 | RALGPS1 | 52 | ITPRIP | 82 | TAF9B | 112 | CYP46A1 |
| 23 | ITGB3 | 53 | CLASP2 | 83 | STOX2 | 113 | FNDC3B |
| 24 | CD44 | 54 | MATR3 | 84 | ACACA | 114 | OSMR |
| 25 | IL13RA1 | 55 | CADM2 | 85 | MACC1 | 115 | LOXL1 |
| 26 | RALGAPA1 | 56 | PPP1R3B | 86 | APLP2 | 116 | CAST |
| 27 | BACE2 | 57 | ESYT2 | 87 | SAT1 | 117 | ANXA2P2 |
| 28 | SLC22A17 | 58 | MALT1 | 88 | TMCO3 | 118 | CAMSAP2 |
| 29 | TMCO3 | 59 | ZDHHC22 | 89 | CNIH4 | 119 | MUM1 |
| 30 | NRP2 | 60 | IRF1 | 90 | NRXN1 | 120 | SERTAD1 |

FIG. 8B

| Rank | Gene names | Rank | Gene names | Rank | Gene names | Rank | Gene names | Rank | Gene names | Rank | Gene names |
|---|---|---|---|---|---|---|---|---|---|---|---|
| 1 | THRA | 31 | SPATA2 | 61 | ABAT | 91 | BHLHE40 | 121 | CAMK2G | 151 | LIMCH1 |
| 2 | ALDOC | 32 | SUSD4 | 62 | CAMTA1 | 92 | CYP46A1 | 122 | OGFOD3 | 152 | RAB6B |
| 3 | FXYD6 | 33 | TCEAL2 | 63 | BEX4 | 93 | FAM127A | 123 | COL6A1 | 153 | ARHGEF4 |
| 4 | ITPR3 | 34 | FAM192A | 64 | PIK3R1 | 94 | ITGA4 | 124 | ICAM1 | 154 | LAMB1 |
| 5 | FTO | 35 | RAB27A | 65 | MAPT | 95 | PAAF1 | 125 | RBMS1 | 155 | APC |
| 6 | NRXN1 | 36 | ABHD10 | 66 | FDFT1 | 96 | DZIP3 | 126 | NRP1 | 156 | NFE2L3 |
| 7 | ITGB3 | 37 | GORASP1 | 67 | TJP2 | 97 | NRP2 | 127 | GMFB | 157 | C1ORF61 |
| 8 | CLASP2 | 38 | C14ORF132 | 68 | RUFY3 | 98 | TRAPPC2L | 128 | CPD | 158 | LOX |
| 9 | AKTIP | 39 | NCOA1 | 69 | NDUFS1 | 99 | ERBB4 | 129 | MYO18A | 159 | B3GAT1 |
| 10 | WWTR1 | 40 | KIF5C | 70 | HEXB | 100 | ADD3 | 130 | ABAT | 160 | TSSC1 |
| 11 | THRA | 41 | CLCN6 | 71 | LAMC1 | 101 | ANKRD46 | 131 | LAMA4 | 161 | NRXN1 |
| 12 | SHC1 | 42 | SERPINE1 | 72 | GTDC1 | 102 | NRP2 | 132 | GNAZ | 162 | UGGT1 |
| 13 | OMG | 43 | NDRG2 | 73 | KDELR3 | 103 | PFN2 | 133 | KCNQ2 | 163 | ICAM1 |
| 14 | SVIL | 44 | TTYH1 | 74 | ATP9A | 104 | BLCAP | 134 | ZNF189 | 164 | SLC6A1 |
| 15 | TSPYL4 | 45 | ACO2 | 75 | MAPT | 105 | NAP1L3 | 135 | TUBB4A | 165 | SLC2A3 |
| 16 | OSMR | 46 | DESI1 | 76 | SC5D | 106 | PKIA | 136 | KIF5C | 166 | HMGCS1 |
| 17 | BCAT1 | 47 | PMAIP1 | 77 | SLC9A6 | 107 | PFKM | 137 | CA12 | 167 | CEP68 |
| 18 | KIF1B | 48 | APBA2 | 78 | ALDH5A1 | 108 | TPM4 | 138 | ATP8A1 | 168 | BCR |
| 19 | CTNND2 | 49 | ADGRB3 | 79 | WEE1 | 109 | NOL12 | 139 | TMEM35B | 169 | EDEM1 |
| 20 | TNFRSF10B | 50 | NCAN | 80 | SLC22A17 | 110 | MAPT | 140 | RBMS1 | 170 | ABHD6 |
| 21 | IQGAP1 | 51 | NRXN2 | 81 | CTIF | 111 | COL6A1 | 141 | ASRGL1 | 171 | NGRN |
| 22 | GABARAPL2 | 52 | SLC20A1 | 82 | RTN3 | 112 | FDFT1 | 142 | PIK3R1 | 172 | DOPEY1 |
| 23 | IQGAP1 | 53 | PRKACB | 83 | SDC1 | 113 | MR1 | 143 | MARCKSL1 | 173 | NCOA1 |
| 24 | NRXN2 | 54 | NTM | 84 | ADAM22 | 114 | HIP1R | 144 | THTPA | 174 | BEX1 |
| 25 | WASF3 | 55 | NUDT3 | 85 | ADGRE5 | 115 | N/A | 145 | ANXA2P2 | 175 | APC |
| 26 | ITPR3 | 56 | PLCB1 | 86 | SCN3A | 116 | NCALD | 146 | CHSY1 | 176 | RUNX1 |
| 27 | FUT9 | 57 | MMP14 | 87 | PTBP2 | 117 | KIF21B | 147 | COL6A1 | 177 | KCNB1 |
| 28 | SHC1 | 58 | CLIP3 | 88 | RAB27A | 118 | SEC24A | 148 | MAP1A | 178 | PPP2R2B |
| 29 | CLASP2 | 59 | VMP1 | 89 | TNFRSF12A | 119 | GDF15 | 149 | WASF1 | 179 | LOX |
| 30 | PEA15 | 60 | ADD1 | 90 | APBA2 | 120 | GRIA2 | 150 | ACACA | 180 | PHLPP1 |

FIG. 8C

| | | Gene name | | |
|---|---|---|---|---|
| | | Glut3 | ALDOC | PFKM |
| Dataset name | Freije | 0.0016 | 0.022 | 0.00073 |
| | TCGA | 0.000000021 | 0.0037 | 0.47 |
| | Lee | 0.0196 | 0.12 | 0.56 |

FIG. 9

| Family of genes/Pathway | Name | Sequence | SEQ ID NO: |
|---|---|---|---|
| Housekeeping genes | Cyclo FWD | CAGGTCCTGGCATCTTGTCC | SEQ ID NO:1 |
| | Cyclo REV | TTGCTGGTCTTGCCATTCCT | SEQ ID NO:2 |
| | Tuba2 FWD | AGGAGCTGGCAAGCATGTG | SEQ ID NO:3 |
| | Tuba2 REV | CGGTGCGAACTTCATCGAT | SEQ ID NO:4 |
| | ALAS1 FWD | CTCACCACACACCCCAGATG | SEQ ID NO:5 |
| | ALAS1 REV | AGTTCCAGCCCCACTTGCT | SEQ ID NO:6 |
| | EEF1A1 FWD | AGCAAAAATGACCCACCAATG | SEQ ID NO:7 |
| | EEF1A1 REV | GGCCTGGATGGTTCAGGATA | SEQ ID NO:8 |
| Glut transporters | SLC2A1 FWD | TATCGTCAACACGGCCTTCACTGT | SEQ ID NO:9 |
| | SLC2A1 REV | AACAGCTCCTCGGGTGTCTTATCA | SEQ ID NO:10 |
| | SLC2A2 FWD | CAACCATTGGAGTTGGCGCTGTAA | SEQ ID NO:11 |
| | SLC2A2 REV | AGGTCCACAGAAGTCCGCAATGTA | SEQ ID NO:12 |
| | SLC2A3 FWD | TCCACGCTCATGACTGTTTC | SEQ ID NO:13 |
| | SLC2A3 REV | GCCTGGTCCAATTTCAAAGA | SEQ ID NO:14 |
| | SLC2A6 FWD | CGGAAGCTGAGCATCATGT | SEQ ID NO:15 |
| | SLC2A6 REV | GGGAGCAATCTCAGACACGTA | SEQ ID NO:16 |
| Integrins | ITGB3 FWD | GTGACCTGAAGGAGAATCTGC | SEQ ID NO:17 |
| | ITGB3 REV | TCACTCACTGGGAACTCGATG | SEQ ID NO:18 |
| Stem cells | CD133 FWD | ACTCCCATAAAGCTGGACCC | SEQ ID NO:19 |
| | CD133 REV | TCAATTTTGGATTCATATGCCTT | SEQ ID NO:20 |
| | Oct4 FWD | TCTCCCATGCATTCAAACTGAG | SEQ ID NO:21 |
| | Oct4 REV | CCTTTGTGTTCCCAATTCCTTC | SEQ ID NO:22 |
| | Nanog FWD | TCTCCCATGCATTCAAACTGAG | SEQ ID NO:23 |
| | Nanog REV | CCCACTTCTGCAGAGAATAGTG | SEQ ID NO:24 |
| Astrocytes | GFAP FWD | AAGAGATCCGCACGCAGTAT | SEQ ID NO:25 |
| | GFAP REV | AGGTCAAGGACTGCAACTGG | SEQ ID NO:26 |
| Neurons | Tubb3 FWD | CGGTGGTGGAACCCTACAAC | SEQ ID NO:27 |
| | Tubb3 REV | AGGTGGTGACTCCGCTCAT | SEQ ID NO:28 |
| YAP/TAZ | hYAP FWD | CCAAGGCTTGACCCTCGTTTTG | SEQ ID NO:29 |
| | hYAP REV | TCGCATCTGTTGCTGCTGGTTG | SEQ ID NO:30 |
| | hTAZ FWD | TCACCAACACCAGCAGCAGATG | SEQ ID NO:31 |
| | hTAZ REV | GCATTCTCTGAAGCCGCAGTTTC | SEQ ID NO:32 |

FIG. 10A

| | | | |
|---|---|---|---|
| Mitochondrial oxidative phosphorylation | PISD FWD | CCACCGACTGGACTGTGTC | SEQ ID NO:33 |
| | PISD REV | CCGCTCGTTATGGCAGAAGA | SEQ ID NO:34 |
| | PISD REV | CCGATGGGCTAATCACGCTG | SEQ ID NO:35 |
| | ACAD9 FWD | AGTTCTTGGGACCCGTGGAA | SEQ ID NO:36 |
| | ACAD9 REV | GTCTTGAGTACATGGTGTTGGAG | SEQ ID NO:37 |
| Glycolytic pathway | HK3 FWD | GGACAGGAGCACCCTCATTTC | SEQ ID NO:38 |
| | HK3 REV | CCTCCGAATGGCATCTCTCAG | SEQ ID NO:39 |
| | HK2 FWD | GAGCCACCACTCACCCTACT | SEQ ID NO:40 |
| | HK2 REV | CCAGGCATTCGGCAATGTG | SEQ ID NO:41 |
| | HK1 FWD | GCTCTCCGATGAAACTCTCATAG | SEQ ID NO:42 |
| | HK1 REV | GGACCTTACGAATGTTGGCAA | SEQ ID NO:43 |
| | GPI FWD | CAAGGACCGCTTCAACCACTT | SEQ ID NO:44 |
| | GPI REV | CCAGGATGGGTGTGTTTGACC | SEQ ID NO:45 |
| | ALDOC FWD | ATGCCTCACTCGTACCCAG | SEQ ID NO:46 |
| | ALDOC REV | TTTCCACCCCAATTTGGCTCA | SEQ ID NO:47 |
| | PFKP FWD | GCATGGGTATCTACGTGGGG | SEQ ID NO:48 |
| | PFKP REV | CTCTGCGATGTTTGAGCCTC | SEQ ID NO:49 |
| | TPI1 FWD | CTCATCGGCACTCTGAACG | SEQ ID NO:50 |
| | TPI1 REV | GCGAAGTCGATATAGGCAGTAGG | SEQ ID NO:51 |
| | Gapdh FWD | GCACAAGAGGAAGAGAGAGACC | SEQ ID NO:52 |
| | Gapdh REV | AGGGGAGATTCAGTGTGGTG | SEQ ID NO:53 |
| | PGK1 FWD | GAACAAGGTTAAAGCCGAGCC | SEQ ID NO:54 |
| | PGK1 REV | GTGGCAGATTGACTCCTACCA | SEQ ID NO:55 |
| | PKM2 FWD | ATGTCGAAGCCCCATAGTGAA | SEQ ID NO:56 |
| | PKM2 REV | TGGGTGGTGAATCAATGTCCA | SEQ ID NO:57 |
| | ENO1 FWD | GCCGTGAACGAGAAGTCCTG | SEQ ID NO:58 |
| | ENO1 REV | ACGCCTGAAGAGACTCGGT | SEQ ID NO:59 |
| | ALDOA FWD | ATGCCCTACCAATATCCAGCA | SEQ ID NO:60 |
| | ALDOA REV | GCTCCCAGTGGACTCATCTG | SEQ ID NO:61 |
| Pentose Phosphate Pathway | G6PD FWD | CGAGGCCGTCACCAAGAAC | SEQ ID NO:62 |
| | G6PD REV | GTAGTGGTCGATGCGGTAGA | SEQ ID NO:63 |
| | PGLS FWD | GGAGCCTCGTCTCGATGCTA | SEQ ID NO:64 |
| | PGLS REV | GAGAGAAGATGCGTCCGGT | SEQ ID NO:65 |

FIG. 10B

| | | | |
|---|---|---|---|
| | PDG FWD | ATGGCCCAAGCTGACATCG | SEQ ID NO:66 |
| | PGD REV | AAAGCCGTGGTCATTCATGTT | SEQ ID NO:67 |
| | TKT FWD | TCCACACCATGCGCTACAAG | SEQ ID NO:68 |
| | TKT REV | CAAGTCGGAGCTGATCTTCCT | SEQ ID NO:69 |
| | TALDO1 FWD | CTCACCCGTGAAGCGTCAG | SEQ ID NO:70 |
| | TALDO1 REV | GTTGGTGGTAGCATCCTGGG | SEQ ID NO:71 |
| Neural GBM subtype | SYT1 FWD | GTGAGCGAGAGTCACCATGAG | SEQ ID NO:72 |
| | SYT1 REV | CCCACGGTGGCAATGGAAT | SEQ ID NO:73 |
| | SYT5 FWD | AGACGCTGAACCCTCACTTTG | SEQ ID NO:74 |
| | SYT5 REV | CGAAGTCGTACACCGCCAT | SEQ ID NO:75 |
| | SLC12A5 FWD | TGCTCCTGTACGATGCTCAC | SEQ ID NO:76 |
| | SLC12A5 REV | GCTCCTGCAAAGGTAGTGC | SEQ ID NO:77 |
| | PACSIN1 FWD | GAACAGCAAGACGGAGCAATC | SEQ ID NO:78 |
| | PACSIN1 REV | GACCAGCCGCTTTTCCTCAA | SEQ ID NO:79 |
| | RGS4 FWD | ACATCGGCTAGGTTTCCTGC | SEQ ID NO:80 |
| | RGS4 REV | GTTGTGGGAAGAATTGTGTTCAC | SEQ ID NO:81 |
| | MAL2 FWD | GTCCGTGACAGCGTTTTTCTT | SEQ ID NO:82 |
| | MAL2 REV | AATTGAGGCTGCTACGTTTATGT | SEQ ID NO:83 |
| Proneural GBM subtype | DLL3 FWD | CACTCCCGGATGCACTCAAC | SEQ ID NO:84 |
| | DLL3 REV | GATTCCAATCTACGGACGAGC | SEQ ID NO:85 |
| | DCX FWD | GACAGCCCACTCTTTTGAGC | SEQ ID NO:86 |
| | DCX REV | TGGGTTTCCCTTCATGACTC | SEQ ID NO:87 |
| | OLIG2 FWD | CAGAAGCGCTGATGGTCATA | SEQ ID NO:88 |
| | OLIG2 REV | TCGGCAGTTTTGGGTTATTC | SEQ ID NO:89 |
| | ERBB3 FWD | GGTGATGGGGAACCTTGAGAT | SEQ ID NO:90 |
| | ERBB3 REV | CTGTCACTTCTCGAATCCACTG | SEQ ID NO:91 |
| | PDGFRA FWD | TGGCAGTACCCCATGTCTGAA | SEQ ID NO:92 |
| | PDGFRA REV | CCAAGACCGTCACAAAAAGGC | SEQ ID NO:93 |
| | P2RX7 FWD | TATGAGACGAACAAAGTCACTCG | SEQ ID NO:94 |
| | P2RX7 REV | GCAAAGCAAACGTAGGAAAAGAT | SEQ ID NO:95 |
| | BMP2 FWD | ACTACCAGAAACGAGTGGGAA | SEQ ID NO:96 |
| | BMP2 REV | GCATCTGTTCTCGGAAAACCT | SEQ ID NO:97 |
| | SOX2-FWD | GGGAAATGGGAGGGGTGCAAAAGA | SEQ ID NO:98 |

FIG. 10C

| | SOX-2-REV | TTGCGTGAGTGTGGATGGGATTGGT | SEQ ID NO:99 |
|---|---|---|---|
| Mesenchymal GBM subtype | CD44 FWD | AAGGTGGAGCAAACACAACC | SEQ ID NO:100 |
| | CD44 REV | AGCTTTTTCTTCTGCCCACA | SEQ ID NO:101 |
| | YKL40 FWD | TCAAGAACAGGAACCCCAAC, | SEQ ID NO:102 |
| | YKL40 REV | AAAATTCGGCCTTCATTTCCT | SEQ ID NO:103 |
| | MET FWD | CCCCACCCTTTGTTCAG | SEQ ID NO:104 |
| | MET REV | TCAGCCTTGTCCCTCCT | SEQ ID NO:105 |
| | RelB FWD | TGAATGTGGTGAGGATCTGC | SEQ ID NO:106 |
| | RelB REV | CGCAGCTCTGATGTGTTTGT | SEQ ID NO:109 |
| | LGALS3 FWD | GTGAAGCCCAATGCAAACAGA | SEQ ID NO:108 |
| | LGALS3 REV | AGCGTGGGTTAAAGTGGAAGG | SEQ ID NO:109 |
| | LOX FWD | CCTACTACATCCAGGCGTCCA | SEQ ID NO:110 |
| | LOX REV | CATAATCTCTGACATCTGCCCCTGT | SEQ ID NO:111 |
| | THBS1 FWD | TGCTATCACAACGGAGTTCAGT | SEQ ID NO:112 |
| | THBS1 REV | GCAGGACACCTTTTTGCAGATG | SEQ ID NO:113 |
| | LAMB1 FWD | CACAAGCCCGAACCCTACTG | SEQ ID NO:114 |
| | LAMB1 REV | GACCACATTTTCAATGAGATGGC | SEQ ID NO:115 |
| | DAB2 FWD | GTAGAAACAAGTGCAACCAATGG | SEQ ID NO:116 |
| | DAB2 REV | GCCTTTGAACCTTGCTAAGAGA | SEQ ID NO:117 |
| | S100A4 FWD | GATGAGCAACTTGGACAGCAA | SEQ ID NO:118 |
| | S100A4 REV | CTGGGCTGCTTATCTGGGAAG | SEQ ID NO:119 |
| | COL1A2 FWD | GAGCGGTAACAAGGGTGAGC | SEQ ID NO:120 |
| | COL1A2 REV | CTTCCCCATTAGGGCCTCTC | SEQ ID NO:121 |
| | MMP9 FWD | TGTACCGCTATGGTTACACTCG | SEQ ID NO:122 |
| | MMP9 REV | GGCAGGGACAGTTGCTTCT | SEQ ID NO:123 |
| | VEGFA FWD | AGGGCAGAATCATCACGAAGT | SEQ ID NO:124 |
| | VEGFA REV | AGGGTCTCGATTGGATGGCA | SEQ ID NO:125 |
| | IGFBP2 FWD | GACAATGGCGATGACCACTCA | SEQ ID NO:126 |
| | IGFBP2 REV | CAGCTCCTTCATACCCGACTT | SEQ ID NO:127 |
| Classical GBM subtype | Gli2 FWD | CTGCCTCCGAGAAGCAAGAAG | SEQ ID NO:128 |
| | Gli2 REV | GCATGGAATGGTGGCAAGAG | SEQ ID NO:129 |
| | EGFR FWD | CAGCGCTACCTTGTCATTCA | SEQ ID NO:130 |
| | EGFR REV | AGCTTTGCAGCCCATTTCTA | SEQ ID NO:131 |

FIG. 10D

| ACSBG1 FWD | ACACTGTGCATCGGATGTTCT | SEQ ID NO:132 |
|---|---|---|
| ACSBG1 REV | AGGAGATGTGTTCCCACTTGT | SEQ ID NO:133 |
| IGF2 FWD | GTGGCATCGTTGAGGAGTG | SEQ ID NO:134 |
| IGF2 REV | CACGTCCCTCTCGGACTTG | SEQ ID NO:135 |
| Nestin FWD | GGAAGAGAACCTGGGAAAGG | SEQ ID NO:136 |
| Nestin REV | CTTGGTCCTTCTCCACCGTA | SEQ ID NO:137 |
| shh FWD | CTCGCTGCTGGTATGCTCG | SEQ ID NO:138 |
| shh REV | ATCGCTCGGAGTTTCTGGAGA | SEQ ID NO:139 |
| Notch3 FWD | CGTGGCTTCTTTCTACTGTGC | SEQ ID NO:140 |
| Notch3 REV | CGTTCACCGGATTTGTGTCAC | SEQ ID NO:141 |
| GAS1 FWD | ATGCCGCACCGTCATTGAG | SEQ ID NO:142 |
| GAS1 REV | TCATCGTAGTAGTCGTCCAGG | SEQ ID NO:143 |
| MCM2 FWD | CCGTGACCTTCCACCATTTGA | SEQ ID NO:144 |
| MCM2 REV | GGTAGTCCCTTTCCATGCCAT | SEQ ID NO:145 |
| CENPF FWD | CTCTCCCGTCAACAGCGTTC | SEQ ID NO:146 |
| CENPF REV | GTTGTGCATATTCTTGGCTTGC | SEQ ID NO:147 |
| TOP2A FWD | TTAATGCTGCGGACAACAAACA | SEQ ID NO:148 |
| TOP2A REV | CGACCACCTGTCACTTTCTTTT | SEQ ID NO:149 |
| KCNF1 FWD | GCCAGCGACGACATAGAGATA | SEQ ID NO:150 |
| KCNF1 REV | CCAGCCAAGCAGTTGATGAG | SEQ ID NO:151 |

FIG. 10E

Glut3 non-addicted signature

| | | | |
|---|---|---|---|
| 1 | NNMT | 76 | MBD4 |
| 2 | S100A8 | 77 | IL1RN |
| 3 | MRC1 | 78 | NUCB2 |
| 4 | SLC2A3 | 79 | GRK5 |
| 5 | TAGLN | 80 | GLRX2 |
| 6 | SERPINE1 | 81 | NTAN1 |
| 7 | LOX | 82 | PPP1R15A |
| 8 | CYP1B1 | 83 | MGAT2 |
| 9 | MAFF | 84 | FAM162A |
| 10 | CXCL8 | 85 | AFF1 |
| 11 | CAV1 | 86 | PARVB |
| 12 | THBS1 | 87 | COPB1 |
| 13 | G0S2 | 88 | FGR |
| 14 | P4HA2 | 89 | NUP98 |
| 15 | FCGR2B | 90 | VNN2 |
| 16 | AHNAK2 | 91 | CAPZA1 |
| 17 | IL1R1 | 92 | LGALS8 |
| 18 | DYNLT3 | 93 | ETF1 |
| 19 | ACTA2 | 94 | SHQ1 |
| 20 | DCN | 95 | BNIP3L |
| 21 | S100A9 | 96 | GNA15 |
| 22 | THBD | 97 | MBD4 |
| 23 | CAV2 | 98 | ARPC2 |
| 24 | PLOD2 | 99 | COQ10B |
| 25 | ACSL1 | 100 | ATP13A3 |
| 26 | SNX10 | 101 | FYCO1 |
| 27 | BHLHE40 | 102 | SECTM1 |
| 28 | TNFAIP3 | 103 | HCCS |
| 29 | IL1R2 | 104 | NANS |
| 30 | PCSK1 | 105 | TPI1 |
| 31 | ARHGAP29 | 106 | SEPHS2 |
| 32 | ACTN1 | 107 | SLC36A1 |
| 33 | PRSS23 | 108 | GTF2H1 |
| 34 | FHL2 | 109 | CARS |
| 35 | RGS2 | 110 | SRPRA |
| 36 | TPM1 | 111 | SEC31A |
| 37 | FOSL2 | 112 | GTF2E2 |

FIG. 11A

| 38 | PLAU | 113 | KDM2A |
| 39 | CEBPB | 114 | SLC16A6 |
| 40 | UPP1 | 115 | VDR |
| 41 | SYNPO | 116 | MANBA |
| 42 | NDRG1 | 117 | EXT2 |
| 43 | SLC39A14 | 118 | PIGB |
| 44 | AQP9 | 119 | DNAJC25-GNG10 |
| 45 | LDHA | 120 | STX4 |
| 46 | HRH1 | 121 | MED8 |
| 47 | MICAL2 | 122 | AP3S1 |
| 48 | ANGPTL4 | 123 | YIPF1 |
| 49 | HTATIP2 | 124 | ACBD3 |
| 50 | OSBPL10 | 125 | SERTAD3 |
| 51 | MIR22HG | 126 | SRP54 |
| 52 | CPD | 127 | ITPKC |
| 53 | WIPI1 | 128 | TBC1D8B |
| 54 | KHNYN | 129 | ERO1A |
| 55 | VMP1 | 130 | IRAK3 |
| 56 | HIST1H2AC | 131 | VPS37C |
| 57 | REXO2 | 132 | CEPT1 |
| 58 | TGM2 | 133 | WDR44 |
| 59 | FTH1 | 134 | TMED2 |
| 60 | EFEMP2 | 135 | KIF16B |
| 61 | SEC23A | 136 | CCPG1 |
| 62 | UAP1 | 137 | RIOK3 |
| 63 | ZNF395 | 138 | CHMP4A |
| 64 | SLC25A24 | 139 | FTH1P5 |
| 65 | POLR1D | 140 | TASP1 |
| 66 | RBPMS | 141 | MAPK13 |
| 67 | PGK1 | 142 | SUN1 |
| 68 | GSTO1 | 143 | NFE2L3 |
| 69 | STBD1 | | |
| 70 | SAT1 | | |
| 71 | PPCS | | |
| 72 | SPAG4 | | |
| 73 | RAB27A | | |
| 74 | CD55 | | |
| 75 | TPGS2 | | |

FIG. 11B

Glut3 addicted signature

| | | | | | |
|---|---|---|---|---|---|
| 1 | NDRG2 | 76 | GLYR1 | 151 | PPIL2 |
| 2 | BCAN | 77 | ANAPC5 | 152 | MDC1 |
| 3 | OLIG2 | 78 | ANP32A | 153 | POU3F4 |
| 4 | PCDHGA4 | 79 | SEMA6A | 154 | AHI1 |
| 5 | DLL3 | 80 | GTF2I | 155 | KANSL3 |
| 6 | PCDHGB3 | 81 | SRPK2 | 156 | CREBBP |
| 7 | ADGRG1 | 82 | HSP90AB1 | 157 | OSBPL7 |
| 8 | KCNN3 | 83 | CREB1 | 158 | FRS2 |
| 9 | FHL1 | 84 | KLHL22 | 159 | NCAPH2 |
| 10 | PSAT1 | 85 | TCAF1P1 | 160 | KLF15 |
| 11 | ID4 | 86 | SLC1A4 | 161 | RPS28 |
| 12 | YWHAE | 87 | H2AFX | 162 | JRK |
| 13 | MAP2 | 88 | PTPN11 | 163 | USF2 |
| 14 | ETV1 | 89 | PATZ1 | 164 | KMT2D |
| 15 | ZEB1 | 90 | PIP4K2B | 165 | NCOA2 |
| 16 | CNTN1 | 91 | TBC1D5 | 166 | RECQL5 |
| 17 | MAPK8IP1 | 92 | NAB1 | 167 | PLLP |
| 18 | PAFAH1B1 | 93 | DGCR2 | 168 | CEP97 |
| 19 | ZBTB18 | 94 | GTF3C2 | 169 | HSD17B1 |
| 20 | MARCKS | 95 | PRKAB1 | 170 | DNAJC16 |
| 21 | TAF9B | 96 | DTX3 | 171 | HSF2 |
| 22 | PLXNB1 | 97 | HMGB1P1 | | |
| 23 | GLUD2 | 98 | NPRL3 | | |
| 24 | SPAG9 | 99 | ARHGAP35 | | |
| 25 | GPSM2 | 100 | CBX5 | | |
| 26 | HACD3 | 101 | POU3F3 | | |
| 27 | SPTBN1 | 102 | GDAP1 | | |
| 28 | RAD21 | 103 | TOM1L2 | | |
| 29 | NREP | 104 | KCTD15 | | |
| 30 | WAC | 105 | PATZ1 | | |
| 31 | ANKFY1 | 106 | WASL | | |
| 32 | KCNJ10 | 107 | ZKSCAN1 | | |
| 33 | DHX9 | 108 | AKAP1 | | |
| 34 | PEA15 | 109 | KCTD20 | | |
| 35 | EPHB1 | 110 | ZNF510 | | |
| 36 | GPRC5B | 111 | PEX1 | | |
| 37 | SPTBN1 | 112 | NCAM1 | | |

FIG. 11C

| 38 | NONO | 113 | OSGEPL1 | |
|---|---|---|---|---|
| 39 | PTPN11 | 114 | GNAQ | |
| 40 | HIPK2 | 115 | HDAC6 | |
| 41 | TSPAN3 | 116 | KMT2A | |
| 42 | ZNF711 | 117 | MATR3 | |
| 43 | HMGCS1 | 118 | ZC4H2 | |
| 44 | FBXW11 | 119 | POLDIP3 | |
| 45 | ANP32A | 120 | CDC5L | |
| 46 | PATZ1 | 121 | QRSL1 | |
| 47 | FOXO3B/FOXO3 | 122 | WBP11 | |
| 48 | RPS20 | 123 | CDYL | |
| 49 | ELMO2 | 124 | CDK17 | |
| 50 | PTK2 | 125 | ABI2 | |
| 51 | ARHGEF4 | 126 | RXRB | |
| 52 | MYO6 | 127 | CEP68 | |
| 53 | H2AFV | 128 | RGS12 | |
| 54 | TMPO | 129 | DCAKD | |
| 55 | TJP1 | 130 | ABI2 | |
| 56 | TNK2 | 131 | PIK3R2 | |
| 57 | ARHGEF7 | 132 | KMT2A | |
| 58 | GNG4 | 133 | RASA3 | |
| 59 | QKI | 134 | CDYL | |
| 60 | PRKDC | 135 | CASKIN2 | |
| 61 | ADD1 | 136 | SKP2 | |
| 62 | DST | 137 | DSTYK | |
| 63 | PSIP1 | 138 | ATP5S | |
| 64 | ZMYND11 | 139 | AFDN | |
| 65 | USP34 | 140 | KLHL12 | |
| 66 | EPN2 | 141 | LGR5 | |
| 67 | RBM8A | 142 | HTATSF1 | |
| 68 | APC | 143 | ZNF273 | |
| 69 | HP1BP3 | 144 | LLGL1 | |
| 70 | CAMSAP2 | 145 | GTF2IRD2 | |
| 71 | KIDINS220 | 146 | HMGB1P5 | |
| 72 | PAFAH1B1 | 147 | MIIP | |
| 73 | RBM8A | 148 | HMGB1P4 | |
| 74 | XPO7 | 149 | LDAH | |
| 75 | CCDC88A | 150 | EHMT2 | |

FIG. 11D

|         | SLC2A3 | 202499_S_AT |
|---------|--------|-------------|
| 0.00144 | ITGB3  | 204625_s_at |
| 0.0047  | ITGB3  | 204627_s_at |
| 0.00725 | ITGB3  | 204628_s_at |
| 0.00763 | ITGB3  | 204626_s_at |
| 0.0151  | ITGB3  | 215240_at   |

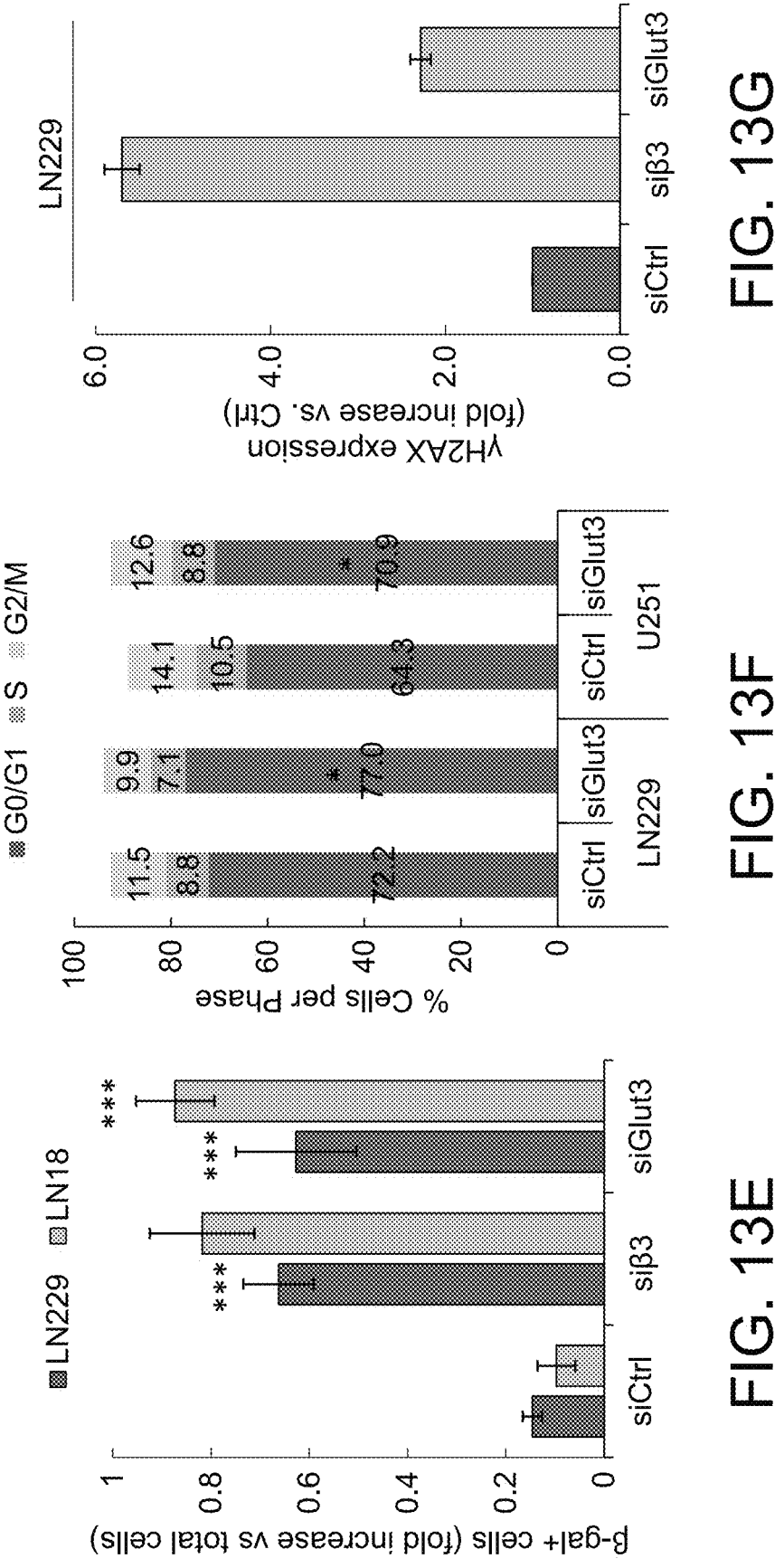

Brain GBM tissue array

β3 / Glut3

| | Mes GBM150 | Mes GBM59 | Clas GBM14 | ProN GBM64 | ProN GBM85 |
|---|---|---|---|---|---|
| | | | | | |
| | Glut3 non-addicted signature | | | | |
| CAV1 | 163 | 44 | 1 | 4 | 1 |
| CAV2 | 14 | 4 | 0 | 6 | 1 |
| TAGLN | 4 | 1 | 1 | 2 | 1 |
| SERPINE1 | 241 | 4 | 1 | 2 | 0 |
| THBS1 | 45 | 8 | 0 | 0 | 16 |
| P4HA2 | 3 | 47 | 0 | 0 | 1 |
| AHNAK2 | 15 | 4 | 0 | 0 | 0 |
| DYNLT3 | 24 | 48 | 6 | 5 | 13 |
| ACTA2 | 5 | 1 | 1 | 3 | 1 |
| PRSS23 | 5 | 4 | 0 | 1 | 2 |
| FHL2 | 41 | 8 | 0 | 5 | 0 |
| TPM1 | 13 | 8 | 9 | 6 | 4 |
| PLAU | 396 | 18 | 3 | 1 | 1 |
| UPP1 | 17 | 12 | 0 | 4 | 1 |
| NDRG1 | 31 | 3 | 2 | 1 | 5 |
| LDHA | 137 | 222 | 48 | 45 | 30 |
| ANGPTL4 | 19 | 10 | 2 | 0 | 0 |
| MIR22HG | 7 | 13 | 1 | 1 | 1 |
| VMP1 | 19 | 25 | 11 | 11 | 8 |
| PGK1 | 100 | 173 | 35 | 24 | 29 |
| TPI1 | 315 | 303 | 144 | 84 | 89 |
| GSTO1 | 46 | 76 | 17 | 24 | 9 |

FIG. 18A

| | Glut3 addicted signature | | | | |
|---|---|---|---|---|---|
| NDRG2 | 6 | 0 | 11 | 15 | 39 |
| BCAN | 1 | 1 | 60 | 170 | 743 |
| OLIG2 | 73 | 1 | 6 | 142 | 103 |
| DLL3 | 0 | 0 | 0 | 16 | 90 |
| FHL1 | 13 | 24 | 27 | 44 | 49 |
| PSAT1 | 26 | 14 | 72 | 76 | 66 |
| ID4 | 47 | 13 | 137 | 18 | 62 |
| MAP2 | 11 | 9 | 69 | 101 | 78 |
| ETV1 | 15 | 18 | 29 | 8 | 39 |
| ZEB1 | 23 | 22 | 55 | 39 | 7 |
| CNTN1 | 1 | 9 | 0 | 66 | 21 |
| MARCKS | 72 | 49 | 82 | 150 | 326 |
| TAF9B | 7 | 28 | 22 | 11 | 26 |
| PLXNB1 | 7 | 1 | 17 | 28 | 44 |
| GPSM2 | 7 | 16 | 14 | 14 | 27 |
| KCNJ10 | 28 | 0 | 23 | 22 | 22 |
| DHX9 | 35 | 35 | 59 | 50 | 59 |
| PEA15 | 113 | 34 | 133 | 143 | 196 |
| PTPN11 | 15 | 16 | 43 | 39 | 19 |
| HIPK2 | 4 | 4 | 21 | 27 | 25 |
| ZNF711 | 3 | 1 | 11 | 20 | 36 |
| MYO6 | 4 | 4 | 8 | 3 | 9 |
| SEMA6A | 2 | 3 | 6 | 6 | 14 |
| POU3F3 | 23 | 7 | 62 | 32 | 13 |
| GNG4 | 0 | 0 | 3 | 34 | 22 |
| DGCR2 | 9 | 13 | 14 | 25 | 19 |
| ARHGEF7 | 3 | 3 | 8 | 13 | 20 |
| ARHGAP35 | 10 | 4 | 13 | 12 | 16 |
| PIP4K2B | 19 | 13 | 27 | 36 | 25 |
| PRKDC | 11 | 11 | 32 | 20 | 26 |

FIG. 18B

Screen for markers (mRNA/protein) to determine Glut3 addiction:

| | Marker | Addicted signature | Non-addicted signature |
|---|---|---|---|
| 1 DUAL POSITIVE for integrin β3 and GLUT3 | ITGB3 | high | high or low |
| | SLC2A3 | high | high or low |
| 2 HIGH expression of markers associated with "addiction signature" | MAPK8IP1 | high | low |
| | SEMA6A | high | low |
| | ARHGEF7 | high | low |
| | PAFAH1B1 | high | low |
| 3 LOW expression of markers associated with "non-addiction signature" | ZNF395 | low | high |
| | WAC | low | high |
| | PRSS23 | low | high |
| | CCPG1 | low | high |
| | LOX | low | high |
| | SLC36A1 | low | high |
| | PLOD2 | low | high |
| | VDR | low | high |
| | LDHA | low | high |

FIG. 23

METHODS FOR TREATING DRUG RESISTANT CANCERS

RELATED APPLICATIONS

This application is a continuation of U.S. utility patent application U.S. Ser. No. 16/622,796, filed Dec. 13, 2019, which is a national phase application claiming benefit of priority under 35 U.S.C. § 371 to Patent Convention Treaty (PCT) International Application serial number PCT/US2018/037595, filed Jun. 14, 2018, which claims the benefit of priority to U.S. Provisional Application No. 62/519,734, filed Jun. 14, 2017. The aforementioned applications are expressly incorporated herein by reference in their entirety and for all purposes.

GOVERNMENT RIGHTS

This invention was made with government support under CA045726 awarded by the National Institutes of Health. The government has certain rights in the invention.

REFERENCE TO ELECTRONIC SEQUENCE LISTING

The application contains a Sequence Listing which has been submitted electronically in .XML format and is hereby incorporated by reference in its entirety. Said .XML copy, created on Aug. 28, 2023, is named "0321.128953C1.xml" and is 192,178 bytes in size. The sequence listing contained in this .XML file is part of the specification and is hereby incorporated by reference herein in its entirety. The Sequence Listing contains no new matter.

TECHNICAL FIELD

This invention generally relates to oncology. In alternative embodiments, provided are methods for determining whether a glioblastoma (GBM) tumor or GBM cancer cell will be sensitive to a treatment targeting the integrin avb3 (αvβ3) pathway, comprising determining whether the GBM tumor or the GBM cancer cell expresses both avb3+ and Glut3+ (also called SLC2A3+) along with (and also having) a specific genetic signature associated with Glut3 addiction, where in alternative embodiments a cell is Glut3 addicted if the GBM tumor or the GBM cancer cell has markers consistent with the Classical or the Proneural molecular subtypes of GBM, or, expresses (e.g., expresses mRNA or protein) markers consistent with a Glut3-addicted genetic-molecular signature, e.g., as listed in FIG. 11 or FIG. 23, wherein if a GBM tumor or the GBM cancer cell expresses both avb3+ and Glut3+ and this genetic/molecular signature is associated with Glut3 addiction, the GBM tumor or the GBM cancer cell will be (can be predicted to be) sensitive to (will be successfully treated by) the treatment targeting the integrin avb3 (αvβ3) pathway. Also provided herein are methods of treating glioblastoma (GBM) tumors found to be sensitive to agents targeting or inhibiting the integrin avb3 (αvβ3) pathway, wherein the sensitivity is determined by methods as provided herein.

BACKGROUND

In glioblastomas (GBMs), expression of αvβ3 (avb3) and its ligand vitronectin are both linked to tumor progression and invasive behavior at the tumor margin in the brain of patients with GBM (Gladson and Cheresh, 1991). This prompted development of cilengitide, a cyclic peptide antagonist capable of targeting the ligand binding site of a αvβ3. Despite encouraging phase I/II results showing a durable response to cilengitide for some patients (Nabors et al., 2007; Reardon et al., 2008), the phase III CENTRIC and phase II CORE trials failed to meet overall survival endpoints (Stupp et al., 2014). In a follow-up study, immunohistological analysis of tissues obtained during the CORE trial revealed that higher αvβ3 levels were associated with improved survival in patients treated with cilengitide (Weller et al., 2016). Because this was not the case for the CENTRIC trial, it is still not clear how to identify patients who may benefit from this drug.

SUMMARY

In alternative embodiments, provided are methods for: determining whether a glioblastoma (GBM) tumor or GBM cancer cell will be sensitive or responsive to a treatment targeting the integrin avb3 (αvβ3) pathway, comprising determining or having determined whether the GBM tumor or the GBM cancer cell expresses both avb3+ and Glut3+ along with (and also has) a genetic/molecular signature associated with Glut3 addiction, wherein in alternative embodiments a genetic/molecular signature associated with Glut3 addiction comprises the cell having markers consistent with the Classical or Proneural molecular subtypes of GBM, or the cell expresses (e.g., expresses mRNA or protein) markers consistent with a Glut3-addicted genetic-molecular signature, e.g., expresses markers at levels as listed in FIG. 11 or FIG. 23 (where a Glut3 addicted marker is expressed at high levels, and a Glut3 non-addicted marker is expressed at low levels), wherein if a GBM tumor or the GBM cancer cell expresses both avb3+ and Glut3+ and has a Glut3+ genetic/molecular signature, the GBM tumor or the GBM cancer cell will be (or can be predicted to be) sensitive to (will be successfully treated by) the treatment targeting the integrin avb3 (αvβ3) pathway.

Not all tumors with positive expression of αvβ3 and GLUT3 are sensitive to drugs targeting this pathway: there are two different ways that patients who will be sensitive to drugs targeting the integrin avb3 (αvβ3) pathway can be further divided after the expression of αvβ3/Glut3 is known. For the first way, GBM tumors can be characterized by their "GBM molecular subtype", and only tumors which have markers consistent with the Classical or Proneural subtypes will be sensitive to blockade of the αvβ3 pathway. Tumors with positive expression of both αvβ3/Glut3 but markers of the Mesenchymal subtype are not expected to be addicted to Glut3 and thus may not be sensitive to αvβ3 blockade. For the second way, provided herein is a list of genes (as illustrated in FIG. 11, see also FIG. 23) that can be used to predict (or determine) Glut3 addiction and αvβ3 blockade sensitivity independent of determining the GBM molecular subtype, i.e., if a tumor expresses αvβ3 and GLUT3 and expresses markers consistent with a Glut3-addicted gene signature, e.g., where the markers are expressed at levels as listed in FIG. 11 or FIG. 23, this signature is predictive of sensitivity to drugs targeting the integrin avb3 (αvβ3) pathway (i.e., the cells are "drug-sensitive" if they are sensitive, or responsive to, any drug, small molecule, protein, or any agent that targets the integrin avb3 (αvβ3) pathway). These exemplary decision-making processes are shown in the schematic illustrated in FIG. 6. Alternative methods to determine if a cell is Glut3 addicted are described below.

In alternative embodiments, the cancer or tumor cell treatment targets avb3, Glut3, PAK4, or YAP/TAZ. In alternative embodiments, the treatment comprises administration to an individual in need thereof cilengitide (or, 2-[(2S,5R, 8S,11S)-5-benzyl-11-{3-[(diaminomethylidene)amino]propyl}-7-methyl-3,6,9,12,15-pentaoxo-8-(propan-2-yl)-1,4,7, 10,13-pentaazacyclopentadecan-2-yl]acetic acid).

In alternative embodiments, provided are methods for determining whether a tumor or a cancer cell will be sensitive to (or can be killed or induced to senescence by) a treatment targeting the integrin avb3 ($\alpha v \beta 3$) pathway, comprising:

(a) determining or having determined whether the tumor or the cancer cell expresses both avb3+ and Glut3+, or determining whether the tumor or the cancer cell is an avb3+/Glut3+ tumor or cancer cell, and (b) determining or having determined whether the tumor or the cancer cell is Glut-3 addicted, wherein optionally determining or having determined whether the tumor or the cancer cell is Glut-3 addicted comprises:

(i) determining or having determined whether the tumor or the cancer cell expresses a marker (e.g., an mRNA or a protein) consistent with a Classical or Proneural subtype, e.g., expresses a marker consistent with the Classical or Proneural molecular subtypes of GBM, wherein optionally the marker consistent with a Classical or Proneural subtype comprises an EGFR, GLI1, NES, DLL3 or OLIG2 gene transcript or an EGFR, GLI1, NES, DLL3 or OLIG2 protein, or (ii) determining or having determined whether the tumor or the cancer cell expresses (e.g., expresses mRNA or protein) consistent with a Glut3 addicted gene/molecular signature, wherein optionally gene expression consistent with a Glut3 addicted gene signature comprises gene expression consistent with a high (a Glut3 addicted signature) or low (a Glut3 non-addicted signature) expression of at least one (one or more) of the genes, or 2, 3, 4, 5, 6, 7, 8, 9, 10, 11, 12, 13, 14, 15, 16, 17, 18, 19, 20, 21, 22, 23, 24, 25, 26, 27, 28, 29 or all 30 of the genes, as listed in FIG. 11 or FIG. 23, optionally one, several or all of the 314 genes in FIG. 11, or optionally one, several or all of the 15 genes in FIG. 23), (where the Glut3-addicted gene signature comprises having a Glut3 addicted marker expressed at high levels, and a Glut3 non-addicted marker expressed at low levels), wherein if a tumor or a cancer cell expresses both avb3+ and Glut3+ and is Glut-3 addicted, the tumor or the cancer cell will be sensitive to (will be substantially sensitive to) or will be successfully treated by (e.g., can be killed or induced to senescence by) the treatment targeting the integrin avb3 ($\alpha v \beta 3$) pathway, wherein optionally the tumor or cancer cell is a glioblastoma (GBM) tumor or cell, a melanoma tumor or melanoma cell or a primitive neuroectodermal tumor (PNET) or PNET cell.

In alternative embodiments, the treatment targeting the integrin avb3 ($\alpha v \beta 3$) pathway targets avb3, Glut3, PAK4, or YAP/TAZ.

In alternative embodiments, the treatment comprises administering or having administered to an individual in need thereof cilengitide (or, 2-[(2S,5R,8S,11S)-5-benzyl-11-{3-[(diaminomethylidene)amino]propyl}-7-methyl-3,6,9, 12,15-pentaoxo-8-(propan-2-yl)-1,4,7,10,13-pentaazacyclo-pentadecan-2-yl]acetic acid).

In alternative embodiments, the determining or having determined if the tumor or the cancer cell expresses both avb3+ and Glut3+ comprises determining if the tumor or the cancer cell expresses both an avb3+ and a Glut3+ protein, or both an avb3+ and a Glut3+ message (mRNA, transcript), or both an avb3+ and a Glut3+ protein and message, and optionally the determining or having determined if the tumor or the cancer cell expresses both an avb3+ and a Glut3+ protein is by a method comprising use of antibodies that specifically bind to a protein of the integrin avb3 pathway, optionally comprising an avb3, Glut3, PAK4, or YAP/TAZ binding antibody (an antibody that specifically binds avb3, Glut3, PAK4, or YAP/TAZ), and optionally the determining or having determined if the tumor or the cancer cell expresses both an avb3+ and a Glut3+ message (mRNA, transcript) is by a method comprising use of a polymerase chain reaction (PCR) (optionally comprising use of primers capable of amplifying an avb3+ and a Glut3+ message); or, gene expression profiling, an array, or a probe hybridization to a message, optionally a Northern blot (optionally comprising use of primers capable of specifically hybridizing to) an avb3+ and a Glut3+ message).

In alternative embodiments, the determining or having determined if the tumor or the cancer cell expresses a marker consistent with a Classical or Proneural subtype or expresses markers at levels consistent with the Glut3-addicted gene signature, e.g., as listed in FIG. 11 or FIG. 23, comprises determining or having determined if the tumor or the cancer cell expresses an mRNA and/or a protein consistent with a Classical or a Proneural subtype, or expresses an mRNA or protein markers consistent with the Glut3-addicted gene signature, e.g., expressed at levels as listed in FIG. 11 or FIG. 23, and optionally the determining or having determined if the tumor or the cancer cell expresses a protein consistent with a Classical or a Proneural subtype, or has a Glut3-addicted gene signature, e.g., is a high or a low expressed protein from a gene as listed in FIG. 11 or FIG. 23, is by a method comprising use of antibodies that specifically bind to a protein consistent with a Classical or a Proneural subtype, or a protein from a gene associated with Glut3 addiction, e.g., as listed in FIG. 11 or FIG. 23, and optionally the determining or having determined if the tumor or the cancer cell expresses a message (mRNA, transcript) consistent with a Classical or a Proneural subtype, or expresses markers consistent with the Glut3-addicted gene signature, e.g., as listed in FIG. 11 or FIG. 23, is by a method comprising use of a polymerase chain reaction (PCR) (optionally comprising use of primers capable of amplifying a message (mRNA, transcript) consistent with a Classical or a Proneural subtype, or markers consistent with the Glut3-addicted gene signature, e.g., as listed in FIG. 11 or FIG. 23); or, by gene expression profiling, optionally by using an array, or optionally by using a probe hybridization to a message of interest, optionally a Northern blot (optionally comprising use of primers capable of specifically hybridizing to) a message (mRNA, transcript) consistent with a Classical or a Proneural subtype, or markers consistent with the Glut3-addicted gene signature, e.g., as listed in FIG. 11 or FIG. 23.

In alternative embodiments, the determining or having determined if the tumor or the cancer cell expresses both avb3+ and Glut3+ comprises taking or isolating a cell or a sample of cells, optionally cancer cells or tumors cells, from a patient, optionally a patient tentatively diagnosed or definitely diagnosed with the tumor or cancer, optionally GBM, and determining if the cell or sample of cells expresses both avb3+ and Glut3+ and is Glut-3 addicted.

In alternative embodiments, provided are methods for treating or ameliorating, or killing, or inducing into senescence, a tumor or a cancer cell in a patient or ex vivo, wherein optionally the tumor or cancer cell is a glioblastoma (GBM) tumor or a GBM cancer cell, or a melanoma or a primitive neuroectodermal tumor (PNET), or treating or ameliorating a tumor or cancer, optionally GBM, a melanoma or a primitive neuroectodermal tumor (PNET), in an individual in need thereof, comprising:

(a) determining or having determined whether the tumor or cancer, optionally a glioblastoma (GBM) tumor or a GBM cancer cell, will be sensitive to a treatment targeting the integrin avb3 ($\alpha v\beta 3$) pathway using a method as provided herein, and (b) if the method of step (a) determines, or has had determined, that the tumor or cancer, optionally a glioblastoma (GBM) tumor or a GBM cancer cell, will be sensitive to a treatment targeting the integrin avb3 ($\alpha v\beta 3$) pathway, administering or having administered the treatment targeting the integrin avb3 ($\alpha v\beta 3$) pathway to an individual in need thereof, or, administering or having administered the treatment to the tumor or cancer cell, optionally to a glioblastoma (GBM) tumor or GBM cancer cell, if the tumor or cancer cell is derived from or isolated from the individual in need thereof, or if the tumor or cancer cell is determined to be sensitive to a treatment targeting the integrin avb3 ($\alpha v\beta 3$) pathway using a method as provided herein (e.g., if the glioblastoma (GBM) tumor or the GBM cancer cell is found to express both avb3+ and Glut3+ and is Glut-3 addicted).

In alternative embodiments, the treatment targets avb3, Glut3, PAK4, or YAP/TAZ, or the treatment comprises administering or having administered to an individual in need thereof cilengitide (or, 2-[(2S,5R,8S,11S)-5-benzyl-11-{3-[(diaminomethylidene)amino]propyl}-7-methyl-3,6,9,12,15-pentaoxo-8-(propan-2-yl)-1,4,7,10,13-pentaazacyclopentadecan-2-yl]acetic acid).

The details of one or more exemplary embodiments are set forth in the accompanying drawings and the description below. Other features, objects, and advantages of the invention will be apparent from the description and drawings, and from the claims. All publications, patents, patent applications cited herein are hereby expressly incorporated by reference for all purposes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings set forth herein are illustrative of embodiments as provided herein and are not meant to limit the scope of the invention as encompassed by the claims.

FIG. 1A graphically illustrates data of a hierarchical cluster that stratifies patients into two groups according to median survival, and by correlating gene expression with GBM patient survival, identifies a $\beta 3^{high}$ subset of samples within the shorter-survival group;

FIG. 1B graphically illustrates data showing the probability of survival of GBM patients as a function of days in GBM populations which express high and low levels of $\beta 3$;

FIG. 1C and FIG. 8A-C illustrate tables showing genes involved in glucose metabolism (ALDOC, PFKM and GLUT3); and FIG. 1D graphically illustrates data from a Kaplan-Meier analysis indicating that poor survival correlates with high expression of GLUT3 and low expression of ALDOC and PFKM, as discussed in detail in Example 1, below.

FIG. 2A illustrates images of immunoblots, and graphically illustrates data, showing the expression of indicated proteins for U87MG, LN229 and LN18 GBM cells infected by shRNA Control (Ctrl) or sh$\beta 3$, graph shows the fold change of protein expression determined by densitometry analysis;

FIG. 2I graphically illustrates data showing the fold change of $\beta$-galactosidase positive cells versus the total cell number, Inverted microscopy images of acidic senescence-associated $\beta$-galactosidase staining in U87MG shCtrl and U87MG $\beta 3$ and Glut3 shRNA (n=5 fields counted per group);

FIG. 2J graphically illustrates data of a cell-cycle analysis showing the percentage of cells in G0/G1, S, and G2/M in U87MG cells with $3 and Glut3 knockdown;

FIG. 2K illustrates images show acidic senescence-associated $\beta$-galactosidase staining, a marker of senescence, in mice implanted with U87MG shCtrl, sh$\beta 3$, shGlut3, or sh$\beta 3$ with ectopic expression of Glut3;

as discussed in detail in Example 1, below.

Figures 3A, 3B:
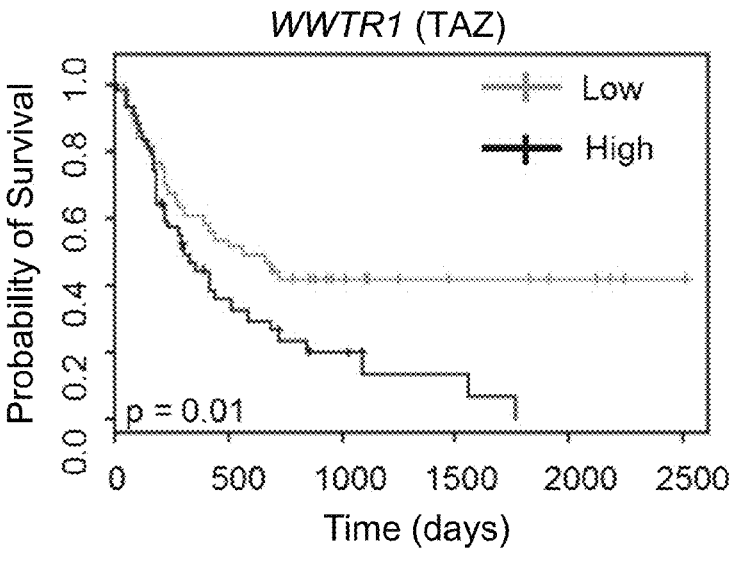
Figure 3C:
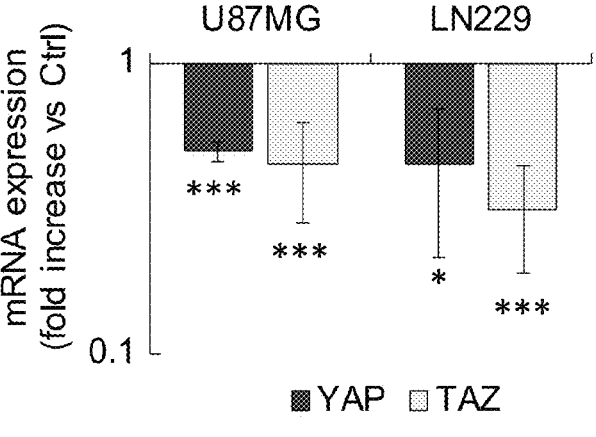
Figure 3D:
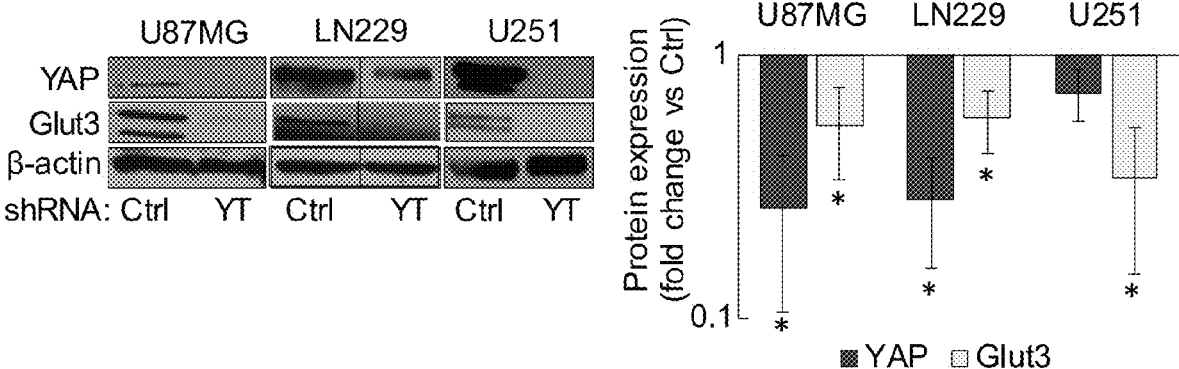
Figure 3E:
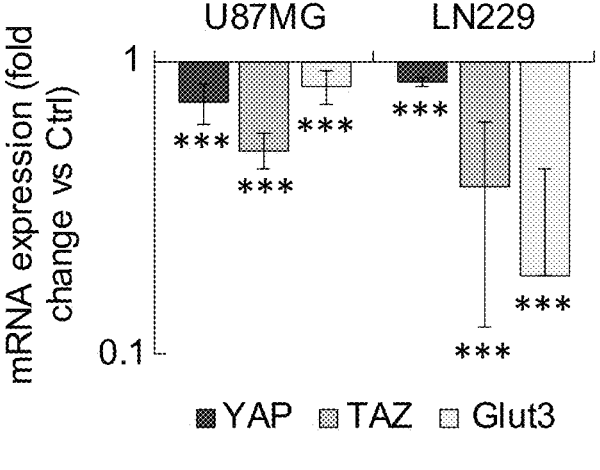
Figure 3F:
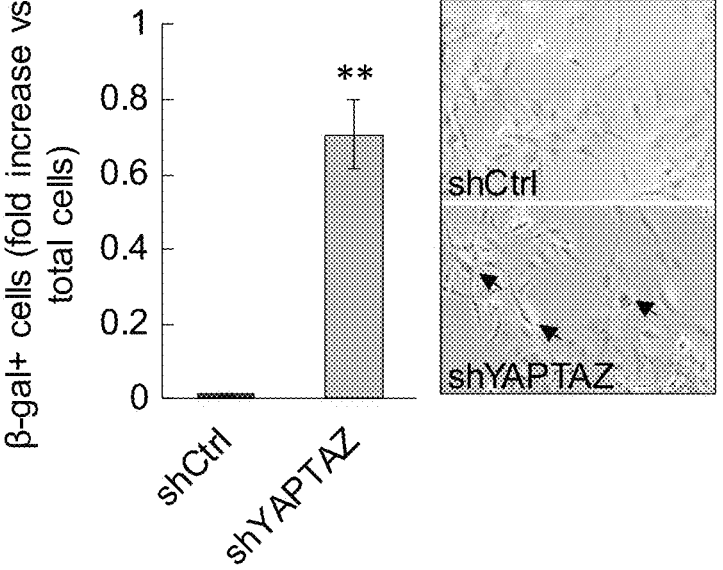
Figure 3G:
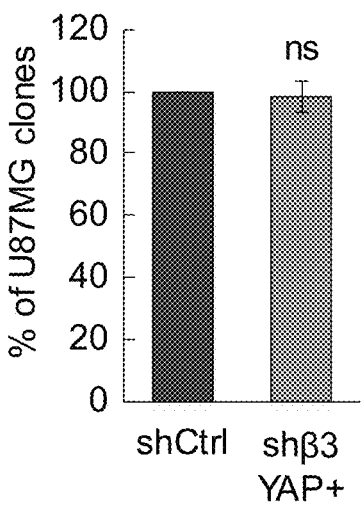
Figure 3H:
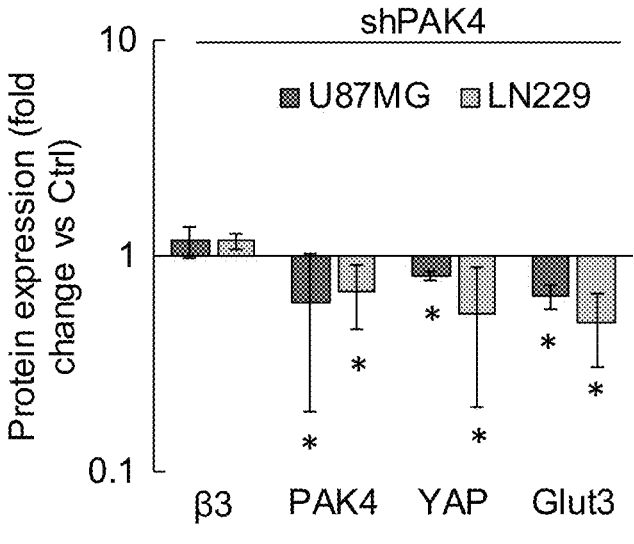
Figure 3I:
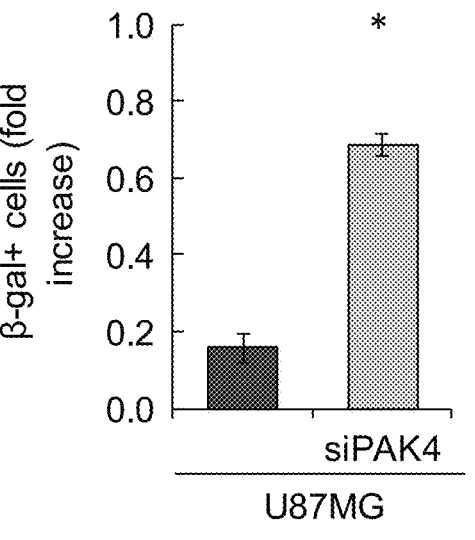
Figure 3J:
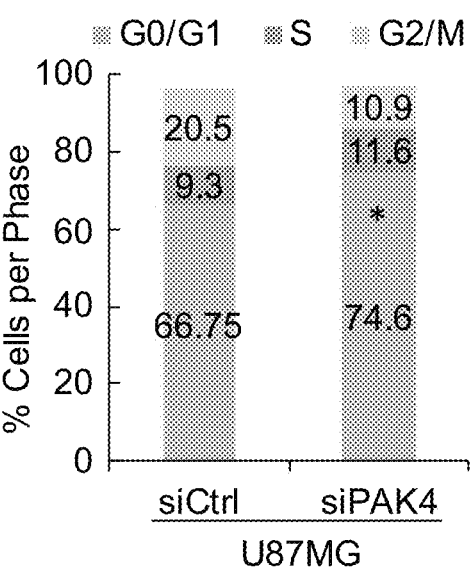

FIG. 3A-J: 33 modulates Glut3 expression through PAK4-YAP/TAZ axis:

FIG. 3A graphically illustrates data of a Kaplan-Meier analysis of a Freije dataset for TAZ expression (n=42 for $3 low and n=43 for β3 high; P=0.03);

FIG. 3B illustrates immunoblots showing the effect of β3 knockdown on protein expression of YAP and β3; bars represent the fold change of protein expression determined by densitometry analysis;

FIG. 3C graphically illustrates data showing the effect of β3 knockdown on mRNA expression of YAP and TAZ determined by qRT-PCR, displayed as fold change for gene expression normalized to sh-control in U87MG (n=3), LN229 (n=3) and U251 (n=2);

FIG. 3D illustrates immunoblots showing the effect of YAP/TAZ knockdown on Glut3 protein expression, and the graph shows the fold increase determined by densitometry analysis. U87MG (n=3), LN229 (n=3) and U251 (n=2);

FIG. 3E graphically illustrates data showing the effect of YAP/TAZ knockdown on mRNA expression for Glut3, YAP and TAZ determined by qRT-PCR, displayed as fold change of gene expression normalized to sh-control;

FIG. 3F graphically illustrates data showing acidic senescence-associated β-galactosidase staining in U87MG shCtrl versus YAP/TAZ shRNA;

FIG. 3G graphically illustrates data showing the effect of ectopic expression of YAP on U87MG β3 shRNA on anchorage-independent growth;

FIG. 3H graphically illustrates data showing the fold change of protein expression in U87MG (n=2) and LN229 (n=2) determined by densitometry analysis;

FIG. 3I graphically illustrates data showing acidic senescence-associated β-galactosidase staining in U87MG shCtrl and PAK4 siRNA (n=3); and FIG. 3J graphically illustrates data of a Cell-cycle analysis showing the percentage of cells in G0/G1, S, and G2/M in U87MG cells with PAK4 siRNA (n=3); as discussed in detail in Example 1, below.

Figure 4A:
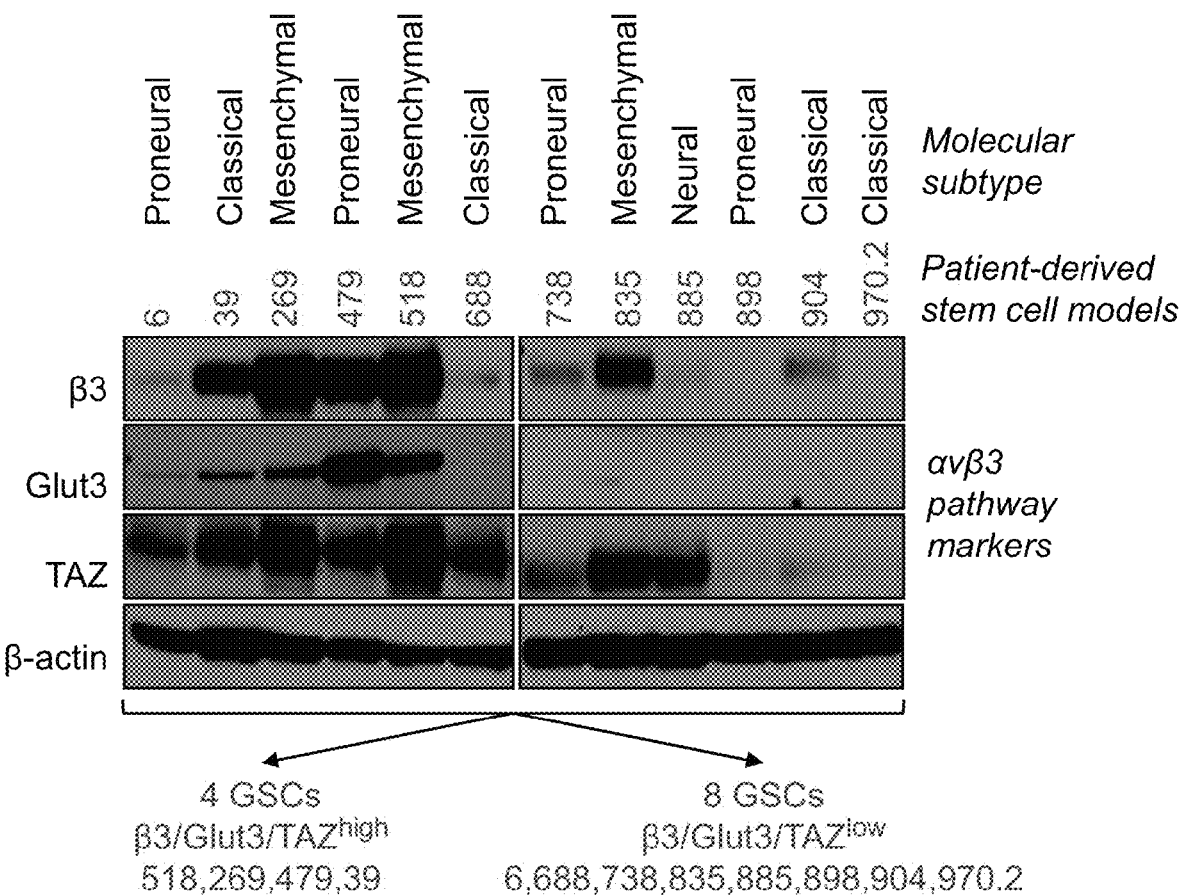
Figure 4C:
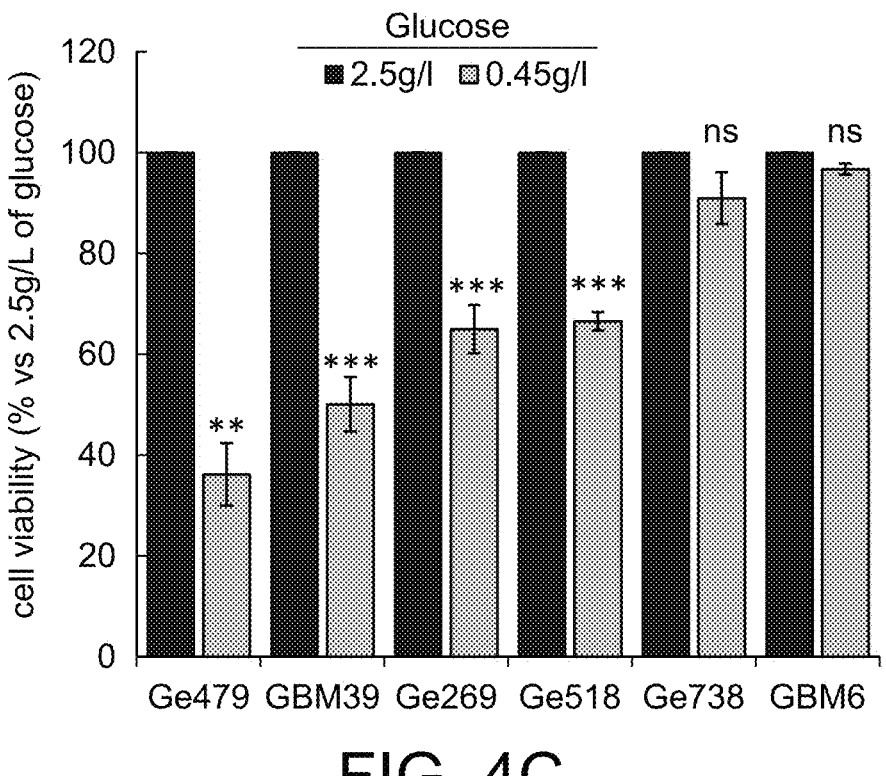
Figure 4D:
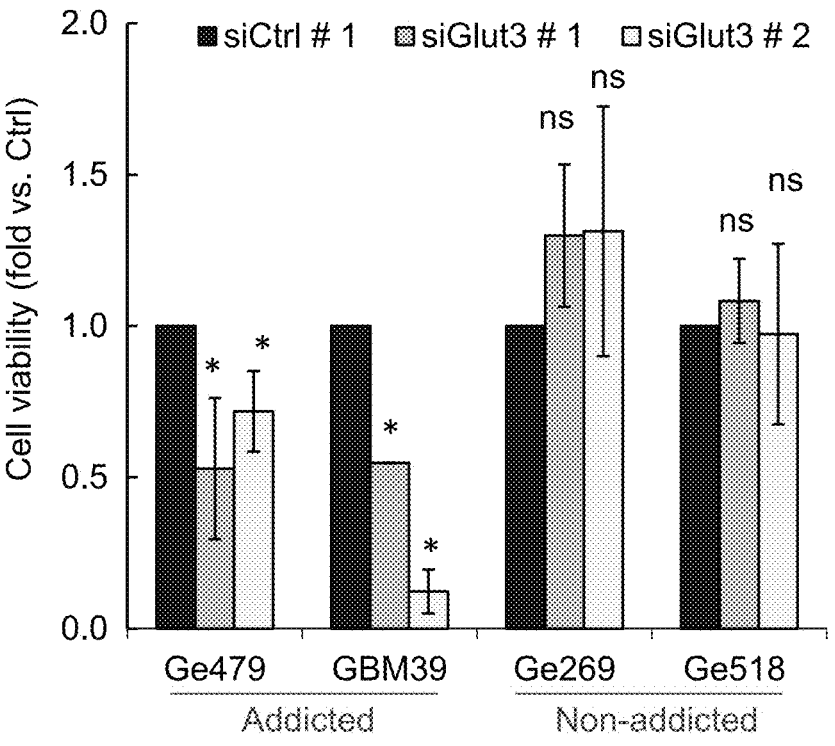
Figure 4E:
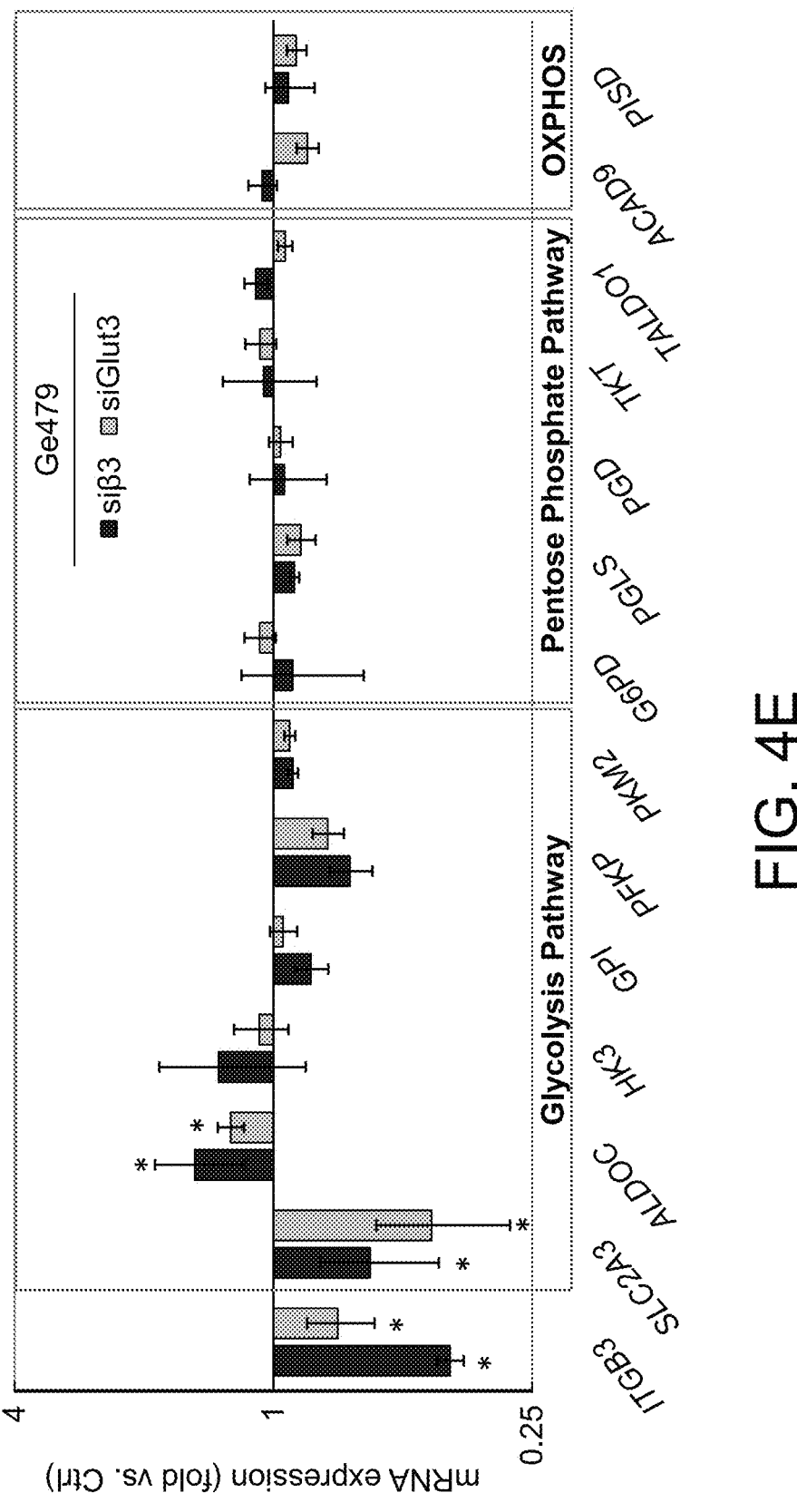

FIG. 4A-E: Integrin αvβ3 is required for Glut3 expression in patient-derived gliomaspheres that show heterogeneity in Glut3 "addiction":

FIG. 4A illustrates representative immunoblots showing expression of β3, Glut3, and TAZ in GSCs with a schematic representing the decision tree for selecting GSCs based on β3/Glut3 expression (n=2);

FIG. 4B illustrates immunoblots (upper image) showing the effect of β3 knockdown on expression of indicated proteins in Ge479 (n=3), and a graph (lower image) showing data representing the fold change of protein expression relative to sh-control determined by densitometry analysis;

FIG. 4C graphically illustrates data showing the effect of glucose concentration on cell viability measured by CELL-TITER-GLO™ (CellTiter-Glo) in GSCs (n=3-5);

FIG. 4D graphically illustrates data showing the effect of Glut3 knockdown on cell viability measured by CELLTI-TER-GLO™ in GSCs (n=3-4); and, FIG. 4E graphically illustrates data showing the expression of glycolytic, pentose phosphate and mitochondrial oxidative phosphorylation (OXPHOS) related genes, which were determined by qRT-PCR after β3 or Glut3 knockdown in Ge479, Bars show the fold change of gene expression normalized to sh-control;

as discussed in detail in Example 1, below.

Figure 5D:
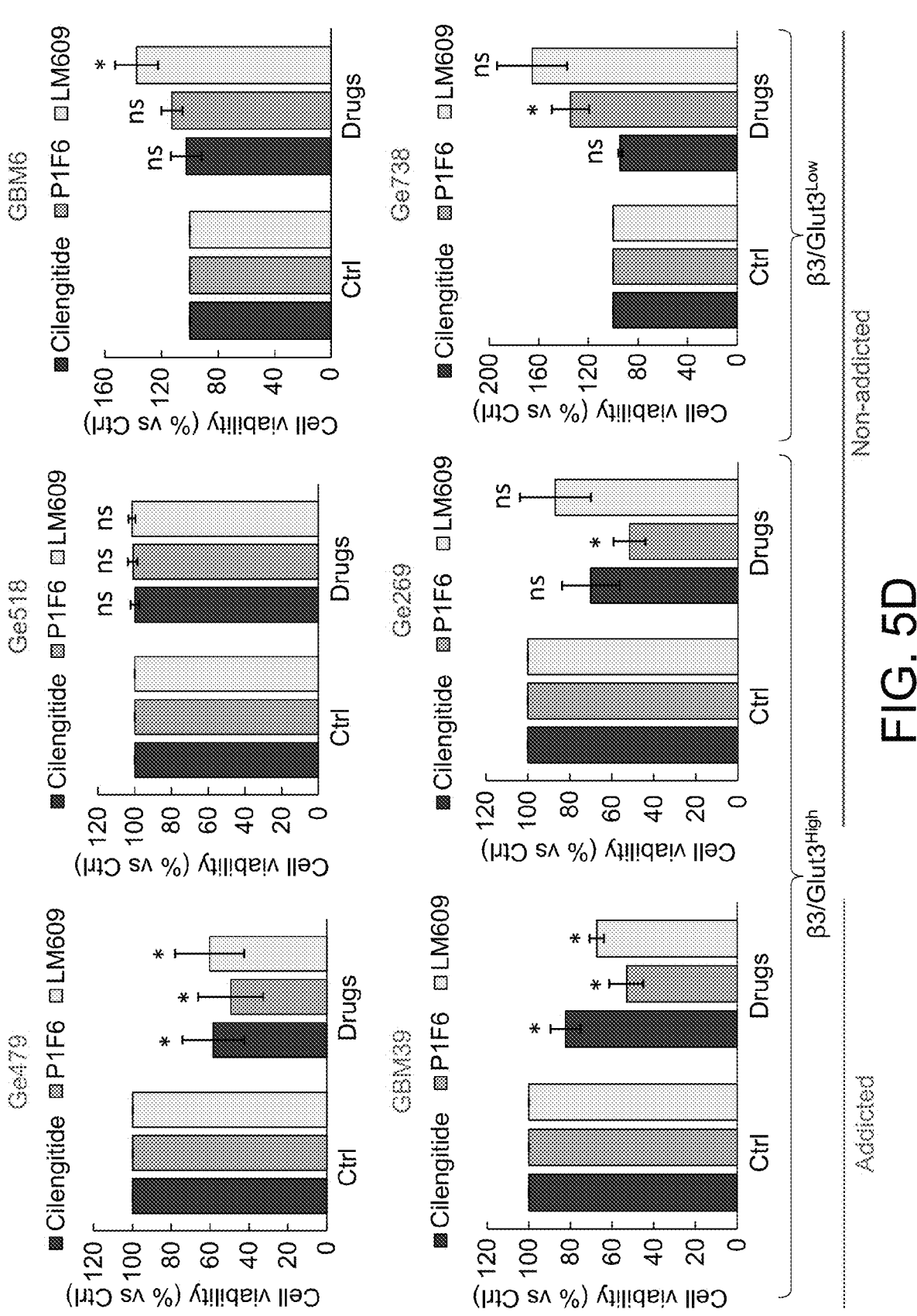
Figure 5E:
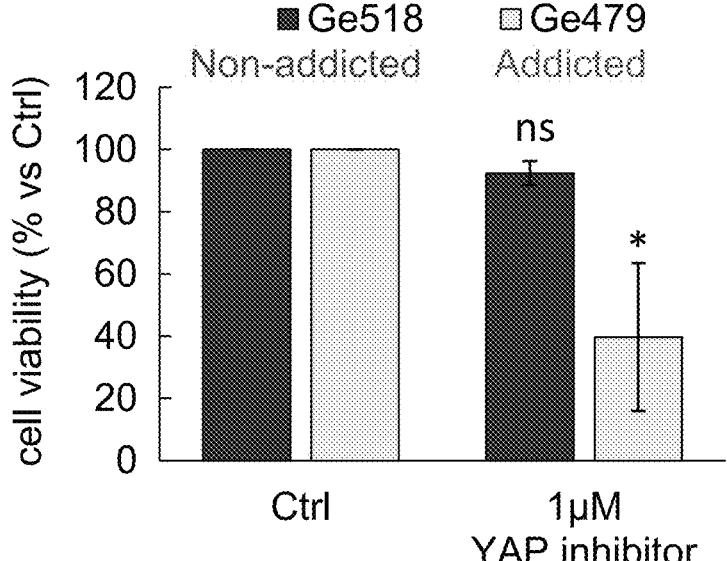
Figure 5F:
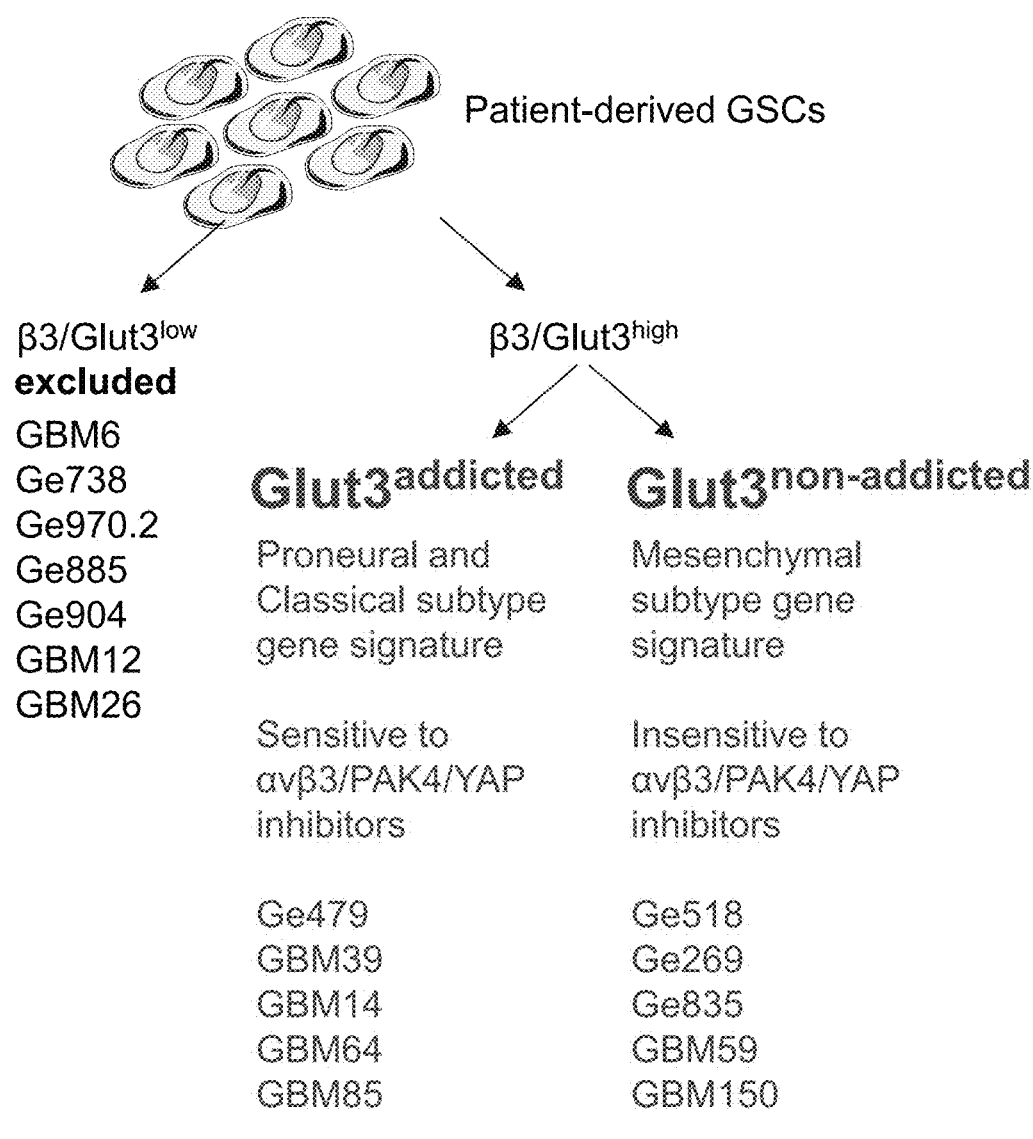
Figure 5G:
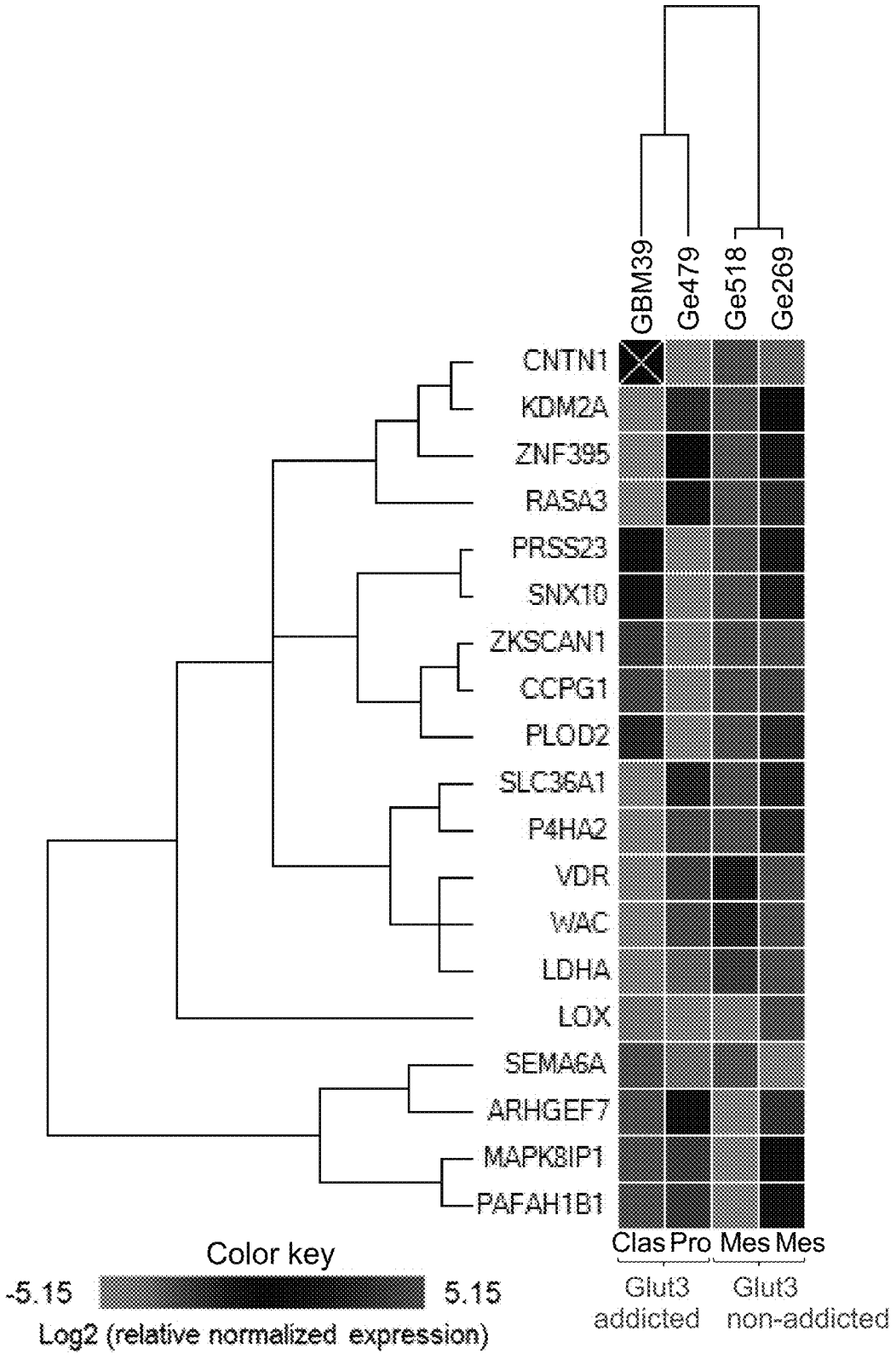
Figure 5H:
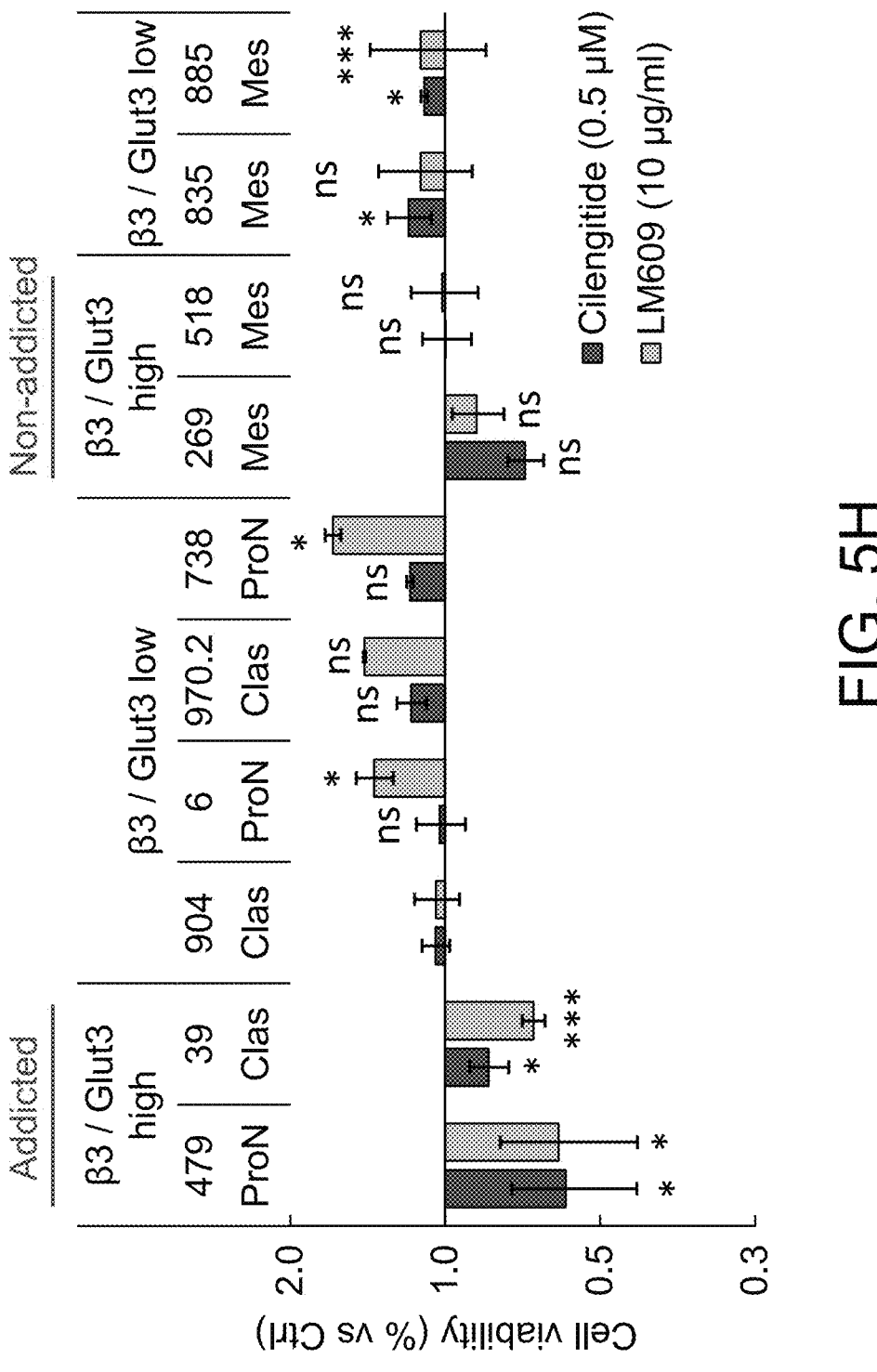
Figure 5I:
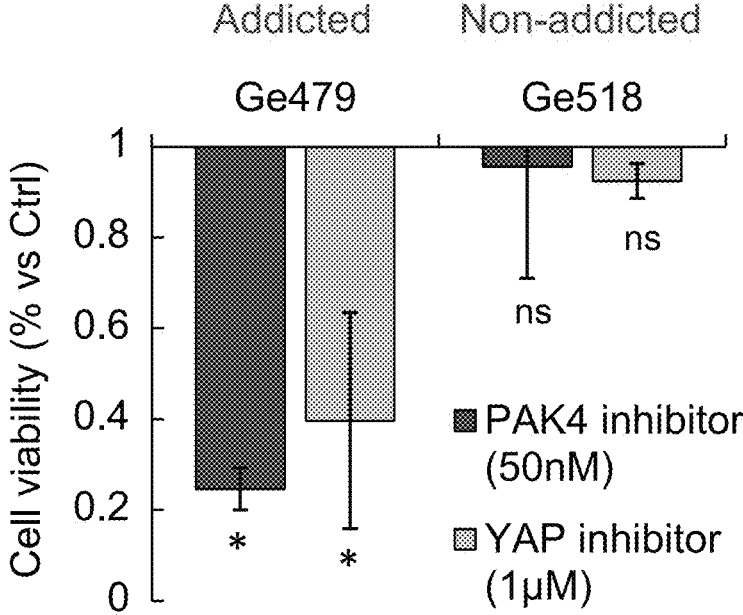

FIG. 5A-I: The mesenchymal subtype of GBM is enriched for genes involved in glycolytic pathway and sensitive to αvβ3 antagonists, YAP and PAK4 inhibitors:

FIG. 5A graphically illustrates data showing an enrichment analysis of glycolytic genes for the Freije dataset;

FIG. 5B graphically illustrates a Kaplan-Meier analysis of Freije dataset for PGK1 expression;

FIG. 5C graphically illustrates an enrichment analysis for β3, Glut3 (also found in FIG. 5A), YAP and TAZ;

FIG. 5D graphically illustrates the effect of LM609 (αvβ3 function blocking antibody) and cilengitide (cyclic peptide antagonist of av integrins including αvβ3 and αvβ5) on cell viability measured by CELLTITER-GLO™ in GSCs;

FIG. 5E graphically illustrates the effect of YAP inhibitor (verteporfin) or PAK4 inhibitor (PF-03758309, CAS no. 898044-15-0) on cell viability measured by CELLTITER-GLO™ in GSCs;

FIG. 5F schematically illustrates an exemplary model of Glut3 addiction in GBM;

FIG. 5G schematically illustrates data identifying Glut3 addicted vs. Glut3 non-addicted samples using 96 signature genes. mRNA was determined by qRT-PCR (n=2) and Bio-Rad software has been used for analysis;

FIG. 5H graphically illustrates the effect of LM609 (αvβ3 function blocking antibody) and cilengitide (cyclic peptide antagonist of av integrins including αvβ3 and αvβ5) on cell viability measured by CELLTITER-GLO™ in GSCs (n=3-5); and, FIG. 5I graphically illustrates the effect of YAP inhibitor (verteporfin) or PAK4 inhibitor (PF-03758309) on cell viability measured by CELLTITER-GLO™ in GSCs (n=3-5);

as discussed in detail in Example 1, below.

Figure 6:
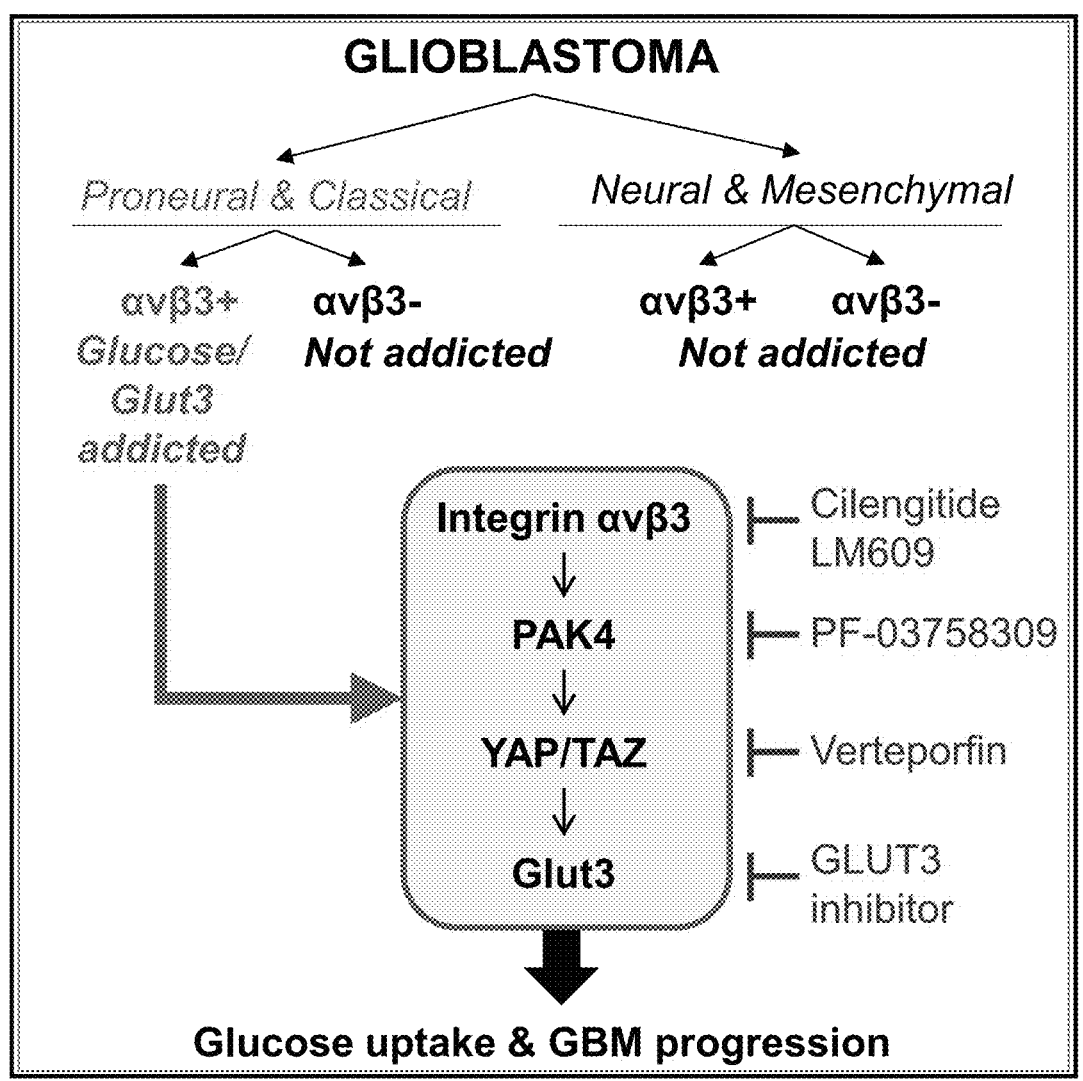
Figure 12A:
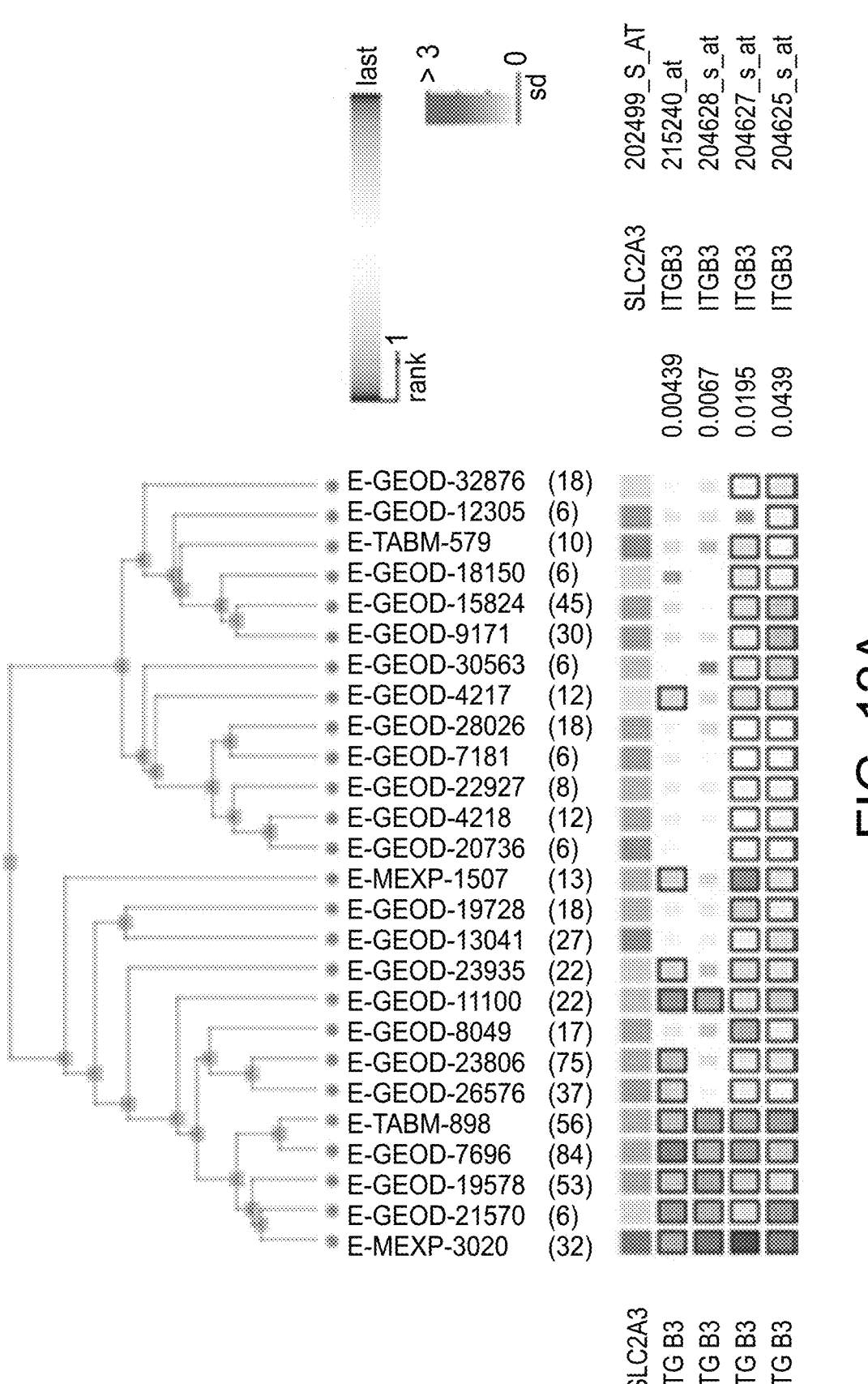
Figure 12B:
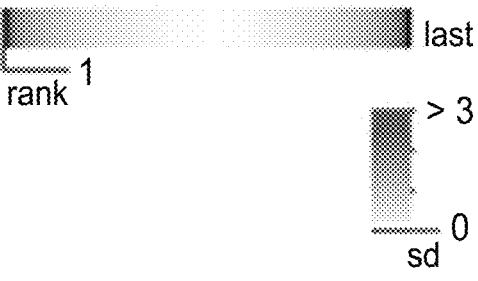
Figure 12C:
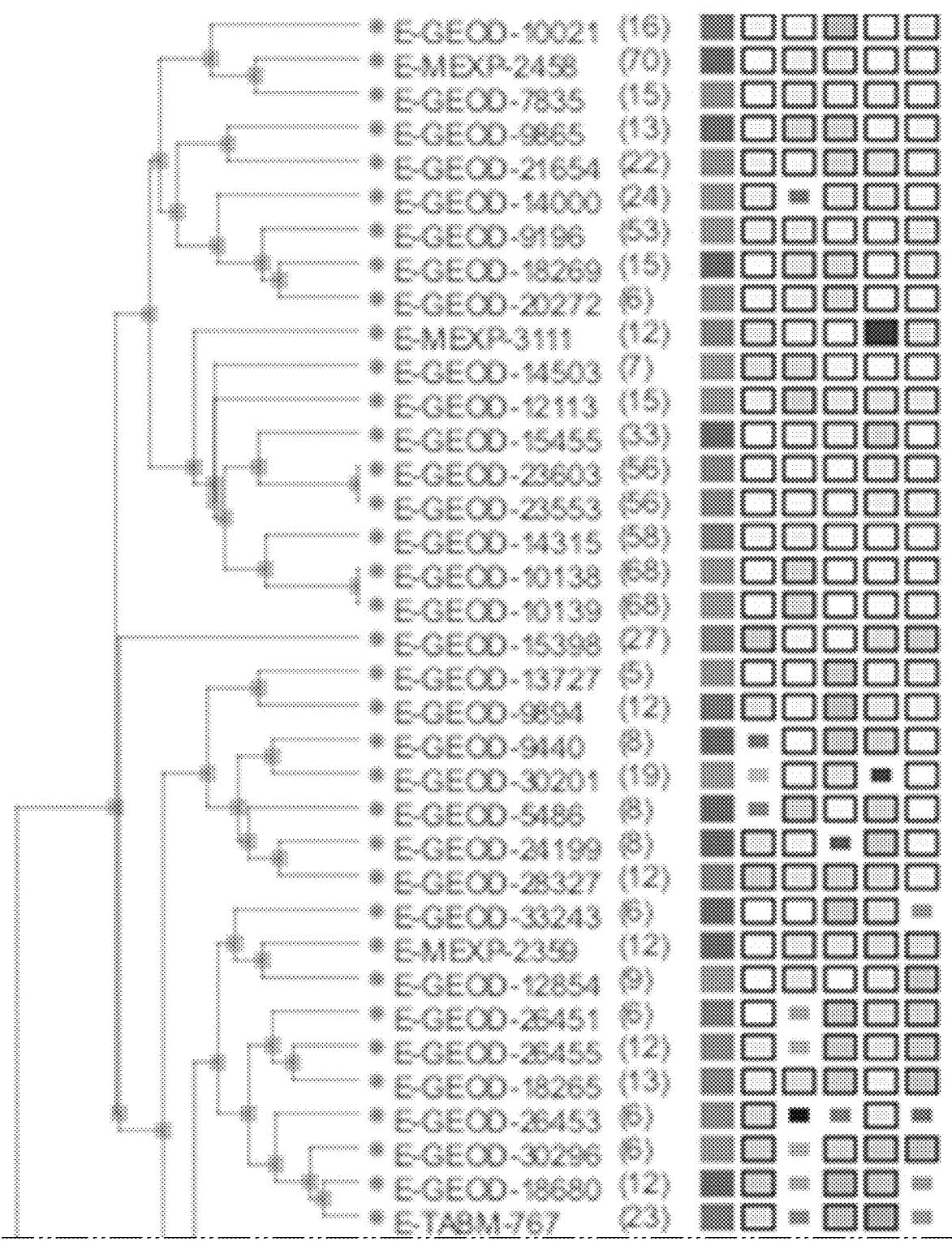
Figure 12D:
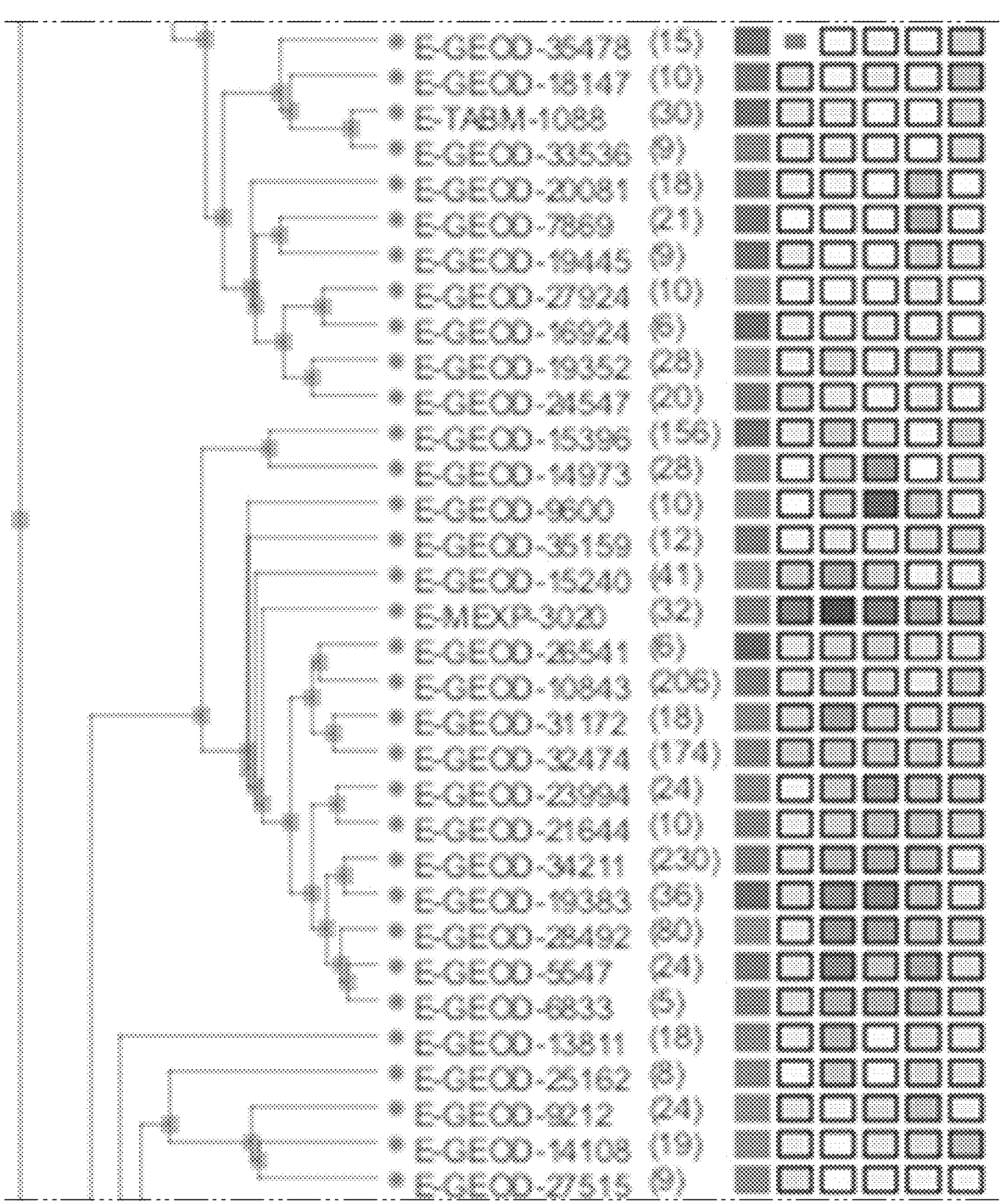
Figure 12E:
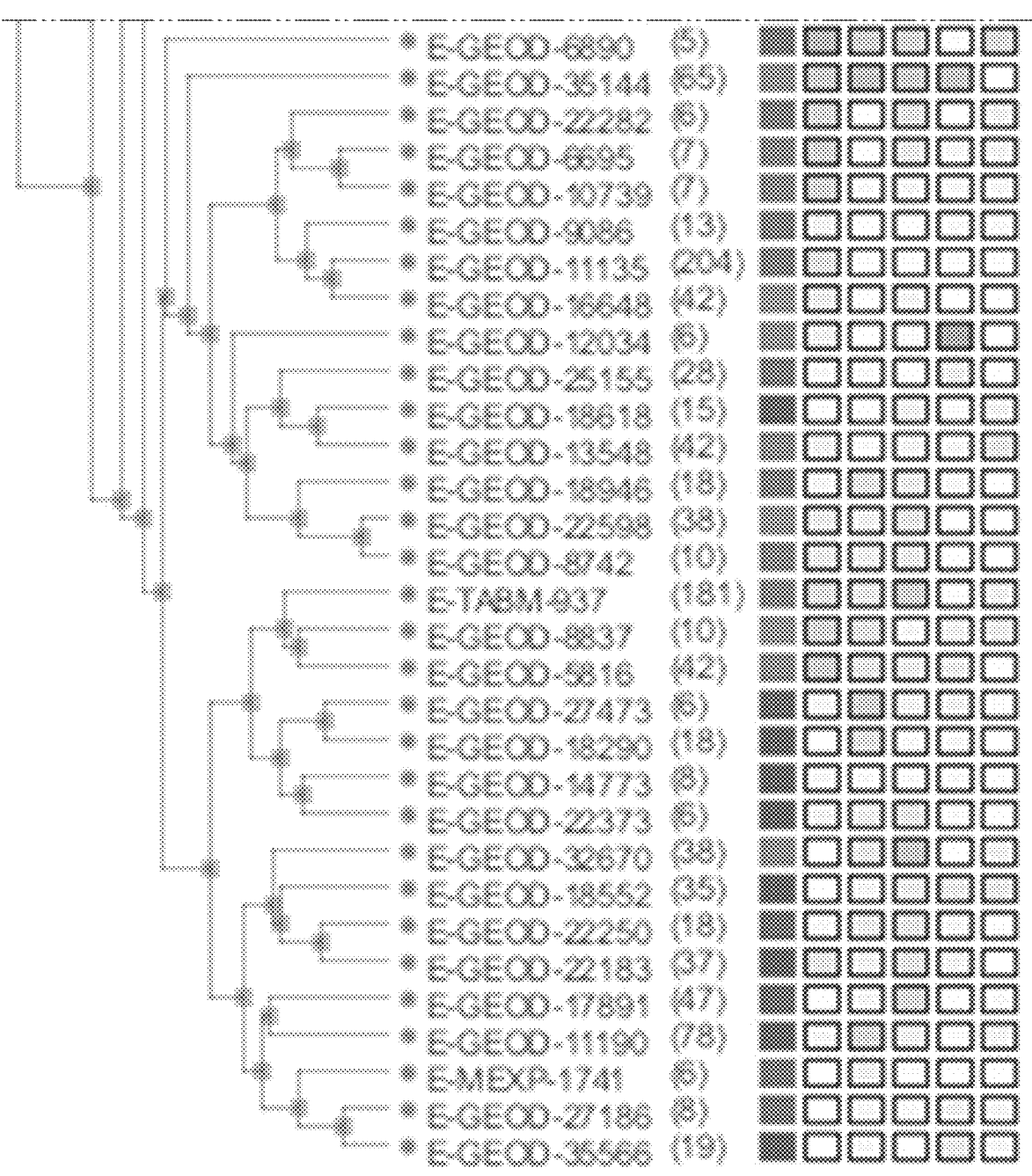

FIG. 6 illustrates a schematic depicting an exemplary model of Glut3 addiction in GBM; as discussed in detail in Example 1, below.

FIG. 7 illustrates a table summarizing pValues from Kaplan-Meier curves generated from datasets confirm ITGB3 as a strong prognostic factor associated with poor GBM patient survival, as discussed in detail in Example 1, below.

FIGS. 8A-C and FIG. 11 illustrate tables showing genes involved in glucose metabolism (ALDOC, PFKM and GLUT3), as discussed in detail in Example 1, below.

FIG. 9 illustrates a table summarizing data from Kaplan-Meier curves from the "Lee" and "TCGA" datasets: whereas ALDOC and PFKM do not consistently correlate with patient outcome, GLUT3 expression tracks with poor survival for all datasets, as discussed in detail in Example 1, below.

FIG. 10A-E illustrates a table showing a list of primers used for qRT-PCR, as discussed in detail in Example 1, below.

FIG. 11A-D illustrates a table showing list of genes defining Glut3 addicted vs non-addicted signature, as discussed in detail in Example 1, below; bioinformatics software was used to perform differential gene expression analysis on GBM samples from the "Freije" dataset. The Glut3 non-addicted signature includes genes that were expressed at significantly higher levels in Glut3-positive GBM samples from patients with longer (i.e., higher than median) survival compared with GBM samples from patients with shorter survival. Similarly, the Glut addicted signature includes genes that were expressed at a significantly higher level in Glut3-positive GBM samples from patients with shorter survival.

FIG. 12A-E schematically illustrate data from the analysis of multiple datasets revealing that ITGB3 (B3) and GLUT3 as co-expressed genes not only in GBM, but also in other cancer types, as discussed in detail in Example 1, below.

Figure 13B:
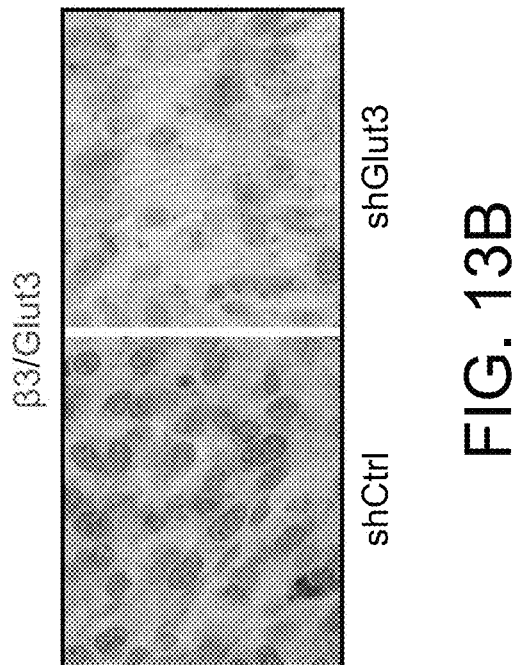
Figure 13A:
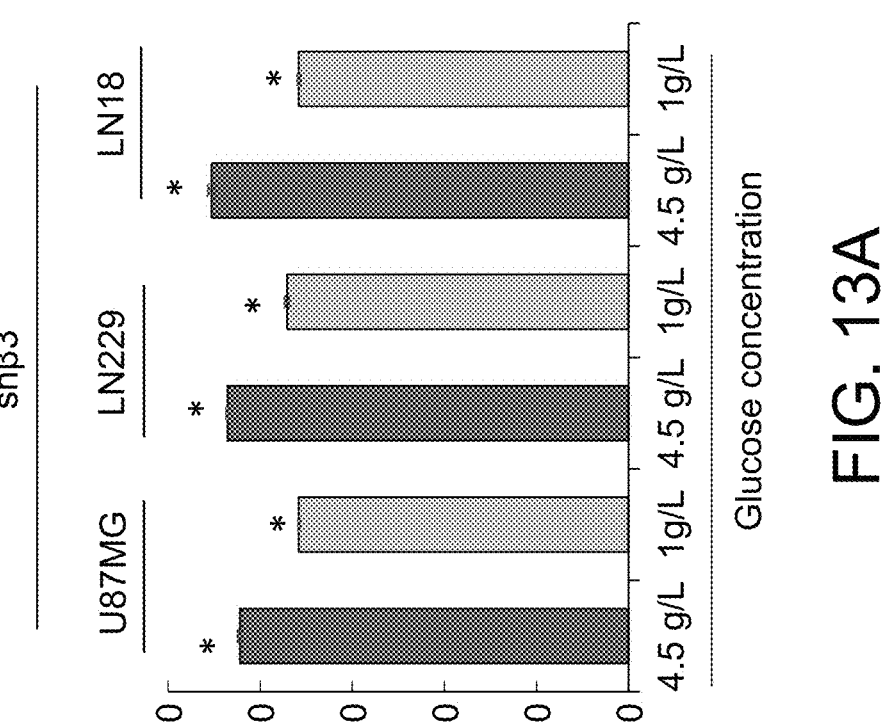
Figure 13D:
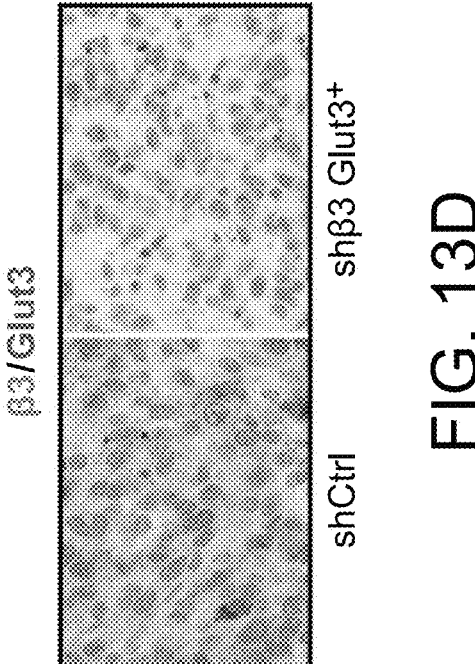
Figure 13C:
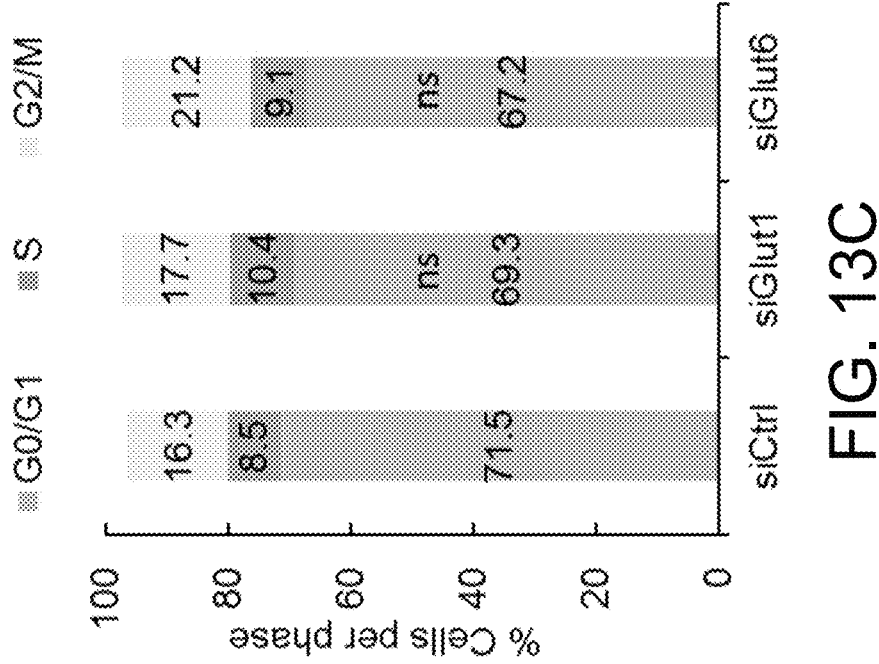
Figure 13H:
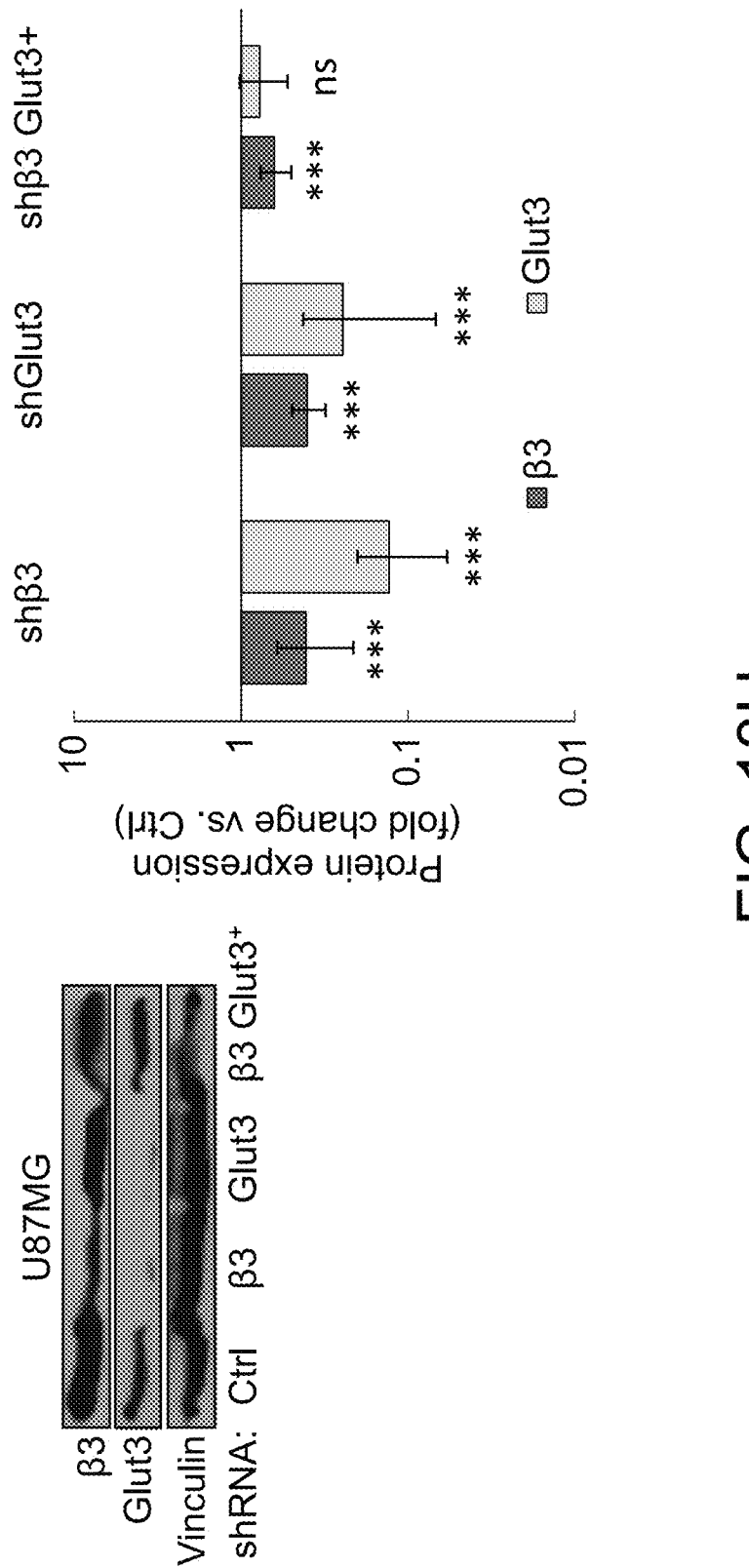

FIG. 13A-H: The impact of integrin αvβ3 on GBM is attributed to its regulation of Glut3 expression:

FIG. 13A graphically illustrates the effect of a β3 knockdown on U87MG, LN229 and LN18 cell viability in high (4.5 µg/L) vs low (1 µg/L) glucose measured by Alamar blue;

FIG. 13B illustrates a histological analysis of U87MG cells with shCtrl and shGlut3; tumors were stained for haematoxylin and eosin (H&E), β3 and Glut3;

FIG. 13C graphically illustrates a cell cycle analysis showing the percentage of cells in G0/G1, S, and G2/M for U87MG cells with knockdown of Glut1 or Glut;

FIG. 13D illustrates a histological analysis of U87MG with shCtrl or β3 shRNA along with ectopic expression of Glut3 (Glut3+), tumors were stained for haematoxylin and eosin (H&E), β3 and Glut3;

FIG. 13E graphically illustrates data showing the fold change of β-galactosidase positive cells versus the total cell number. Inverted microscopy images of acidic senescence-associated β-galactosidase staining in LN229 and LN18 Ctrl, 33 and Glut3 siRNA (n=5 fields counted per group);

FIG. 13F graphically illustrates a cell-cycle analysis showing the percentage of cells in G0/G1, S, and G2/M in LN229 and U251 cells with β3 and Glut3 knockdown;

FIG. 13G graphically illustrates a flow cytometry analysis used to quantify γH2AX expression in LN229 cells with β3 and Glut3 knockdown. The graph shows the fold increase of γH2AX expression (n=2); and FIG. 13H illustrates immunoblots (left image) show expression of 33 and Glut3 in U87MG with shCtrl, shGlut3 or β3 shRNA along with ectopic expression of Glut3 (Glut3+) (n=3-4), and graphically illustrates (right image) the fold change determined by densitometry analysis;

as discussed in detail in Example 1, below.

Figures 14A, 14B, 14C:
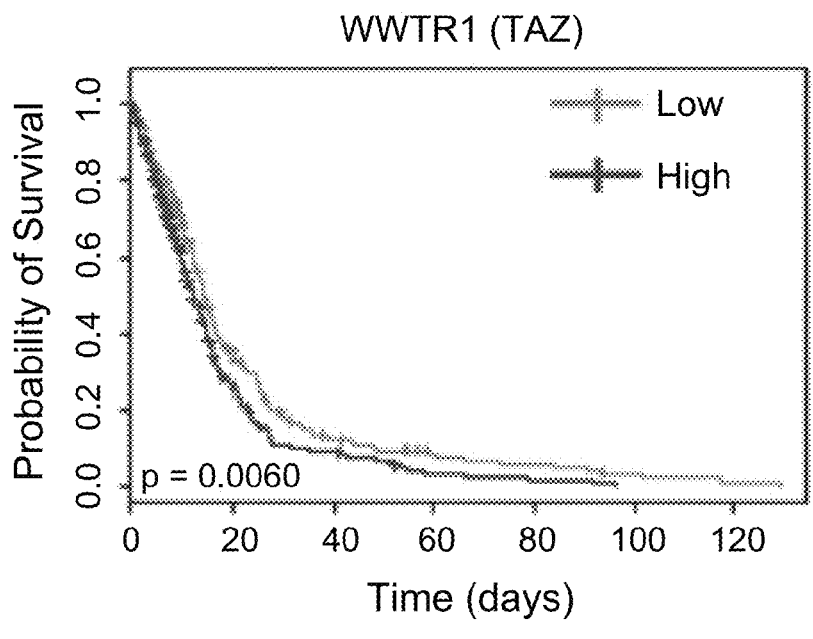
Figure 14D:
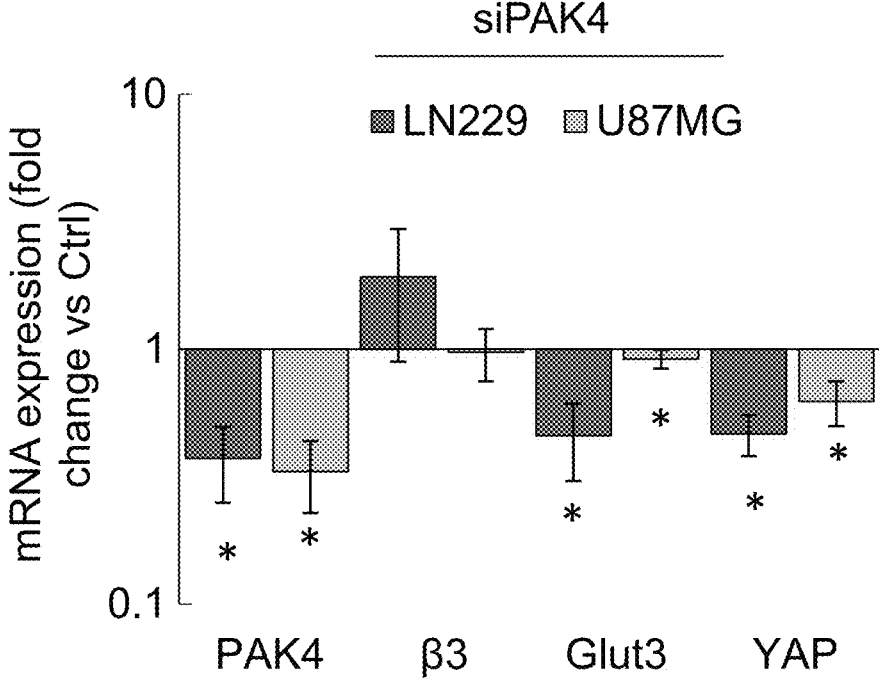
Figure 14E:
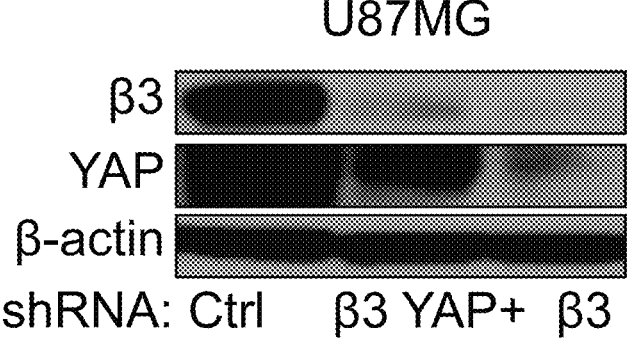
Figure 14F:
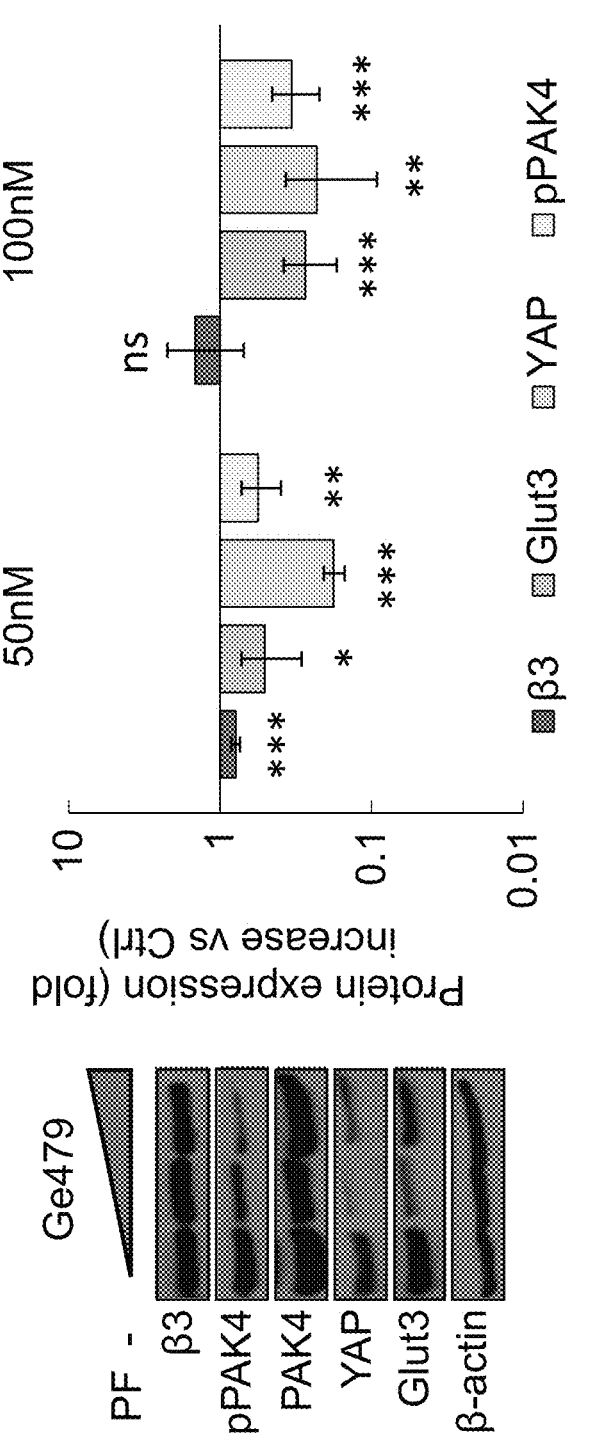
Figure 14G:
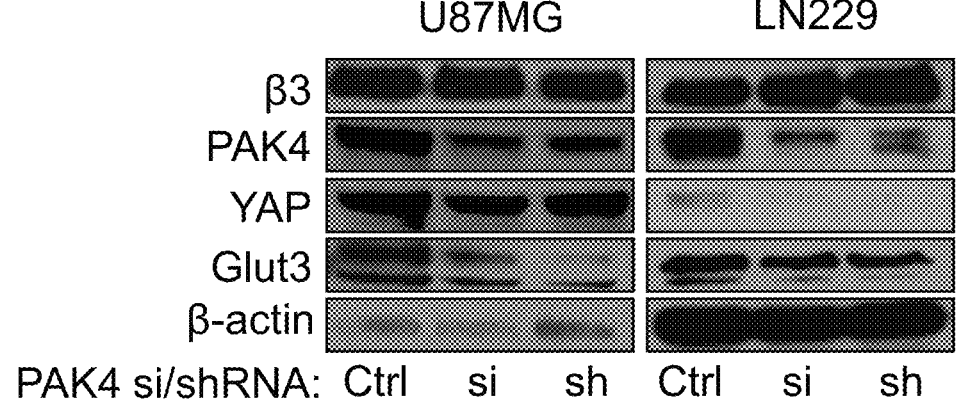

FIG. 14A-G: TAZ expression is correlated with poor survival and effect of YAP and PAK4 inhibitors:

FIG. 14A graphically illustrates a Kaplan-Meier analysis of TCGA dataset for WWTR1 (TAZ) expression;

FIG. 14B graphically illustrates data showing the effect of YAP inhibitor, Verteporfin on its target genes (CTGF and CYR61). Expression of CTGF, CYR61 and Glut3 were determined by qRT-PCR in LN229 (n=3) and U87MG (n=2); graph shows the fold change for gene expression normalized to control;

FIG. 14C illustrates immunoblots showing the effect of PAK4 inhibitor, PF-03758309 on the phosphorylation of PAK4 (pPAK4); representative immunoblots show effect of PF-03758309 on expression of indicated proteins in U87MG (n=2);

FIG. 14D graphically illustrates that genetic knockdown of PAK4 reduces expression of Glut3 and YAP, but not integrin β3 for the LN229 and U87MG GBM cell lines;

FIG. 14E illustrates representative immunoblots showing the expression of 3 and YAP in U87MG with shCtrl, shβ3, and shβ3 along with ectopic expression of YAP (YAP+) (n=2);

FIG. 14F illustrates the effect of PAK4 inhibitor PF-03758309 on the phosphorylation of PAK4 (pPAK4): left image illustrates representative immunoblots showing the effect of PF-03758309 on expression of indicated proteins in Ge479 (n=2-3), and right image graphically presents this data; and FIG. 14G illustrates immunoblots showing the effect of PAK4 knock down on indicated proteins in U87MG (n=2) and LN229 (n=2);

as discussed in detail in Example 1, below.

Figures 15A, 15B:
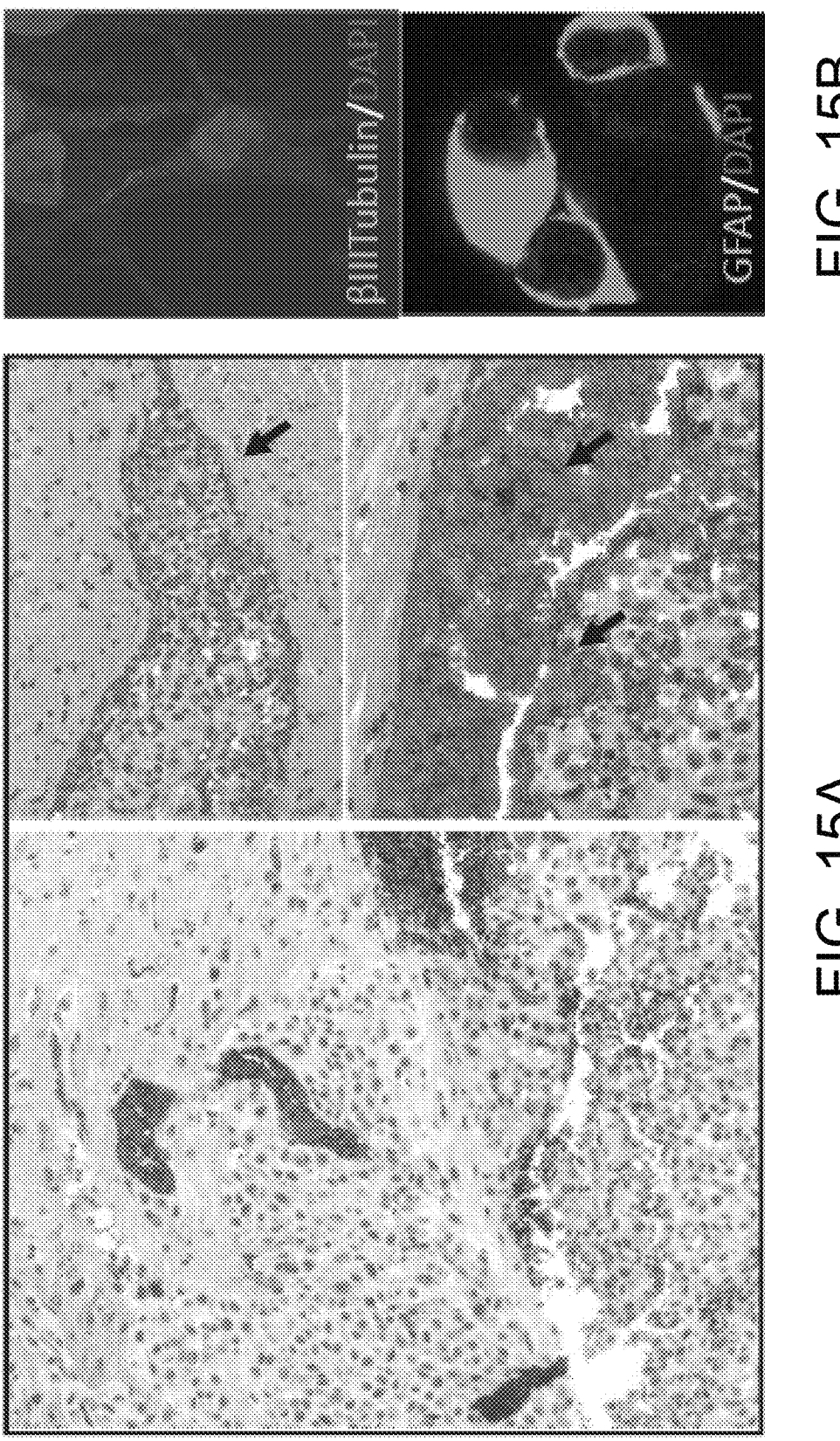

FIG. 15A-J illustrate: GSCs are tumorigenic and multipotent:

FIG. 15A illustrates representative light micrograph images showing H&E staining for Ge518 GSCs-derived tumor in immune-compromised mice (n=3). GSCs show invasive phenotype (right panel, top) and necrotic foci (right panel, bottom).

Figure 15C:
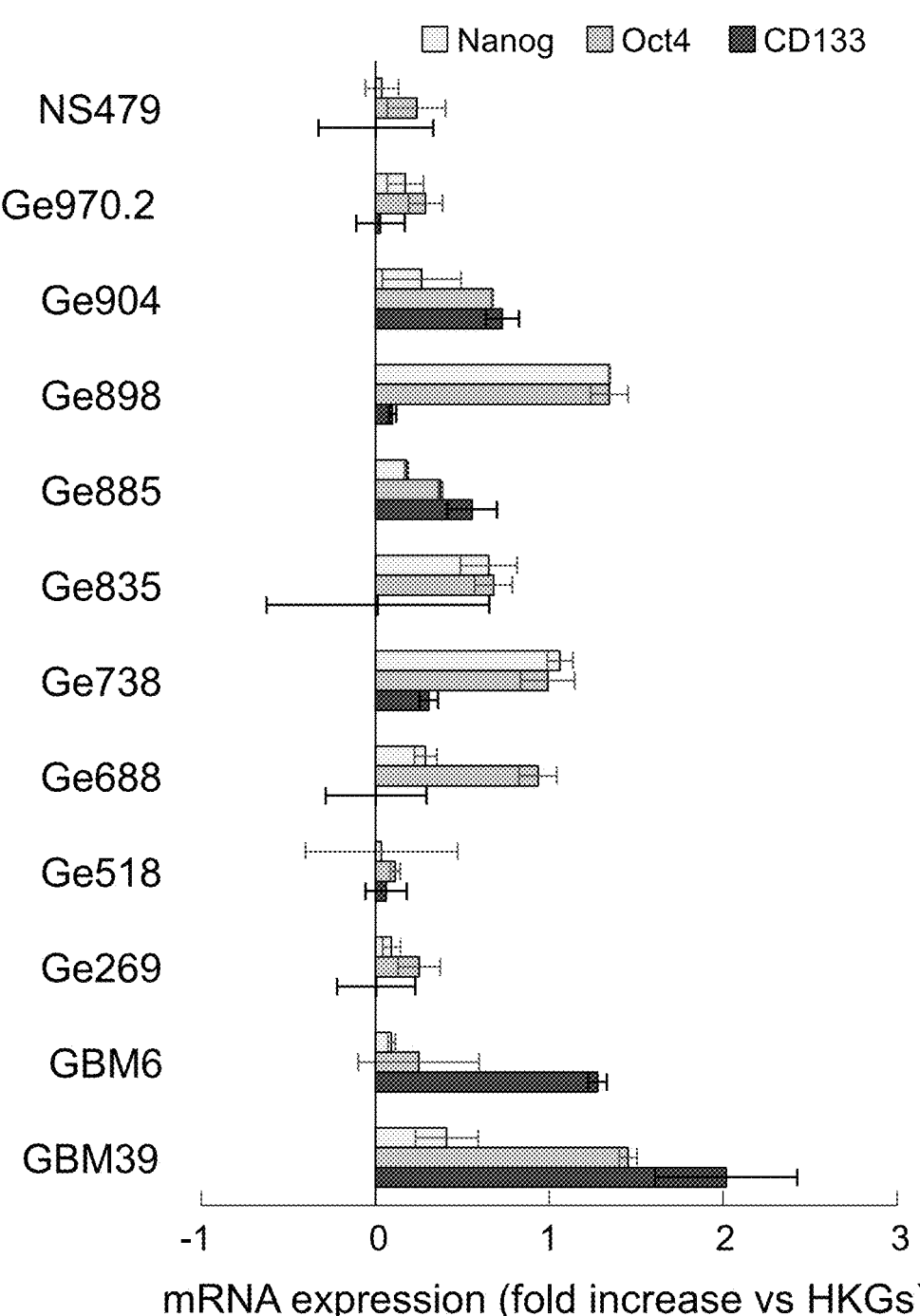
Figure 15D:
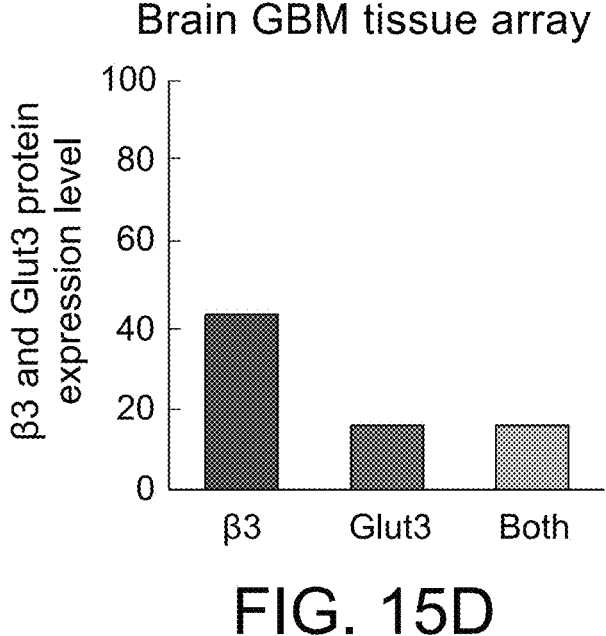
Figure 15E:
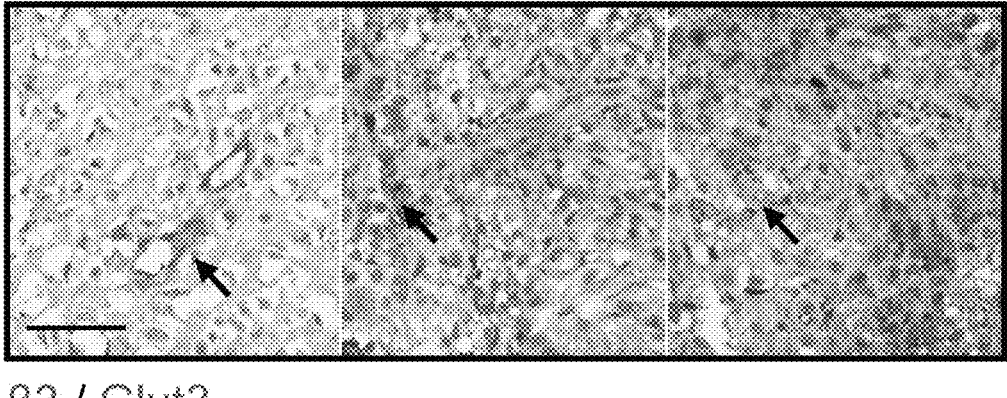
Figure 15F:
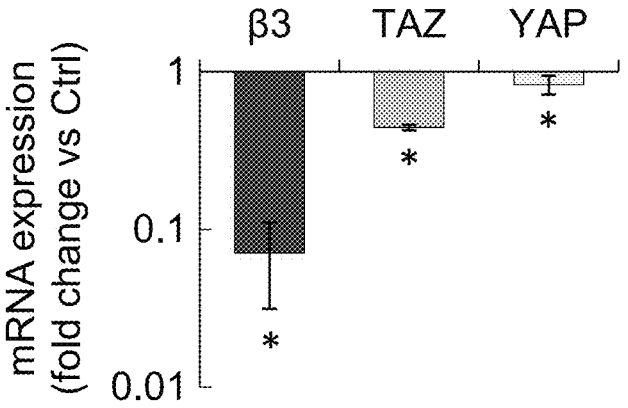
Figure 15G:
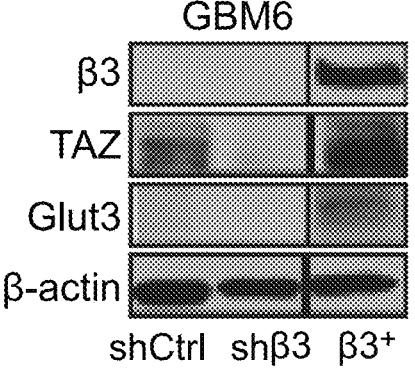
Figure 15H:
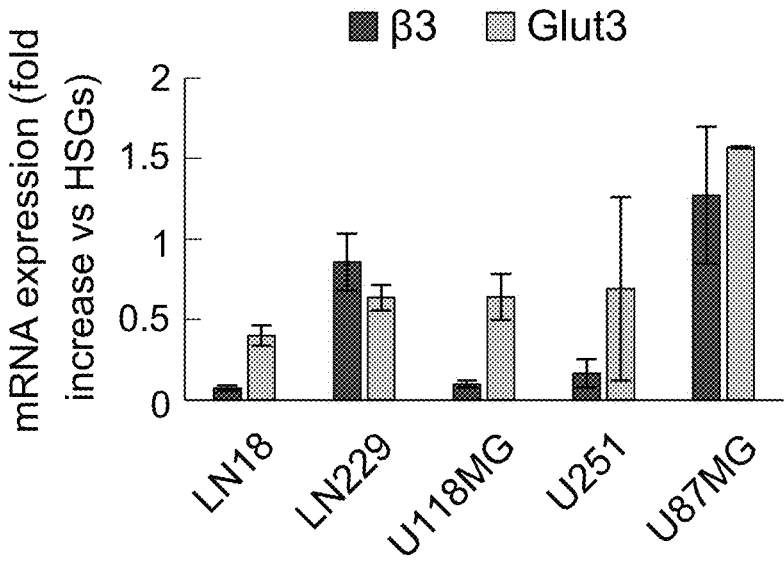
Figure 15I:
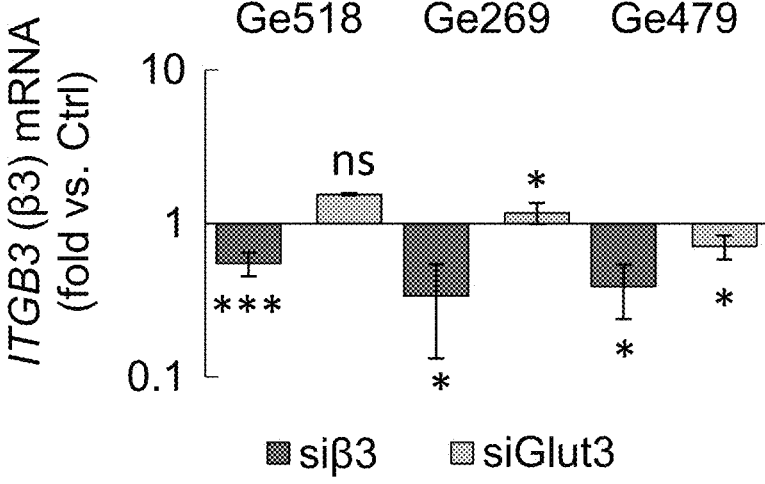
Figure 15J:
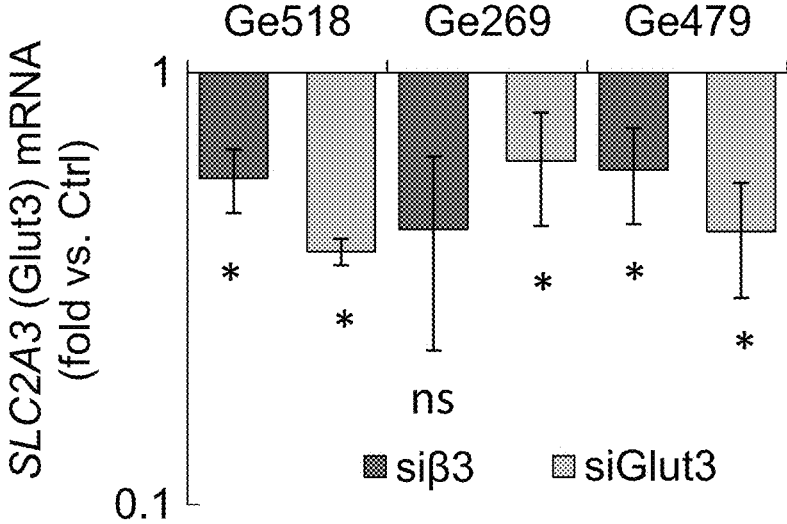

FIG. 15B illustrates light micrograph images showing that GSCs are multipotent and can differentiate to form neurons (βIIITubulin) (upper image) and astrocytes (GFAP) (lower image); DAPI was used for nuclear counterstaining;

FIG. 15C graphically illustrates data showing that GSCs express cancer stem cell markers (CD133, Oct4 and Nanog); mRNA expression was determined by qPCR in all GSCs and normalized to housekeeping genes (HKGs);

FIG. 15D-E: shows a histological analysis of brain GBM tissue array (GL805c): FIG. 15D graphically illustrates a bar graph representing β3 and Glut3 expression level detected on tumor cells for 70 specimens, and FIG. 15E illustrates light microscopy images of tumors stained for haematoxylin and eosin (H&E), β3 and Glut3;

FIG. 15F graphically illustrates data showing β3, TAZ and YAP mRNA expression, which were determined by qPCR for Ge479 (n=3);

FIG. 15G illustrates representative immunoblots showing expression of indicated proteins when ectopically expressed β3 is GBM6 (n=2);

FIG. 15H graphically illustrates data showing β3 and Glut3 mRNA expression, mRNA was determined by qPCR in all GBM lines, and FIG. 15I-J: graphically illustrate data showing the effect of β3 (FIG. 15I) and Glut3 (FIG. 15J) knockdown on mRNA expression of ITGB3 (B3) and SLC2A3 (Glut3) determined by qRT-PCR, displayed as fold change for gene expression normalized to siCtrl in Ge518, Ge269 and Ge479 (n=2-4);

as discussed in detail in Example 1, below.

Figure 16A:
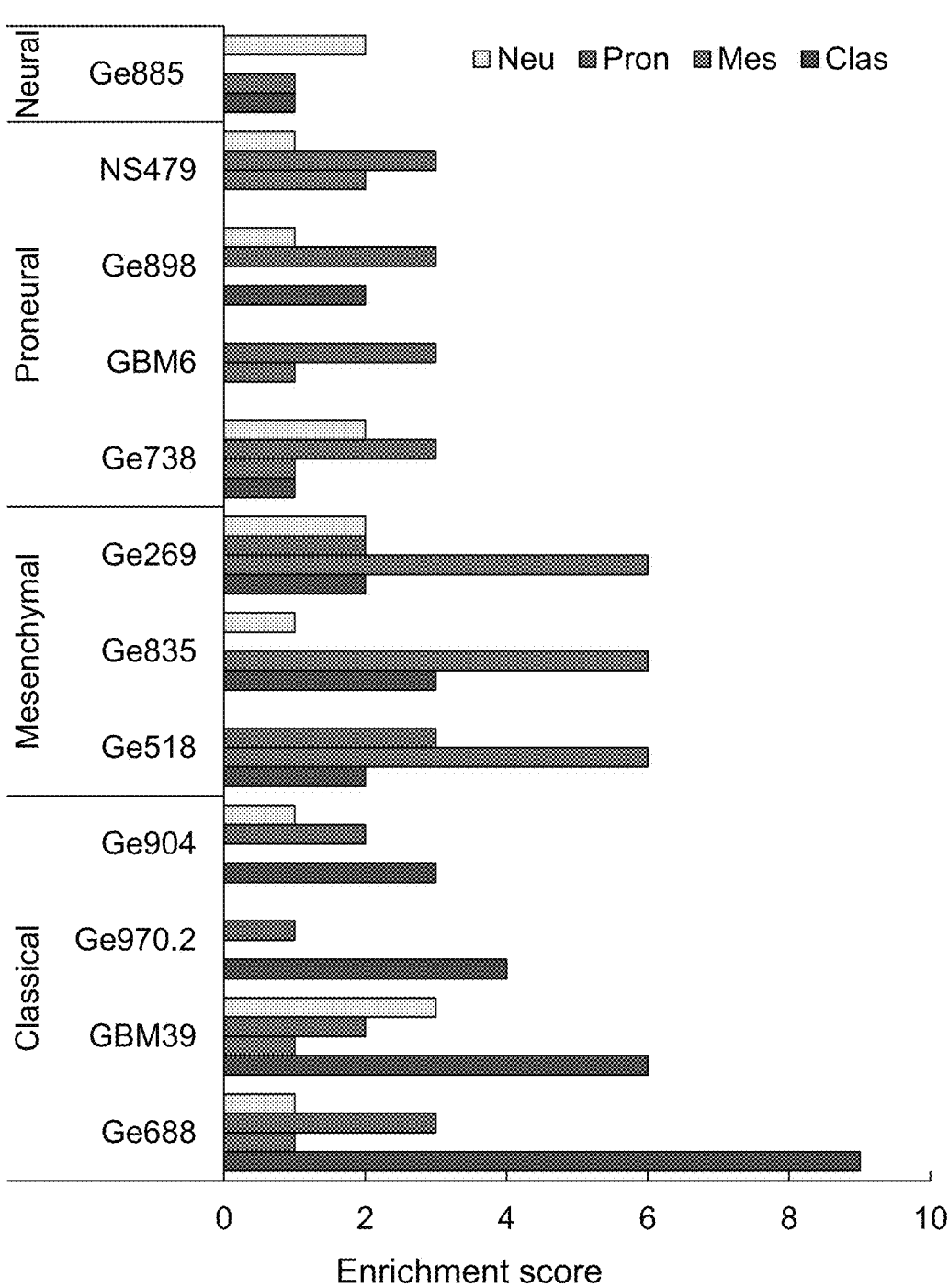
Figure 16B:
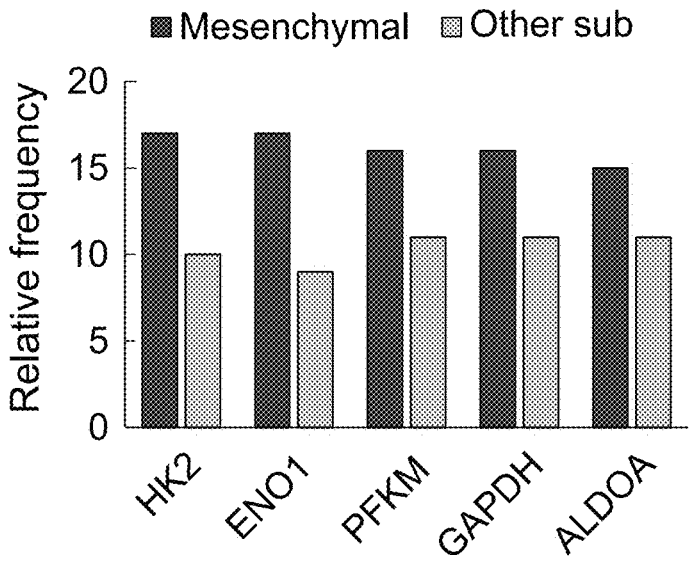
Figure 16C:
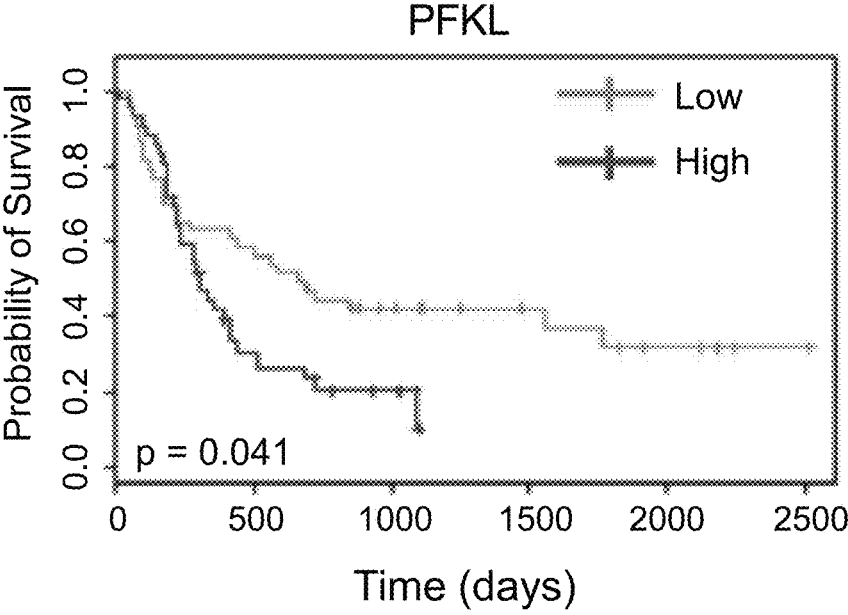
Figures 16D, 16E, 16F:
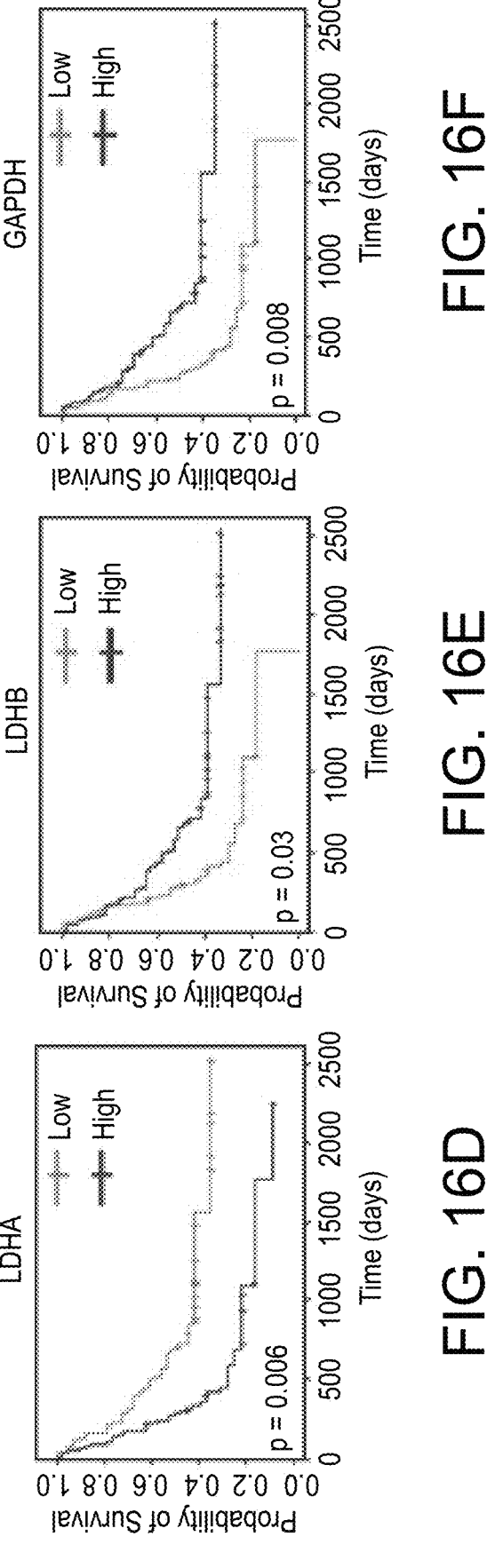

FIG. 16A-F: GSCs classification and enrichment analysis of glycolytic genes:

FIG. 16A graphically illustrates data showing mRNA levels in various neural, proneural, mesenchymal, and classical GSC (Glioblastoma Stem Cell) samples; mRNA was determined by qPCR in all GSCs, several genes (listed in the table of FIG. 10) have been tested for each GBM subtypes, and an enrichment score was determined according to gene expression normalized to housekeeping genes;

FIG. 16B graphically illustrates an enrichment analysis of glycolytic genes in mesenchymal and other samples (HK2, ENO1, PFKM, GAPDH and ALDOA); and, FIG. 16C-F graphically illustrate Kaplan-Meier analyses of Freije dataset for: FIG. 16C graphically illustrates PFKL expression (n=42 β3 low, n=43 β3 high; P=0.041); FIG. 16D graphically illustrates LDHA expression (n=42 β3 low, n=43 β3 high; P=0.006); FIG. 16E graphically illustrates LDHB expression (n=42 β3 low, n=43 β3 high; P=0.03) and FIG. 16F graphically illustrates GAPDH expression (n=42 β3 low, n=43 β3 high; P=0.008);

as discussed in detail in Example 1, below.

Figures 17A, 17B:
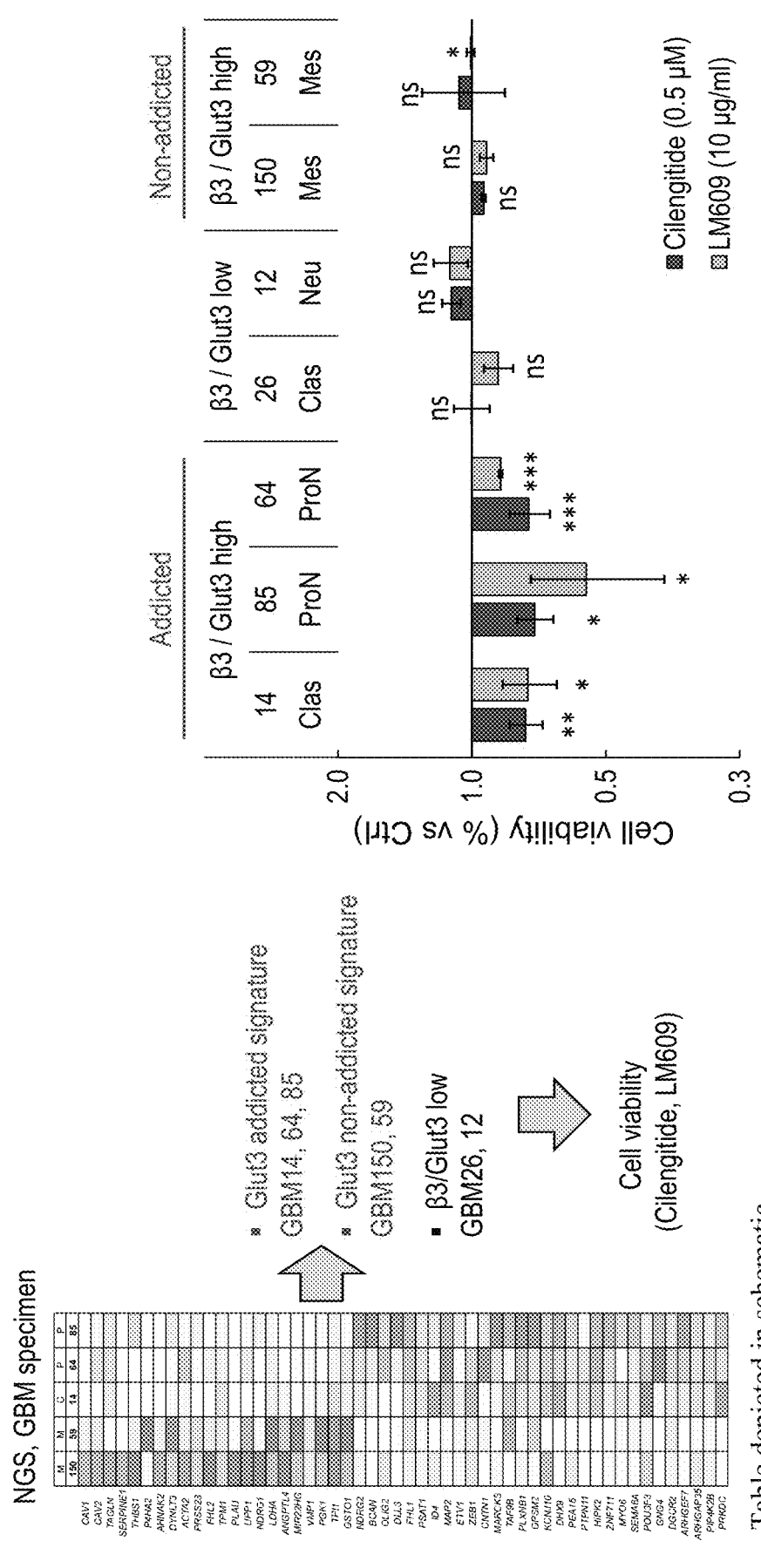

FIG. 17A-B: FIG. 17A illustrates a schematic depicting a Mayo Clinic sample request, where samples were requested based on their Glut3 addicted vs. non-addicted signature (also depicted in FIG. 18), and then analyzed for cell viability in presence of cilengitide and LM609; and, FIG. 17B graphically illustrating the effect of LM609 (αvβ3 function blocking antibody) and cilengitide (cyclic peptide antagonist of av integrins including αvβ3 and αvβ5) on Mayo Clinic GSCs cell viability measured by CELLTITER-GLO™ (CellTiter-Glo) in GSCs (n=3-5, except n=2 for GBM150 and GBM85), as discussed in detail in Example 1, below.

FIG. 18A-B illustrates a table showing Glut3 addicted vs non-addicted signature for Mayo Clinic GSCs extracted from Next Generation Sequencing (NGS) data. M=Mesenchymal, C=Classical, P=Proneural and N=Neural, as discussed in detail in Example 1, below.

Figure 19:
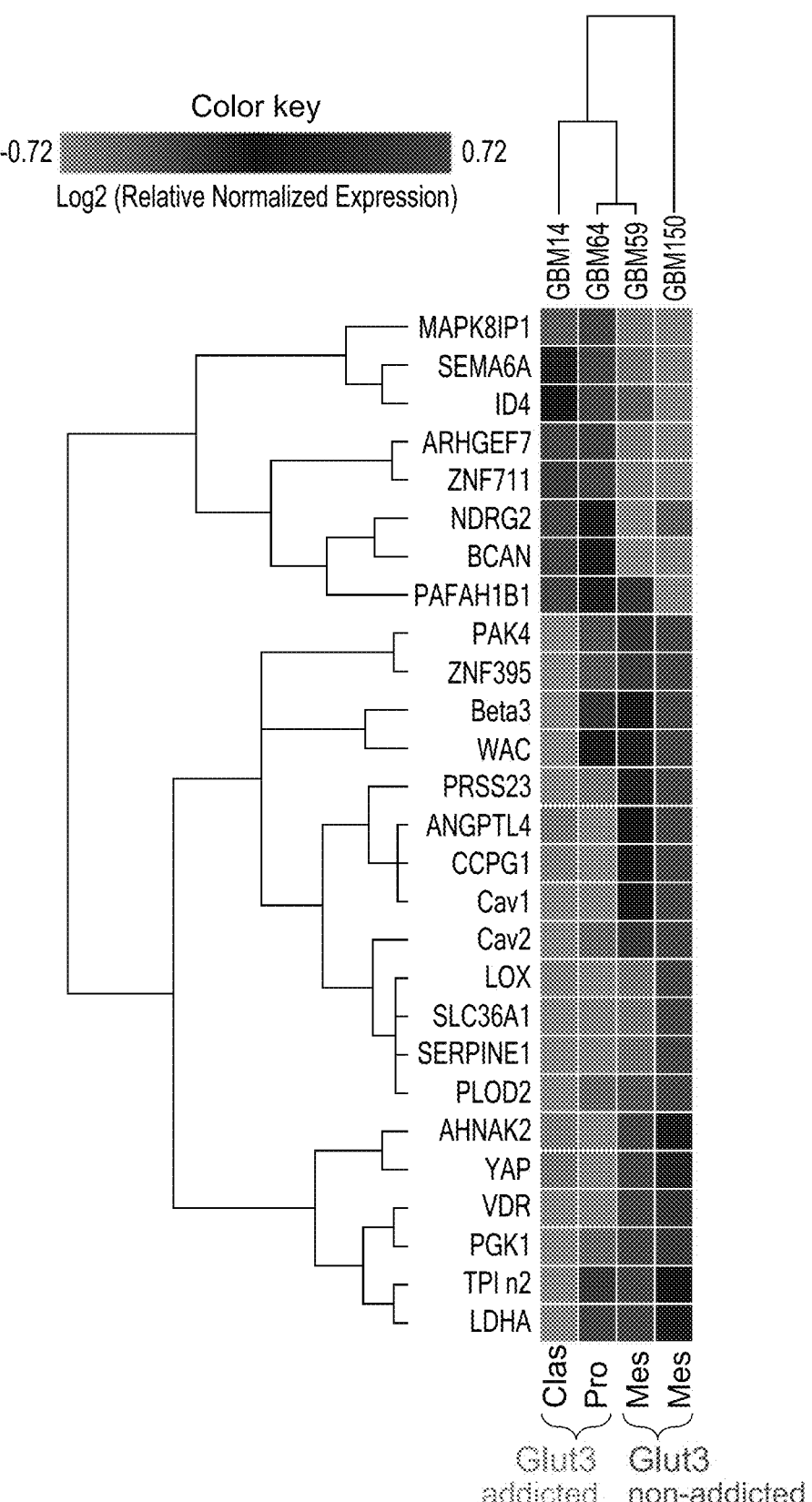

FIG. 19 illustrates the relative normalized expression of various mRNAs (as indicated in the Figure) in Glut3 addicted and Glut3 non-addicted samples, as determined by qRT-PCR (n=2), and Bio-Rad software has been used for analysis, as discussed in detail in Example 1, below.

Figures 20A, 20B:
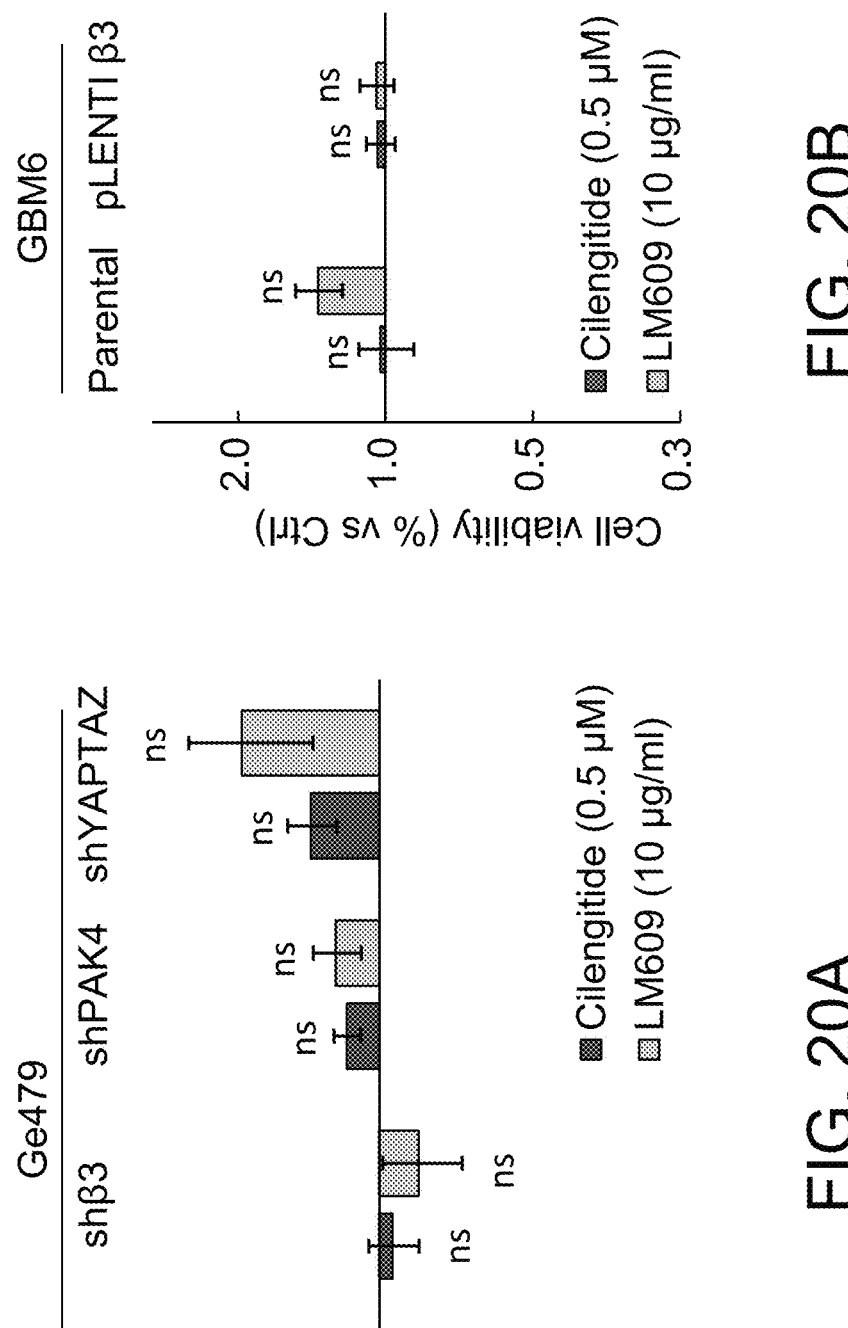

FIG. 20A-B: FIG. 20A graphically illustrates the effect of LM609 (αvβ3 function blocking antibody) and cilengitide (cyclic peptide antagonist of av integrins including αvβ3 and avβ5) on cell viability of Ge479 knockdown for 33, PAK4 and YAP/TAZ measured by CELLTITER-GLO™ in GSCs (n=3-5); FIG. 20B graphically illustrates the effect of LM609 (αvβ3 function blocking antibody) and cilengitide (cyclic peptide antagonist of av integrins including αvβ3 and αvβ5) on cell viability of GBM6 with ectopic expression of 33 measured by CELLTITER-GLO™ in GSCs (n=3-5), as discussed in detail in Example 1, below.

Figure 21:
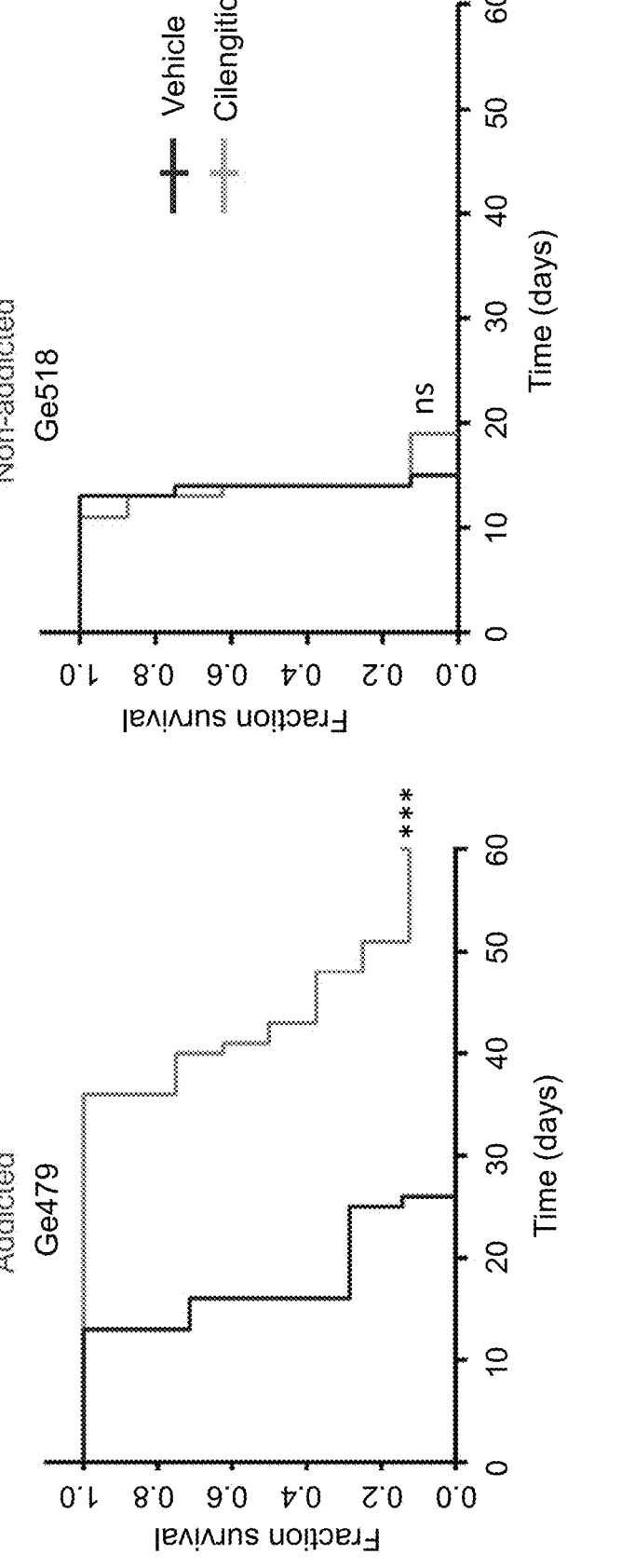

FIG. 21 graphically illustrates data showing the effect of Cilengitide on tumor growth, where mice bearing orthotopic Ge518 (Glut3 non-addicted) and Ge479 (Glut3 addicted) brain tumors were treated with vehicle or cilengitide (25 mg kg-1; 8 mice per group), as discussed in detail in Example 1, below.

Figure 22:
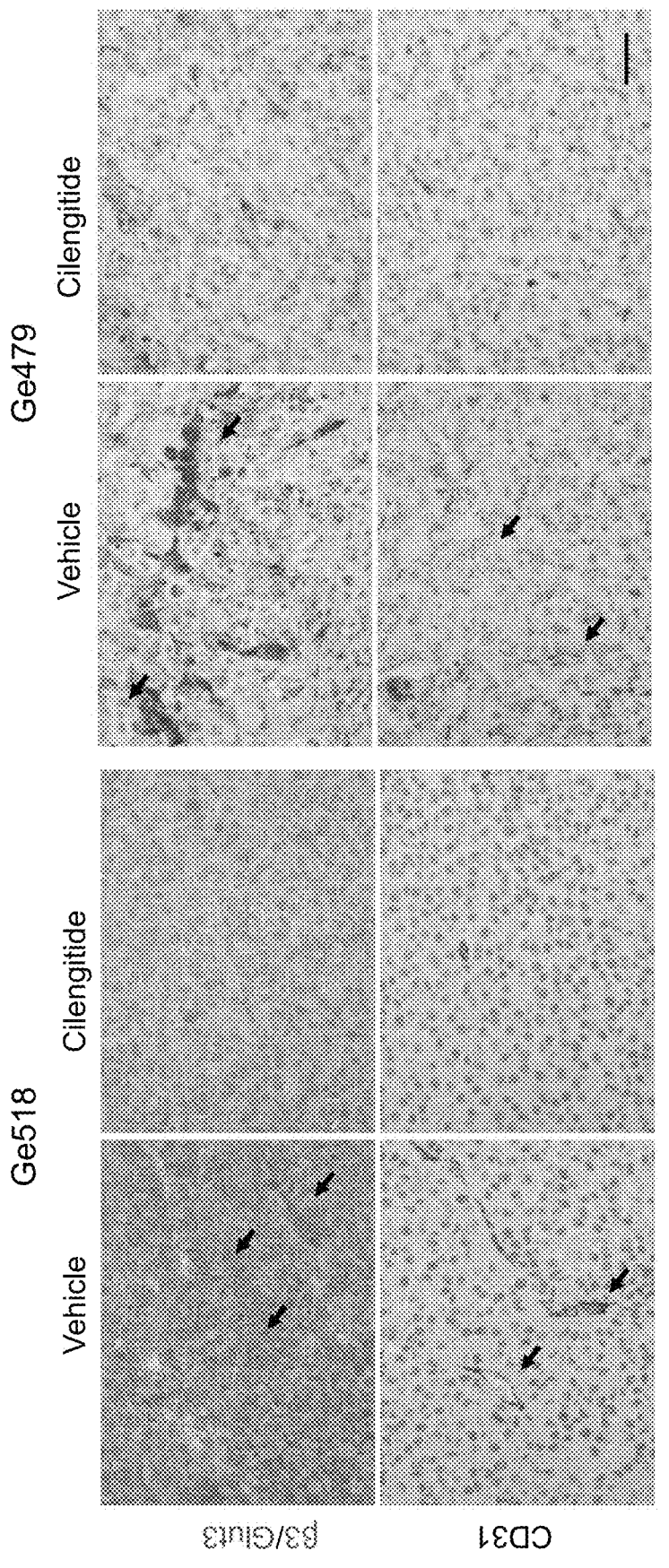

FIG. 22 illustrates images of histological analysis of Ge518 and Ge479 xenografts. Ge518 (n=2-3 mice) and Ge479 (n=3-4 mice) tumors were stained for haematoxylin and eosin (H&E), 3 (brown), Glut3 (blue) and CD31 (brown), as discussed in detail in Example 1, below.

FIG. 23 illustrates a three-step process to determine GBM tumor Glut3 addiction status: a tumor is predicted to be Glut3-addicted if there is evidence of 1) high dual expression of ITGB3 (integrin β3) and SLC2A3 (Glut3), 2) high expression of markers associated with the addiction signature, and 3) low expression of markers associated with the non-addiction signature. Bioinformatics software is used to make the determination of high vs. low expression for each gene among the samples being compared. This is a relative value based on the expression levels among the datasets analyzed. For the 5 PDX models compared in FIG. 18, THBS1 expression ranges from 0 to 45, where the units represent normalized FPKM (fragments per kilobase per million mapped reads). In contrast, expression levels of BCAN range from 1 to 743. It is therefore useful to compare a sample with unknown status to multiple benchmark samples with known Glut3 addiction (or non-addiction) to determine the high/low threshold values for each gene.

Like reference symbols in the various drawings indicate like elements.

Reference will now be made in detail to various exemplary embodiments, examples of which are illustrated in the accompanying drawings. The following detailed description is provided to give the reader a better understanding of certain details of aspects and embodiments as provided herein, and should not be interpreted as a limitation on the scope of the invention.

DETAILED DESCRIPTION

In alternative embodiments, provided are methods for treating cancers, e.g., glioblastoma (GBM) tumors or GBM cancer cells, which is sensitive to a treatment targeting the integrin avb3 (αvβ3) pathway, wherein ascertaining whether the cancer or tumor cell is sensitive to treatment targeting the integrin avb3 (αvβ3) pathway is determined by using a method as provided herein. In alternative embodiments, provided are methods for determining whether a glioblastoma (GBM) tumor or GBM cancer cell will be sensitive to a treatment targeting the integrin avb3 (αvβ3) pathway, comprising determining whether the GBM tumor or the GBM cancer cell expresses both avb3+ and Glut3+ along with (and) a genetic signature associated with Glut3 addiction, e.g., in one embodiment, the GBM tumor or the GBM cancer cell is an avb3+/Glut3+ tumor or cancer cell and it has markers consistent with the Classical or Proneural molecular subtypes of GBM or expresses (e.g., expresses mRNA or protein) at least one (one or more) one of the genes consistent with a Glut3 addicted gene/molecular signature, e.g., as listed in FIG. 11 or FIG. 23, wherein if a GBM tumor or the GBM cancer cell expresses both avb3+ and Glut3+ and has a molecular signature associated with Glut3 addiction, the GBM tumor or the GBM cancer cell will be sensitive to (will be successfully treated by) the treatment targeting the integrin avb3 (αvβ3) pathway.

In alternative embodiments, embodiments provided herein solve the problem of why certain glioblastoma (GBM) tumors are either sensitive or resistant to agents targeting or inhibiting the integrin avb3 (αvβ3) pathway, including avb3, Glut3, PAK4, or YAP/TAZ. This invention for the first time found that expression of integrin avb3 or GLUT3 is not sufficient to predict sensitivity to these agents. Instead, we found that subsets of avb3+/Glut3+ tumors are sensitive to agents targeting or inhibiting the integrin avb3 (αvβ3) pathway, and that these subsets of avb3+/Glut3+ tumors fall within the Classical and Proneural molecular subtypes previously described for GBM. Therefore, provided herein are methods for determining whether a GBM tumor may be a good or bad candidate for therapeutic strategies targeting or inhibiting the integrin avb3 pathway, including avb3, Glut3, PAK4, or YAP/TAZ. We estimate this "sensitive" population to represent about 10% of GBM tumors. Also provided herein are methods of treating glioblastoma (GBM) tumors found to be sensitive to agents targeting or inhibiting the integrin avb3 (αvβ3) pathway, wherein the sensitivity is determined by methods as provided herein.

Methods as provided herein for the first time find and describe that integrin αvβ3 regulates Glut3 (SLC2A3) expression and thus allows cells to evade senescence. In one embodiment, we found and defined a subpopulation of αvβ3-positive GBM tumors that are particularly sensitive to cilengitide (or, 2-[(2S,5R,8S,11S)-5-benzyl-11-{3-[(diaminomethylidene)amino]propyl}-7-methyl-3,6,9,12,15-pentaoxo-8-(propan-2-yl)-1,4,7,10,13-pentaazacyclopentadecan-2-yl]acetic acid) or other agents targeting this axis (i.e., the integrin avb3 pathway). Interestingly, αvβ3 expression is not sufficient to predict sensitivity, as only a subset of αvβ3-expressing GBM tumors are addicted to Glut3. This subset (GBM tumors are addicted to Glut3) includes tumors within the Classical or Proneural GBM molecular subtypes, or tumors which express markers consistent with the Glut3-addicted gene/molecular signature, e.g., as listed in FIG. 11 or FIG. 23. These findings may explain why the integrin antagonist cilengitide had a benefit for some patients, but not others, in recently completed clinical trials in which the drug was given to patients from an unselected population.

In alternative embodiments, embodiments provided herein solve the problem, and unmet need, to predict which patients will or will not be responsive to treatments for GBM. Despite gene expression analysis to compare individual GBM tumors, to date no targeted therapies have shown efficacy. We have discovered that the addiction of certain GBM cells to Glut3 can be used to predict drug sensitivity. This addiction is a unique type of biomarker, and one which would typically be tested in functional assays. In alternative embodiments, we have compared the gene expression profiles of tumors that are Glut3-addicted versus (vs.) non-addicted (see FIG. 11), and thus we have established a panel of genes that can be used to infer Glut3 addiction, and thus sensitivity to cilengitide and other agents targeting the integrin avb3 pathway, including avb3, Glut3, PAK4, or YAP/TAZ. In alternative embodiments Glut3 addiction is identified using the full panel of 314 signature genes as illustrated in FIG. 11. In alternative embodiments, these include high expression of SEMA6A, ARHGEF7, MAPK8IP1, and PAFAH1B1, along with low expression of CNTN1, KDM2A, ZNF395, RASA3, PRSS23, SNX10, ZKSCAN1, CCPG1, SLC36A1, P4HA2, VDR, WAC, LDHA, and LOX.

In alternative embodiments of methods provided herein, a patient is diagnosed with a cancer, e.g., a GBM, and a biopsy is taken (e.g., a blood or a tissue sample) and analyzed for gene expression. Depending on the gene expression profile, a treatment with cilengitide—or any drug, small molecule, polypeptide and the like, targeting the integrin avb3 pathway, including avb3, Glut3, PAK4, or YAP/TAZ, would be recommended (for administration to the patient diagnosed with the cancer or tumor), or not. Methods as provided herein allow this drug, small molecule or other therapeutic that target elements of the integrin avb3 pathway, including avb3, Glut3, PAK4, or YAP/TAZ, to be used on this identified (i.e., drug sensitive) patient population. We estimate about 10% of GBM patients to fall into this category. This embodiment has been validated using established human GBM cell lines and patient-derived GBM stem cells, in vivo and in vitro, as described in Example 1, below.

Exemplary Methods for Identifying Cells that are Glut-3 Addicted

In alternative embodiments, provided are methods for determining whether a tumor or a cancer cell will be sensitive to (or can be killed or induced to senescence by) a treatment targeting the integrin avb3 (αvβ3) pathway, comprising: (a) determining or having determined whether the tumor or the cancer cell expresses both avb3+ and Glut3+, or determining whether the tumor or the cancer cell is a avb3+/Glut3+ tumor or cancer cell, and (b) determining or having determined whether the tumor or the cancer cell is Glut-3 addicted.

In alternative embodiments, determining or having determined whether the tumor or the cancer cell is Glut-3 addicted comprises determining or having determined whether the tumor or the cancer cell expresses a marker (e.g., an mRNA or a protein) consistent with a Classical or Proneural subtype, e.g., expresses a marker consistent with the Classical or Proneural molecular subtypes of GBM, wherein optionally the marker consistent with a Classical or Proneural subtype comprises an EGFR, GLI1, NES, DLL3 or OLIG2 gene transcript or an EGFR, GLI1, NES, DLL3 or OLIG2 protein.

In alternative embodiments, determining or having determined whether the tumor or the cancer cell is Glut-3 addicted comprises determining or having determined whether the tumor or the cancer cell expresses (e.g., expresses mRNA or protein) from at least one (one or more) or two or more, or 3, 4, 5, 6, 7 or 8 or more, of the genes as listed in FIG. 11 or FIG. 23, at levels as indicated in the Figures.

In alternative embodiments, the expression of a single gene is sufficient to make a determination of (to predict) Glut3 addiction; however, in alternative embodiments, the expression levels of approximately 2, 3, 4, 5, 6, 7 or 8 gene is sufficient to make a determination of (to predict) Glut3 addiction—where both high and low expression of selected genes is taken into consideration in making the determination, e.g., as schematically shown in FIG. 23.

In alternative embodiments, a minimum of approximately 6 genes is sufficient to make a determination of Glut3 addiction: where in one embodiment, 3 of which can be classified as being expressed at high levels, and 3 of which can be classified as being expressed at low levels, to be sufficient to make a determination of Glut3 addiction. In alternative embodiments, a minimum of approximately 8 genes is sufficient to make a determination of Glut3 addiction: where in one embodiment, 4 of which can be classified as being expressed at high levels, and 4 of which can be classified as being expressed at low levels, to be sufficient to make a determination of Glut3 addiction; in another embodiment, 5 genes classified as being expressed at high levels, and 3 genes classified as being expressed at low levels is sufficient to make a determination of Glut3 addiction; in another embodiment, 3 genes classified as being expressed at high levels, and 5 genes classified as being expressed at low levels is sufficient to make a determination of Glut3 addiction; and the like. The more genes analyzed, the better confidence the practitioner has in the predictive value of this screen, i.e., of the methods as provided herein.

The "expression level" for any single gene, i.e., whether it is expressed at a "high" or a "low" level" is relative measurement, not an absolute one. The raw value for a single gene is first normalized to multiple housekeeping genes, positive controls, and negative controls. Gene expression can be compared within a single biological sample, or between multiple samples.

In alternative embodiments, determining or having determined whether the tumor or the cancer cell is Glut-3 addicted comprises using a custom array comprising substantially or all or these genes as listed in FIG. 11. In alternative embodiments, the array is a 314 gene expression array which is generated by comparing GLUT3 expression with survival from the publicly available Freije dataset: 143 genes on Glut3 non-addicted list (FIG. 11—left column), where a drug-sensitive tumor should show low expression, and 171 genes on Glut3-addicted list (FIG. 11—right column), where a drug-sensitive tumor should show high expression. Sensitivity to αvβ3 blockade (i.e., how drug-sensitive the tumor is) will be proportional to how well a given tumor fits this profile. A tumor with the best predicted sensitivity will show very high expression of some (but not all) of the 171 genes on the Glut3-addicted panel and very low expression of some (but not all) of the 143 genes on the Glut3 non-addicted panel.

In alternative embodiments, determining or having determined whether the tumor or the cancer cell is Glut-3 addicted comprises using custom array containing a subset of genes shown in FIG. 5G, i.e., a subset of the 19 listed genes. This is a subset of the full list shown in FIG. 11, and was validated using patient-derived (Glioblastoma Stem Cell) models with known Glut3 addiction status:

15 genes indicated Glut3 non-addiction, for example, in alternative embodiments, a drug-sensitive sensitive tumor will show low expression of 1, 2, 3, 4, 5, 6, 7, 8, 9, 10, 11, 12, 13, 14 or all 15 of the genes: CNTN1, KDM2A, ZNF395, RASA1, PRSS23, SNX10, ZKSCAN1, CCPG1, PLOD2, SLC36A1, P4HA2, VDR, WAC, LDHA and/or LOX; and 4 genes indicated Glut3-addiction, for example, in alternative embodiments, a drug-sensitive tumor will show high expression of 1, 2, 3 or all 4 of the genes: SEMA6A, ARHGEF7, MAPK8IP1 and/or PAFAH1B1.

Validation:

Note that for the GBM GSC models shown, the tumors with proven Glut3 addiction (GBM39/GBM79) or non-addiction (GBM518/GBM269) evaluated independently using Glut3 knockdown did not show identical expression profiles. For this reason, in some embodiments, analysis of a single marker may not be sufficient to infer Glut3 addiction, but rather 2, 3, 4, 5, 6, 7 or 8 or more gene levels may need to be analyzed (e.g., as described herein) for a more accurate determination of Glut3 addiction.

In alternative embodiments, determining or having determined whether the tumor or the cancer cell is Glut-3 addicted comprises using a custom array comprising a subset of genes as shown in FIG. 18, i.e., a subset of the 53 listed genes. This is a subset of the full list shown in FIG. 11, validated using patient-derived xenograft models obtained from the Mayo Clinic;

22 genes indicated Glut3 non-addiction, for example, in alternative embodiments, a drug-sensitive tumor will show low expression of 1, 2, 3, 4, 5, 6, 7, 8, 9, 10, 11, 12, 13, 14, 15, 16, 17, 18, 19, 20, 21 or all 22 of the genes: CAV1, CAV2, TAGLN, SERPINE1, THBS1, P4HA2, AHNAK2, DYNLT3, ACTA2, PRSS23, FHL2, TPM1, PLAU, UPP1, NDRG1, LDHA, ANGPTL4, MIR22HG, VMP1, PGK1, TPI1 and/or GSTO1; and 30 genes indicated Glut3-addiction, for example, in alternative embodiments, a drug-sensitive tumor will show high expression of 1, 2, 3, 4, 5, 6, 7, 8, 9, 10, 11, 12, 13, 14, 15, 16, 17, 18, 19, 20, 21, 22, 23, 24, 25, 26, 27, 28, 29 or all 30 of the genes: NDRG2, BCAN, OLIG2, DLL3, FHL1, PSAT1, ID4, MAP2, ETV1, ZEB1, CNTN1, MARCKS, TAF9B, PLXNB1, GPSM2, KCNJ10, DHX9, PEA15, PTPN11, HIPK2, ZNF711, MYO6, SEMA6A, POU3F3, GNG4, DGCR2, ARHGEF7, ARHGAP35, PIP4K2B and/or PRKDC.

Validation:

As shown in FIG. 18, GBM150 and GBM59 (tumors with independently validated mesenchymal subtype) show high expression of many (but not all) of the Glut3-nonaddicted genes and low expression of many (but not all) of the Glut3-addicted genes. Cells isolated from these tumors were shown to be largely resistant to both LM609 and cilengitide in FIG. 17B.

As shown in FIG. 18, GBM14, GBM64, and GBM85 (tumors with independently validated Classical or Proneural subtypes) show low expression of many (but not all) of the Glut3-nonaddicted genes and high expression of many (but not all) of the Glut3-addicted genes. Cells isolated from these tumors were shown to be largely sensitive to both LM609 and cilengitide in FIG. 17B.

Note that while the insensitive tumors (GBM150/GBM59) show a similar genetic signature, not all genes show a significant difference in expression compared to the sensitive tumors (GBM14/GBM64/GBM85).

In alternative embodiments, determining or having determined whether the tumor or the cancer cell is Glut-3 addicted comprises using a custom array containing a subset of genes shown in FIG. 19, i.e., a subset of the 27 listed genes. This is a subset of the full list shown in FIG. 11, validated using patient-derived xenograft models obtained from the Mayo Clinic:

19 genes indicated Glut3 non-addiction, for example, in alternative embodiments, a drug-sensitive tumor will show low expression of 1, 2, 3, 4, 5, 6, 7, 8, 9, 10, 11, 12, 13, 14, 15, 16, 17, 18 or all 19 of the genes PAK4, ZNF395, ITGB3, WAC, PRSS23, ANGPTLA4, CCPG1, CAV1, CAV2, LOX, SLC36A1, SERPINE1, PLOD2, AHNAK2, YAP, VDR, PGK1, TPI n2 and/or LDHA; and 8 genes indicated Glut3-addiction, for example, in alternative embodiments, a drug-sensitive tumor will show high expression of 1, 2, 3, 4, 5, 6, 7 or all 8 of the genes MAPK8Ip1, Sema6A, ID4, ARHGEF7, ZNF711, NDRG2, BCAN and/or PAFAHIB1.

Validation:

As shown in FIG. 18, GBM150 and GBM59 (tumors with independently validated mesenchymal subtype) show high expression of many (but not all) of the Glut3-nonaddicted genes and low expression of many (but not all) of the Glut3-addicted genes. Cells isolated from these tumors were shown to be largely resistant to both LM609 and cilengitide in FIG. 17B.

As shown in FIG. 18, GBM14, GBM64, and GBM85 (tumors with independently validated Classical or Proneural subtypes) show low expression of many (but not all) of the Glut3-nonaddicted genes and high expression of many (but not all) of the Glut3-addicted genes. Cells isolated from these tumors were shown to be largely sensitive to both LM609 and cilengitide in FIG. 17B.

Note that while the insensitive tumors (GBM150/GBM59) show a similar genetic signature, not all genes show a significant difference in expression compared to the sensitive tumors (GBM14/GBM64/GBM85).

Exemplary Methods for Cell Isolation, Biopsy and Gene Analysis

In alternative embodiments of methods provided herein, after a patient is diagnosed with a cancer or tumor, e.g., a GBM, a melanoma tumor or melanoma cell or a primitive neuroectodermal tumor (PNET) or PNET cell, a biopsy is taken (e.g., a blood, serum or a tissue sample is taken) and analyzed for gene expression. Any biopsy method or technique known in the art can be used, and any method or process for analysis of gene expression or nucleic acid amplification or screening can be used to determine the gene or molecular profile of a cell, and any process or method for the isolation of tumor or cancer cells can be used.

For example, methods for performing a genetic analysis on a DNA target region from a test sample can be performed as described in U.S. patents application Nos. 20180163272 A1; 20180163201 A1; 20180142234 A1; 20180119230 A1; 20180119214 A1; 20180155768 A1; 20180137242 A1; and, U.S. Pat. Nos. 9,944,978; 9,914,977; 9,650,677; 9,447,411; 9,938,519; 9,932,576.

For example, biopsy methods, or methods for isolating a tumor or cancer cell for analysis, can be performed as described in U.S. patents application Nos. 20180161774 A1 (describing a microfluidic device for trapping circulating tumor cells); 20180161021 A1 (describing a biopsy device, comprising a flexible coaxial structure); 20180136210 A1, 20180153529 A1, 20180125466 A1 and 20180116643 A1 (describing biopsy devices); or as described in U.S. Pat. Nos. 9,993,230; 9,974,523; 9,968,339.

Exemplary Methods for Treating Cancers

In alternative embodiments, provided are methods for treating or ameliorating, or killing, or inducing into senescence, a tumor or a cancer cell in a patient or ex vivo, wherein optionally the tumor or cancer cell is a glioblastoma (GBM) tumor or a GBM cancer cell, or a melanoma or a primitive neuroectodermal tumor (PNET), or treating or ameliorating a tumor or cancer, optionally GBM, a melanoma or a primitive neuroectodermal tumor (PNET), in an individual in need thereof. Any method or protocol known in the art can be used to practice these methods.

For example, exemplary methods for treating or ameliorating, or killing, or inducing into senescence GBM are described in U.S. Pat. Nos. 9,872,857; 9,687,466; 9,662,377; 9,587,239; 9,573,960; 9,421,202; 9,364,532; 9,364,505; 9,283,195; 9,145,462. Exemplary methods for treating or ameliorating, or killing, or inducing into senescence melanomas are described in U.S. Pat. Nos. 9,962,348; 9,949,947; 9,937,161; 9,920,121; 9,901,629. Exemplary methods for treating or ameliorating, or killing, or inducing into senescence PNETs are described in U.S. Pat. Nos. 7,678,759; 6,667,156; or U.S. patent application No. 20130303460 A1.

The invention will be further described with reference to the following examples; however, it is to be understood that the exemplary embodiments provided herein are or the invention are not limited to such examples.

EXAMPLES

Example 1: Glut3 Addiction is a Druggable Vulnerability for a Molecularly Defined Subpopulation of Glioblastoma (GBM)

This Example and the data presented herein demonstrate that alternative embodiments of methods provided herein are effective in determining whether or not a treatment with cilengitide—or any drug targeting the integrin avb3 pathway, including avb3, Glut3, PAK4, or YAP/TAZ, would be recommended, or not, for treating a GBM.

By analyzing clinical GBM samples and patient-derived glioblastoma-initiating cells, we identified a subpopulation of GBM tumors for which αvβ3 integrin controls Glut3 expression to regulate glucose metabolism, thus allowing cells to avoid senescence. Here, we describe a method to identify those GBM that are particularly sensitive to αvβ3 antagonists, including cilengitide.

While GBM tumors are highly aggressive and therapy-resistant, individual tumors achieve this state via distinct molecular pathways. Here, we define a unique biological subpopulation addicted to an integrin αvβ3-mediated pathway that enhances glucose uptake, making tumors highly sensitive to a variety of agents that disrupt this advantage. Interestingly, αvβ3 expression alone is not sufficient to define this population, as only a subset of αvβ3-expressing GBM tumors are addicted to this pathway. Our findings may explain why the integrin antagonist cilengitide had a benefit for some patients, but not others, in clinical trials. By revealing a direct link between aberrant integrin expression and altered glucose metabolism, this work identifies a context-dependent druggable vulnerability that can be exploited for GBM therapy.

Results

Figure 1A:
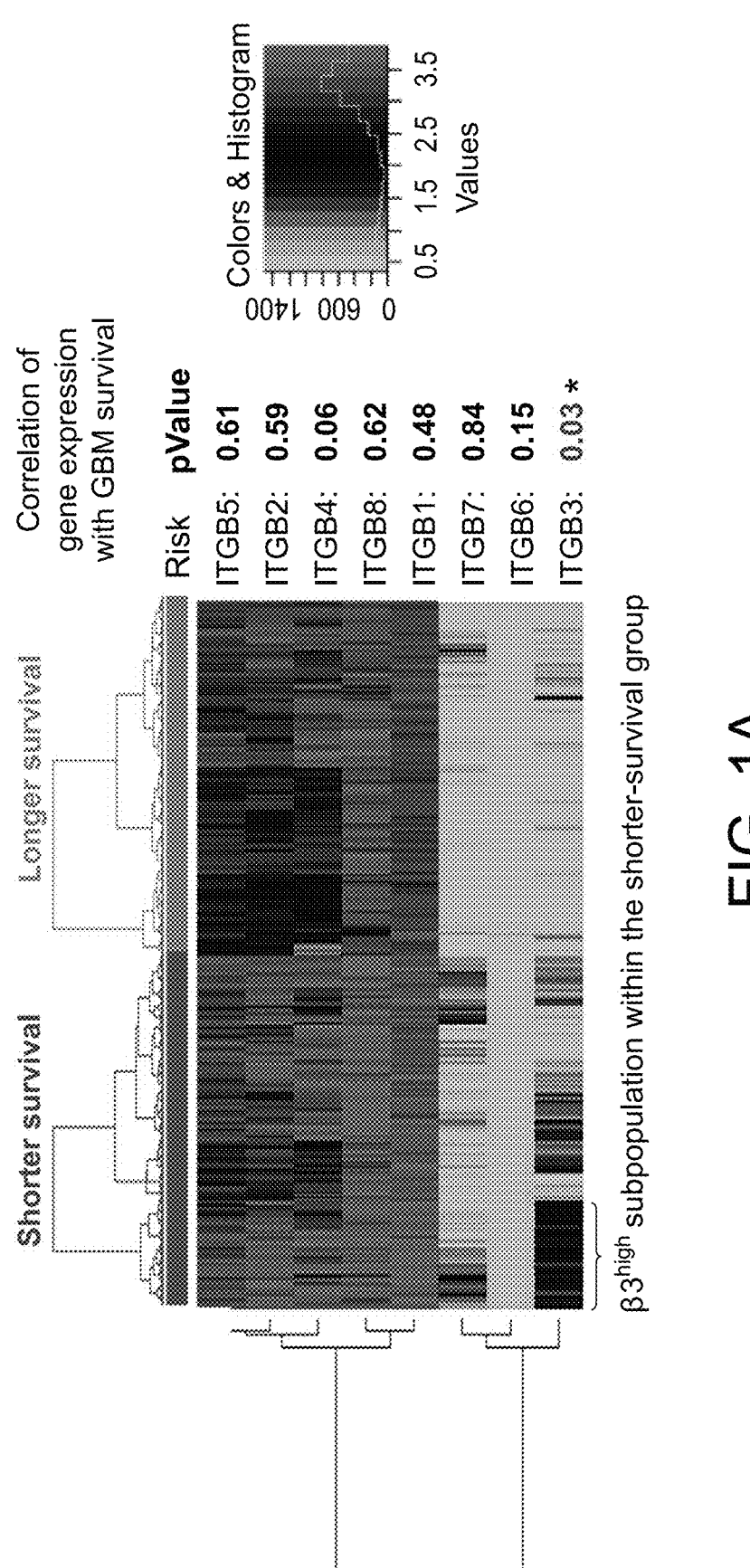
FIG. 1A-D illustrate $\beta 3$ levels correlate with poor survival in GBM and expression of genes involved in glucose metabolism.
Figures 1B, 1C:
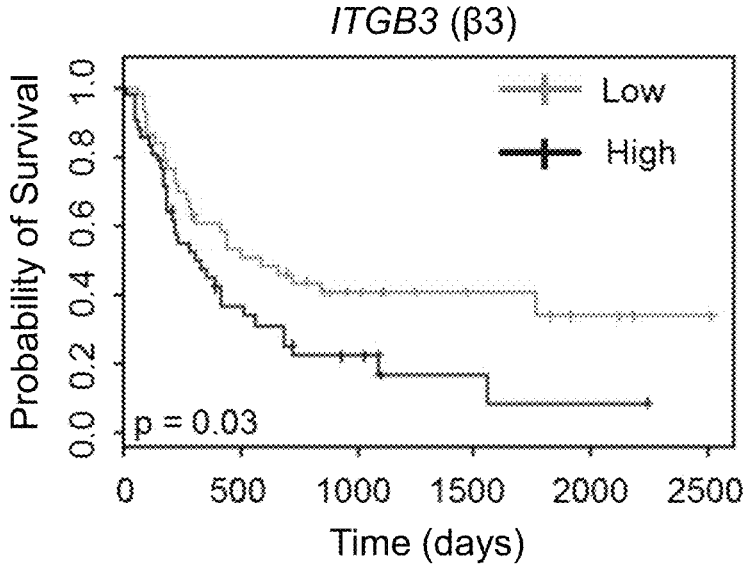

Integrin 3 mRNA Expression Correlates with Poor Survival and Expression of Genes Involved in Glucose Metabolism To investigate the clinical relevance of integrin expression in gliomas, we analyzed the correlation between integrin expression and glioma patient survival for the "Freije" dataset (Freije, Cancer Res, 2004). Expression of the integrin β subunit is a rate-limiting determinant of integrin heterodimer formation (Cheresh, 1987), and our analysis reveals ITGB3 (β3) as the only β subunit whose mRNA expression correlates with poor survival in gliomas (P-value=0.03) (FIG. 1A-1B). Because β3 pairs exclusively with the av subunit in GBM cells, this finding is consistent with our previous report of integrin αvβ3 protein expression in GBM, but not in low grade astroglial-derived tumors (Gladson and Cheresh, 1991). We also generated Kaplan-Meier curves from additional datasets, which confirm ITGB3 as a strong prognostic factor associated with poor patient survival, as shown in the Table illustrated in FIG. 7. By generating a hierarchical cluster and stratifying patients into two groups according to median survival, we identify a β3^{high} subset of samples within the shorter-survival group (FIG. 1A). We reasoned that understanding how integrin β3 contributes to the aggressive phenotype for this subpopulation would enable the design of a targeted therapy approach to exploit the vulnerabilities of this subset.

Figure 1D:
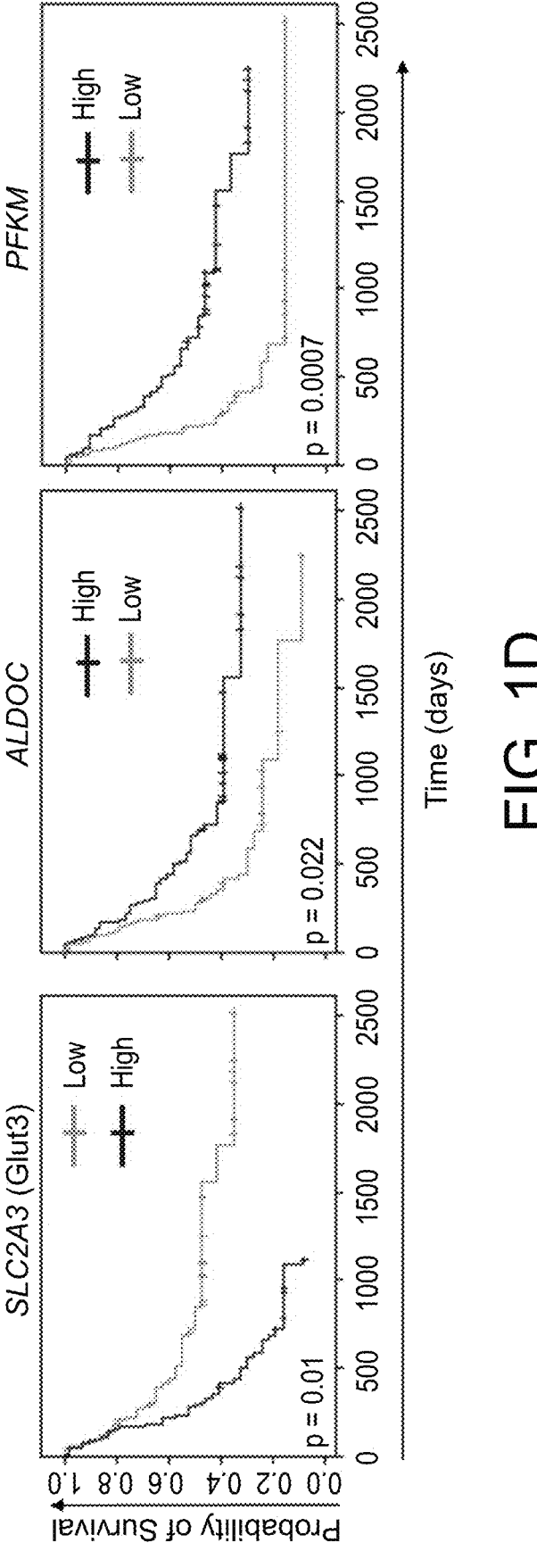

To consider how high integrin β3 expression may lead to poor survival in GBM, we compared gene expression profiles between B3^{high} versus β3^{low} samples in GBM patients. We find genes involved in glucose metabolism (ALDOC, PFKM and GLUT3) as one of the main family of genes correlated with β3 expression (FIG. 1C, supplementary table 2). As for integrin β3, Kaplan-Meier analysis indicates that poor survival correlates with high expression of GLUT3 (P-value=0.01) and low expression of ALDOC and PFKM (FIG. 1D).

To further validate the clinical relevance of this profile, we generated Kaplan-Meier curves from the "Lee" and "TCGA" datasets. Whereas ALDOC and PFKM do not consistently correlate with patient outcome, we find that GLUT3 expression tracks with poor survival for all datasets, see the table illustrated in FIG. 9. Moreover, analysis of multiple datasets reveals ITGB3 and GLUT3 as co-expressed genes not only in GBM, but also in other cancer types, as illustrated in FIG. 12A-E.

Figure 2A:
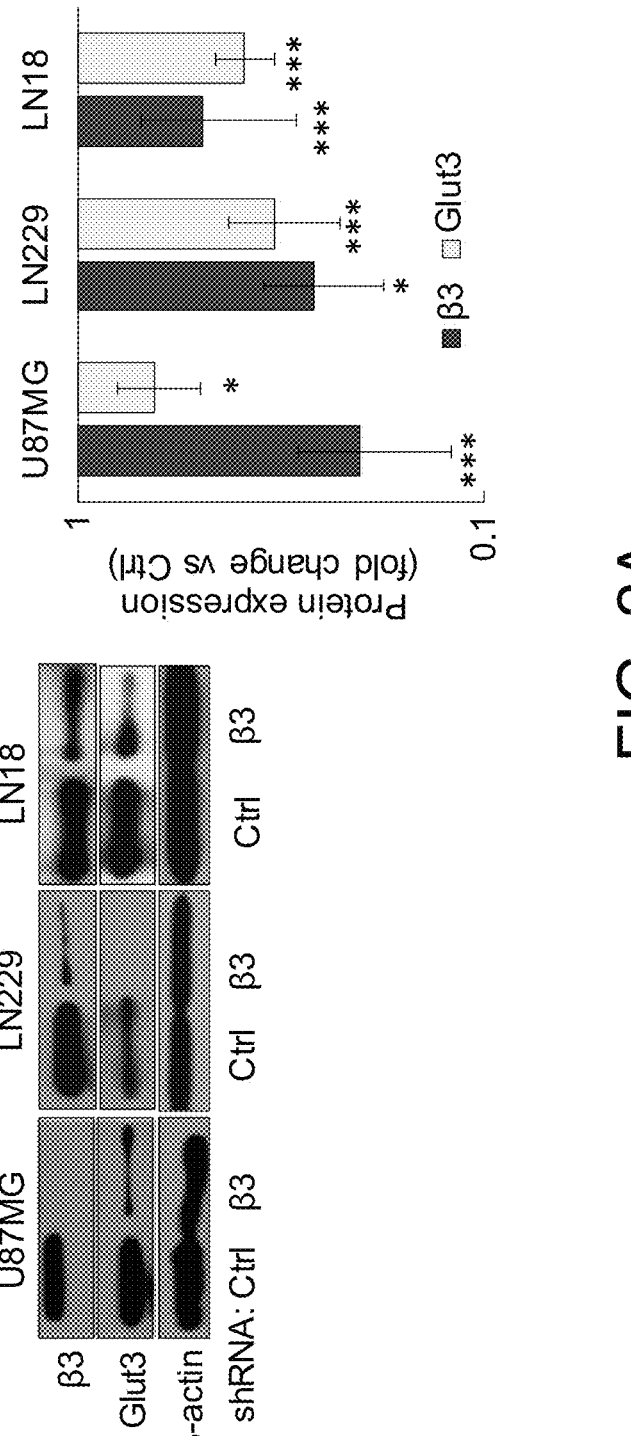
FIG. 2A-O: The impact of integrin $\alpha v\beta 3$ on GBM is attributed to its regulation of Glut3 expression.
Figure 2B:
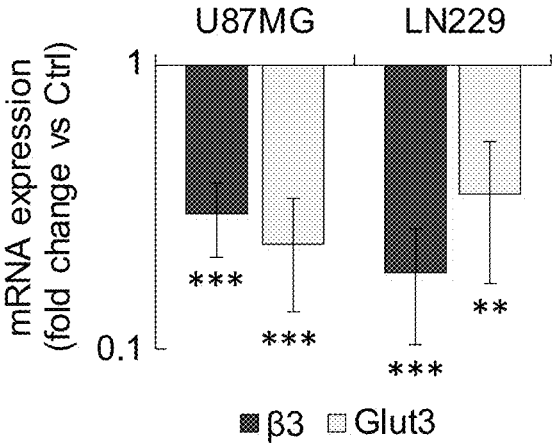
FIG. 2B graphically illustrates data of mRNA expression, which was determined by qPCR in U87MG, LN229 and LN18 infected by shRNA Control (shCtrl) or sh$\beta 3$.
Figure 2C:
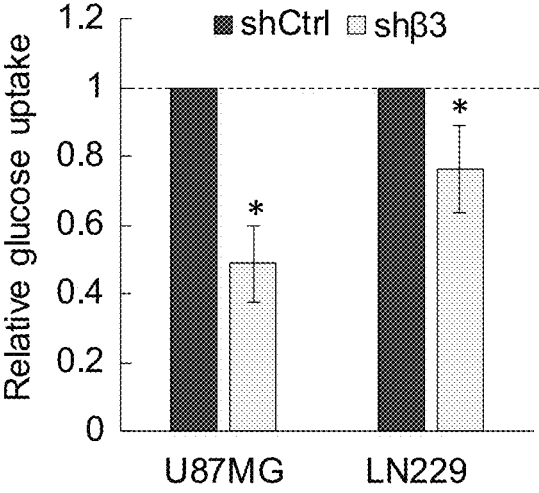
FIG. 2C graphically illustrates data showing the relative glucose uptake in U87MG, LN229 and LN18 cells with $\beta 3$ knockdown compared to control (shCtrl)
Figure 2D:
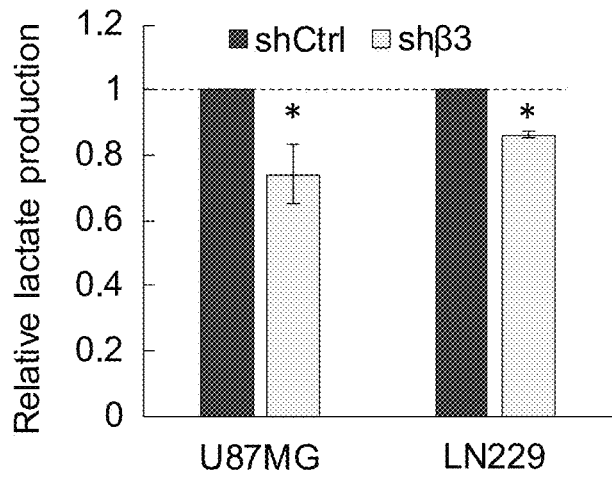
FIG. 2D graphically illustrates data where the bars represent the relative lactate production in U87MG and LN229 cells with $\beta 3$ knockdown compared to control (shCtrl)
Figure 2E:
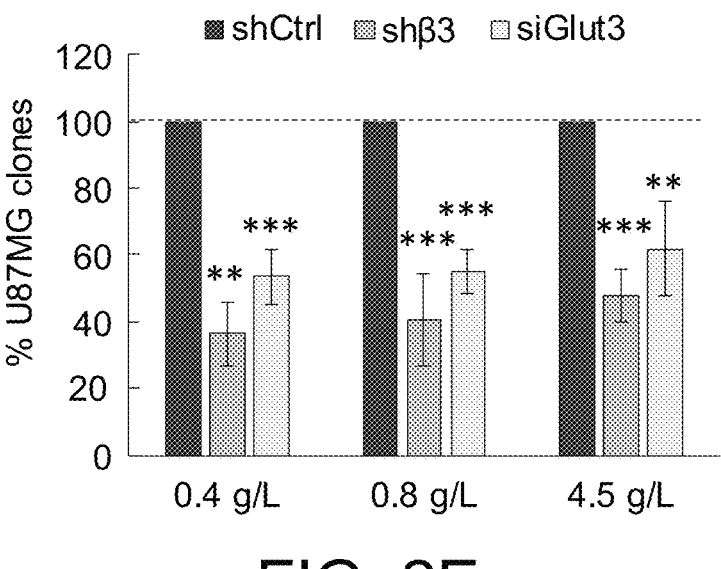
FIG. 2E graphically illustrates data showing the effect of $\beta 3$ and Glut3 knockdown on anchorage-independent growth of U87MG under high (4.5 g/l) or low (0.4 or 0.8 g/L) glucose conditions.
Figure 2F:
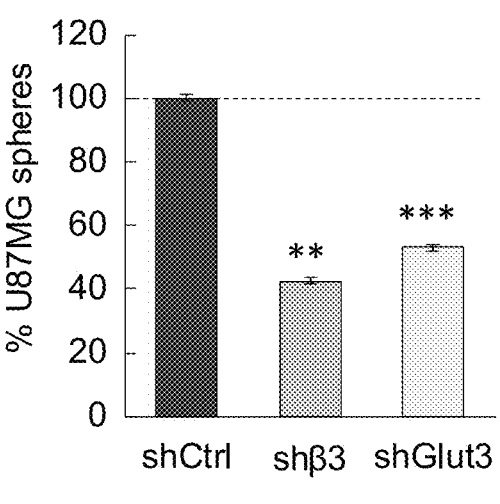
FIG. 2F graphically illustrates data showing the effect of $\beta 3$ and Glut3 knockdown on tumorsphere formation of U87MG under low glucose conditions (0.4 g/L)

Targeting 83 Strongly Inhibits Glut3 Expression to Decrease Cell Survival and Anchorage-Independence We next considered whether the ability of integrin αvβ3 to promote an aggressive GBM phenotype might be linked to Glut3-mediated cell survival and glucose uptake. For three established GBM cell lines, shRNA-mediated knockdown of integrin β3 strongly inhibits Glut3 expression (FIG. 2A-2B), glucose uptake (FIG. 2C), and lactate production (FIG. 2D). In fact, the effect of β3 knockdown on cell survival is accentuated under low glucose conditions (FIG. 2E and FIG. 13A). Indeed, we observe that knockdown of either β3 or Glut3 decreases anchorage independence (FIG. 2E) and tumorsphere formation (FIG. 2F).

Figure 2G:
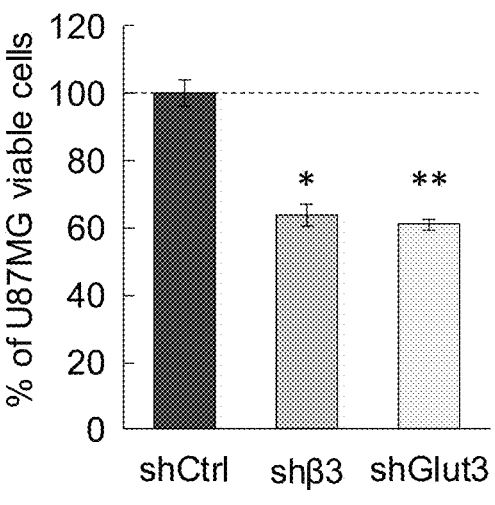
FIG. 2G graphically illustrates flow cytometry data, which was used to quantify $\beta 3^+$ versus $3^-$ as well as Glut3$^+$ versus Glut3$^-$ in a growth competition assay under low glucose conditions (0.4 g/L)
Figure 2H:
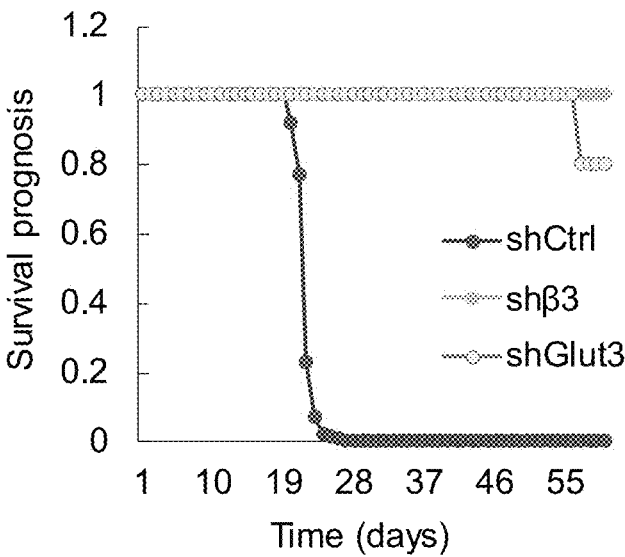
FIG. 2H graphically illustrates data showing the effect of $\beta 3$ and Glut3 knockdown on tumor growth in vivo: U87MG shCtrl and U87MG $\beta 3$ and Glut3 shRNA. (n=15 mice per group)
Figure 2L:
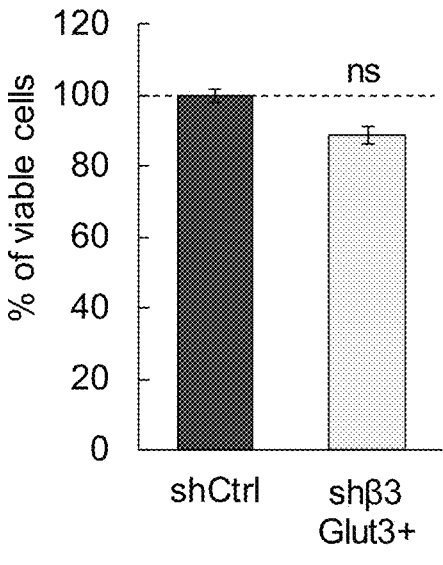
FIG. 2L graphically illustrates data of a flow cytometry analysis used to quantify U87MG shCtrl (GFP–) versus U87MG sh$\beta 3$-Glut3+ (GFP+) in a growth competition assay.
Figure 2M:
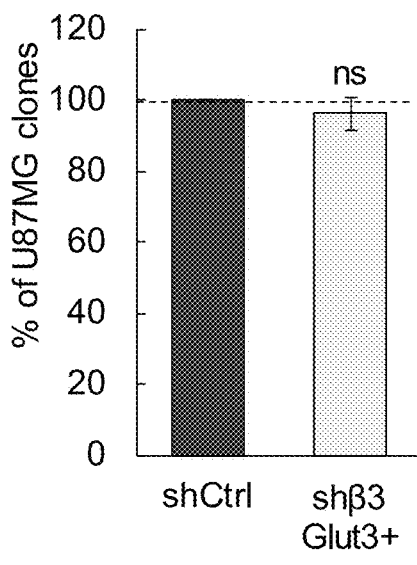
FIG. 2M graphically illustrates data showing the effect of ectopic expression of Glut3 on U87MG $\beta 3$ shRNA on anchorage-independence growth.
Figure 2N:
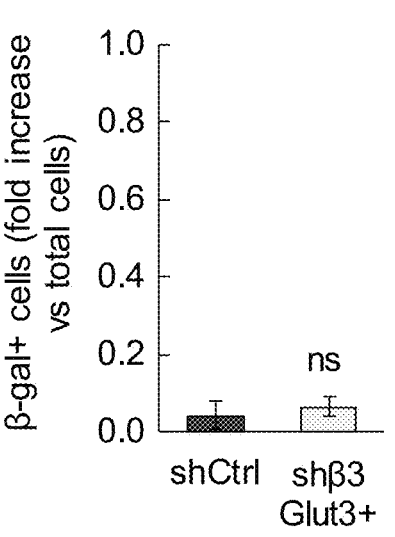
FIG. 2N graphically illustrates data showing the fold change of $\beta$-galactosidase positive cells versus the total cell number; inverted microscopy images of acidic senescence-associated β-galactosidase staining in U87MG β3 shRNA overexpressing Glut3 compare to U87MG shCtrl (n=5 fields counted per group); and, FIG. 2O graphically illustrates data showing the effect of ectopic expression of Glut3 on tumor growth in vivo: U87MG shCtrl and U87MG β3 and Glut3 shRNA. (n=15 mice per group)
Figure 2O:
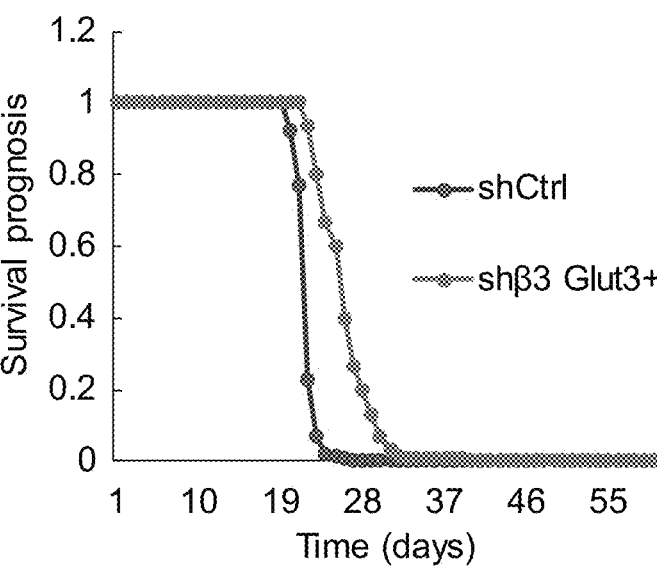

To determine whether highly efficient glucose uptake provides a competitive advantage for β3+ cells, we co-cultured β3+ (GFP−) and β3− (GFP+) cells under standard (4.5 g/L) or low (0.4 g/L) glucose conditions and monitored their ratio using flow cytometry. Indeed, there are significantly more viable β3+ cells present after 1 week of glucose restriction compared with cells for which either β3 or Glut3 had been knocked down (FIG. 2G). More importantly, knockdown of either β3 or Glut3 significantly delays the orthotopic growth of GBM tumors in mice (FIG. 2H and FIG. 13B). Collectively, these results indicate that β3 and Glut3 promote the survival of GBM cells.

We previously reported that knockdown of β3 induced a senescent phenotype in GBM cells (Franovic et al., 2015). Here we show that Glut3 knockdown also induces multiple markers of senescence in vitro, including β-galactosidase (SA-β-gal) activity and G0/G1 cell cycle arrest (FIG. 2I-2J). In vivo, cells with knockdown of either β3 or Glut3 show SA-β-galactosidase activity within subcutaneous xenografts (FIG. 2K). In contrast, knockdown of the Glut1 or Glut6 glucose transporters does not induce a senescent phenotype (FIG. 13C). We therefore asked whether ectopic expression of Glut3 is sufficient to drive GBM growth in the absence of β3. Indeed, ectopic Glut3 "rescues" the effects of β3 knockdown on 2D and 3D growth and prevents the senescent phenotype in vitro and in vivo (FIGS. 2K-2O and FIG. 13D), suggesting that the regulation of Glut3 expression may largely account for the impact of integrin αvβ3 on GBM progression.

Integrin αvβ3 Modulates Glut3 Expression Through PAK4-YAP TAZ Axis

To understand how integrin αvβ3 regulates Glut3 expression in GBM cells, we considered transcriptional regulators that correlate with β3 expression. We identified "cell signaling" as an important family of genes associated with β3 expression, see FIG. 8C, and found the transcriptional co-activator WWTR1 (WW domain-containing transcription regulator 1, also known as TAZ) as the top transcription factor in our list of genes, see FIG. 8A-C. Along with its paralog Yes-associated protein (YAP), YAP/TAZ impacts a wide variety of cellular functions, including epithelial-mesenchymal transition, cell growth, organ development, metabolism, and stress responses (Moroishi et al., 2015). Of note, the Kaplan-Meier curves generated from Freije (FIG. 3A) and TCGA (FIG. 14A) datasets reveal that WWTR1 (TAZ) expression correlates with poor survival (P-values=0.01 and 0.006 for Freije and TCGA datasets respectively). Moreover, we find that β3 knockdown leads to a marked decrease of YAP/TAZ expression (FIG. 3B-3C). Consistent with previous reports of Glut3 as a YAP-regulated gene (Wang et al., 2015), we find that YAP/TAZ knockdown decreases Glut3 expression (FIG. 3D-3E, FIG. 14B), and this also induces senescence as evidenced by SA-β-galactosidase activity (FIG. 3F). Furthermore, ectopic expression of YAP can rescue colony forming ability in B3-knockdown cells (FIG. 3G and FIG. 14E-G).

Since we recently implicated PAK4 as a mediator of β3 function in GBM cells (Franovic et al., 2015), we considered whether this kinase may also be required for β3-mediated regulation of YAP/TAZ expression. Indeed, inhibition of PAK4 activity using the PAK4 kinase inhibitor PF-03758309 or knockdown of PAK4 expression using shRNA led to a decrease of YAP/TAZ expression (FIG. 3H, FIG. 14C and FIG. 14E-G). Moreover, knockdown of PAK4 (like YAP/TAZ) induced markers of senescence, including SA-β-gal and G0/G1 cell cycle arrest (FIG. 3I-3J). Whereas a critical role for Glut3 in GBM has recently been reported (Flavahan et al., 2013), there have so far been no therapeutic agents capable of targeting its function. By understanding how Glut3 expression is regulated in GBM cells, our new findings highlight multiple strategies to therapeutically target this signaling axis in cells that are addicted to Glut3 for survival.

Integrin αvβ3 is Required for Glut3 Expression in Patient-Derived Gliomaspheres

To further examine the link between B3 and Glut3 in models that reflect the genetic heterogeneity of human glioblastoma, we derived glioblastoma stem cells (GSCs) from twelve GBM patients and confirmed tumorigenicity, multipotency capacity, and expression of stem cell markers (FIG. 15A-C). For this panel, a third of the GSCs models show high integrin β3 expression (FIG. 4A), and this correlates with positive expression of Glut3 (FIG. 4A). Similarly, histological analysis of a GBM tissue array confirms that only a subset of GBM specimens show high expression of both β3 and Glut3 (FIG. 15D-E). For the β3-positive GSC models on our panel, knockdown of β3 decreases Glut3 expression (FIG. 4B, FIG. 15F and FIG. 15I), while ectopic expression of β3 in the β3-negative GBM6 model induces both Glut3 and YAP expression (FIG. 15G). In contrast to this GSC panel, all of the GBM established cell lines examined show high levels of both αvβ3 and Glut3 (FIG. 2A and FIG. 15H), highlighting the inability of cultured cell lines to accurately reflect the heterogeneity of GBM in this context.

Patient-Derived Gliomaspheres Show Heterogeneity in Glut3 "Addiction"

In contrast to the established GBM cell lines that are uniformly addicted to both αvβ3 and Glut3, we find that not all of the αvβ3+/Glut3+ patient-derived GSC models are dependent on glucose and/or Glut3 expression for survival. While Ge479 and GBM39 are highly sensitive to glucose deprivation, other patient-derived GSCs show less sensitivity (Ge269 and Ge518) or glucose indifference (Ge738 and GBM6), as demonstrated by their equivalent viability under low or high glucose conditions (FIG. 4C). Importantly, Glut3 knockdown decreases the survival of the glucose-addicted Ge479 GSC model, while Ge269 and Ge518 are only moderately dependent on glucose and not dependent on Glut3 (FIG. 4A-D). For the glucose-addicted Ge479 model, β3 and Glut3 knockdown induces the same pattern of gene expression (increased ALDOC and a trend toward increased HK3), which is in line with the differential gene expression analysis (FIG. 4E). The apparent dichotomy in αvβ3/Glut3 expression vs. addiction prompted us to consider how the two groups of GSCs models may differ in terms of molecular subtype. Indeed, the Glut3-addicted GSCs models Ge479 and GBM39 express genes consistent with a "Proneural-Classical" GBM subtype (EGFR, GLI1, NES, DLL3, OLIG2), while the Glut3-independent GCS models Ge269 and Ge518 express markers indicating the Mesenchymal GBM subtype (CHI3L1 (YKL40), LOX, CD44, and RELB) (FIG. 16A). Altogether, our results indicate that within the population of GSCs defined by dual high expression of both αvβ3 and Glut3, only a subset of these tumors (i.e. those with Proneural-Classical marker) depend on Glut3 for survival.

The Mesenchymal Subtype of GBM is Enriched for Glycolytic Genes, but is Insensitive to Antagonists of the αvβ3 PAK 4 YAP TAZ Pathway GBM cells avidly take up glucose and are highly metabolically active. This particularity has been exploited clinically by Positron Emission Tomography (PET) combined with an intravenous injection of 18F-fluorodeoxy-glucose (18FDG), a glucose analog. However, not all GBM subtypes avidly take up FDG, suggesting metabolic heterogeneity which is not clearly understood. To investigate how αvβ3 might impact the metabolic landscape of GBM, we performed an enrichment analysis for all genes involved in the glycolytic/gluconeogenesis pathway. For the Mesenchymal subtype of GBM in the Freije dataset, there is a significant enrichment of genes involved in the glycolytic pathway, including HK3, LDHA, PFKL, PGK1, GLUT3, GLUT5, and GLUT10, a trend toward enrichment for HK2, ENO1, PFKM, GAPDH, and ALDOA, and significantly low expression of ALDOC, PFKP, and LDHB (FIG. 5A and FIG. 16B). Kaplan-Meier analysis confirms the clinical relevance for several of these genes (FIG. 5B and FIG. 16C-F). Despite the highly glycolytic expression signature of the Mesenchymal subtype in the Freije dataset and the enrichment of β3, Glut3, YAP, and TAZ (FIG. 5C), we find that Mesenchymal-like GSC models are not addicted to Glut3 (FIG. 4D). It is possible that the abundance of glycolytic genes can compensate for the role of Glut3, thus explaining its non-essential role in tumors of this subtype. Or, the Mesenchymal subtype may depend on metabolic pathways, other than the glycolytic pathway, for survival. Together, these findings suggest that agents targeting the αvβ3/PAK4/YAP/TAZ/Glut3 signaling axis would be most effective for αvβ3/Glut3$^{high}$ tumors that show markers defining a Proneural/Classical, but not Mesenchymal, subtype.

We hypothesized that αvβ3/Glut3$^{high}$, Glut3-addicted GSCs (GBM39 and Ge479) would be highly sensitive to agents that disrupt the β3-PAK4-YAP/TAZ axis. To test this hypothesis, we evaluated GSC survival in presence of the αv integrin antagonists cilengitide (a cyclic peptide that inhibits αv integrins) or LM609 (a monoclonal antibody specific for integrin αvβ3) (FIG. 5D and FIG. 5H). We found that sensitivity to any of these agents does not exclusively depend on αvβ3/Glut3 expression, but rather on Glut3/glucose addiction status, which appears to be linked to a Proneural-Classical like subtype. In contrast, GSC with low β3/Glut3 expression (Ge738, GBM6, Ge970.2 and Ge885) consistently showed a moderate enhancement of viability when treated with cilengitide or LM609 (FIG. 5D, FIG. 5H and FIG. 16G). Similar to blockade of αvβ3 directly, inhibitors of YAP or PAK4 reduce in vitro viability of the Glut3-addicted Proneural-like Ge479 GSC, but not the Glut3-independent Mesenchymal-like Ge518 model (FIG. 5E and FIG. 5H). Systemic cilengitide treatment prolongs the survival of mice bearing Ge479, but not Ge518, orthotopic tumors (FIG. 5F), further linking Glut3 addiction to a differential selectivity to αvβ3 antagonism in vivo.

Finally, we considered how the Glut3 addiction status of a given tumor might be predicted using molecular profiling. To do this, we identified samples from the Freije dataset with high expression of Glut3. For this subset, we asked which genes tracked with Glut3 in terms of patient survival. This generated a list of Glut3/survival-associated genes that we predicted might be useful in the identification of the Glut3 addicted phenotype, see the Table of FIG. 11. To validate this profile, we asked if this profile could differentiate between our Proneural/Classical Glut3-addicted GSC models (GBM39 and Ge479) and our Mesenchymal Glut3-non-addicted GSC models (Ge269 and Ge518). Out of a 115-gene panel, a 19-gene subset (FIG. 5G) allowed us to distinguish between Mesenchymal (LOX, THBS1, and DCN) and Proneural/Classical subtypes (DLL3, OLIG2, CDK17, and MAP2). Therefore, assessing GBM molecular subtype using this gene expression panel could provide a means to identify which αvβ3/Glut3$^{high}$ tumors should be sensitive to inhibitors of αvβ3/PAK4/YAP/TAZ or Glut3 knockdown (FIG. 5F).

To validate our hypothesis and test the ability of our signature to predict sensitivity to αvβ3 antagonists, we analyzed the available gene expression data for 41 models from the Mayo Clinic Brain Tumor Patient-Derived Xenograft National Resource. Based on their expression of genes associated with the Glut3 addicted versus non-addicted signature we generated, we predicted that 8 of the models (approximately 20%) should be sensitive based on their high expression of β3/Glut3 and the Glut3 addicted signature. We therefore obtained 3 models predicted to be addicted, 2 non-addicted, and 2 with β3/Glut3-low to directly test sensitivity to the αvβ3 antagonists cilengitide and LM609 (FIGS. 17A-B, FIGS. 8A-B, and FIG. 19). Similar to Ge479 and GBM39, we find sensitivity to integrin blockade for GBM14, 85 and 64, which we predicted to be Glut3 addicted (FIG. 17A-B). Consistently, GBM150 and GBM59 with Glut3 non-addicted signatures are not affected by the integrin antagonists. Like the other GSC with low β3/Glut3 expression, GBM26 and GBM12 show no effect or a moderate enhancement of viability upon cilengitide or LM609 treatment (FIG. 17A-B). Based on gene expression alone, we were able to predict whether a given GBM PDX model would be sensitive or insensitive to αvβ3 blockade for this collection of samples. Our success with a modest sample size suggests promise for expanding this strategy to clinical testing.

Notably, we also find that ectopic expression of β3 in a GCS in a model with low β3/Glut3 (GBM6) it is not sufficient to sensitize the tumor cells to integrin blockade, while B3 knockdown in the Glut3 addicted Ge479 model abolishes their sensitivity (FIG. 20).

More importantly, systemic treatment with the integrin antagonist cilengitide dramatically prolongs the survival of mice bearing Ge479, but not Ge518, orthotopic tumors (FIG. 21 and FIG. 22), further linking Glut3 addiction to a differential selectivity to αvβ3 blockade in vivo. Altogether, our results identify a molecularly defined subset of GBM tumors that are highly sensitive to inhibition of the β3-PAK4-YAP/TAZ axis by virtue of their Glut3 addiction (FIG. 5F and FIG. 6).

Discussion

Previous studies have linked αvβ3 expression to GBM progression (Gladson and Cheresh, 1991). Here, we reveal that integrin αvβ3 expression via activation of PAK 4 is required for Glut3 expression in GBM cells, which in some patients leads to Glut3 addiction and sensitivity to αvβ3 antagonists. Although all established GBM cell lines we examined express αvβ3 as a biomarker predicting both Glut3 addiction and sensitivity to inhibitors of αvβ3 integrin, PAK4 or YAP/TAZ, we find this holds true for only a subset of patient-derived gliomasphere models that may more accurately represent the genetic heterogeneity of GBM. Indeed, dual expression of αvβ3/Glut3 drives addiction to this pathway only for Proneural-Classical subtype GBM tumors. In contrast, elements of this pathway are not critical for the growth and viability of patient-derived gliomaspheres that show a gene signature consistent with the Mesenchymal GBM subtype. Thus, our findings provide a possible explanation for the failure of cilengitide to meet its primary survival endpoint in phase III trials, and we predict patients with αvβ3-positive Proneural-Classical subtype tumors might be the best candidates for this drug.

Integrin αvβ3 as a Target for GBM Therapy

While a number of integrins contribute to the growth and progression of a wide array of cancers (Desgrosellier and Cheresh, 2010; Desgrosellier et al., 2014; Seguin et al., 2014), we find that only αvβ3 expression is significantly linked to glioblastoma progression. This is consistent with our previous studies showing αvβ3 protein expression on the most advanced form of this disease, and most highly expressed on those cells at the tumor margin (Gladson and Cheresh, 1991). However, despite promising activity in phase I (Nabors et al., 2007) and II (Reardon et al., 2008) trials, the av integrin antagonist cilengitide failed to produce a significant overall survival benefit in the phase III CENTRIC trial (Stupp et al., 2014), and further clinical development of cilengitide for GBM has been halted (Mason, 2015).

A number of factors may have contributed to the clinical failure of cilengitide, including the stability and pharmacokinetic properties of the drug, its combination with alkylating agents, and use in highly aggressive, drug-resistant cancer (Paolillo et al., 2016). However, we argue it may be important to select a more focused GBM patient population. While higher levels of αvβ3 were associated with a modest survival benefit in the phase II CORE trial, αvβ3 expression did not correlate with outcome for the phase III CENTRIC trial (Weller et al., 2016). These findings, along with our new data, suggest that profiling αvβ3 expression alone is not sufficient to predict sensitivity to this drug. Instead, we have linked cilengitide sensitivity with the ability of αvβ3 to drive Glut3 addiction.

Understanding why Certain Tumors are Addicted to αvβ3, Glucose, and Glut3

Using loss/gain-of-function approaches, we have determined that integrin αvβ3 is required for expression of the high affinity glucose transporter, Glut3, in a PAK4 and YAP/TAZ-dependent manner. In turn, Glut3 appears to be a critical mediator of αvβ3 addiction in GBM, as ectopic Glut3 expression can completely rescue the orthotopic tumor growth capacity of β3-knockdown cells by allowing them to avoid senescence. While normal astrocytes do not express Glut3, its expression level correlates to astrocytoma grade (Boado et al., 1994). Previous studies have reported a correlation between glucose level/uptake and poor survival (Patronas et al., 1985), and Flavahan and colleagues reported that brain tumor initiating cells express Glut3, allowing them to outcompete non-tumor cells for glucose within the glucose-limited tumor environment (Flavahan et al., 2013). Recently, Birsoy and collaborators reported that certain glucose-sensitive cell lines do not increase oxygen consumption upon glucose limitation, and gene expression analysis revealed that these lines have low Glut3 and Glut1 expression (Birsoy et al., 2014). A recent single cell RNA-seq study highlighted the strong heterogeneity in GBM specimens that was not previously well appreciated (Patel et al., 2014); indeed, among all five tumors analyzed, the authors have shown individual cells corresponding to different GBM subtypes. Together, these studies suggest a complicated heterogeneity and metabolic landscape among individual GBM tumors that may not only explain clinical trial failures but also highlight the need to better understand GBM heterogeneity in order to design appropriate therapeutic regimens. Furthermore, the impact of intratumoral heterogeneity for ITGB3 expression on clinical outcomes represents a potential limitation of our study, as tumors with high overall ITGB3 expression may contain a subpopulation of cells with low ITGB3 and GLUT3. Together, these studies suggest a complicated metabolic landscape among individual GBM tumors.

Despite the functional advantages offered by Glut3 expression, we find that only a subpopulation of our patient-derived GSC models actually depend on glucose/Glut3 for their survival. In contrast, all GBM long-cultured cell lines express high level of Glut3 and are addicted to this transporter for survival. As such, long-term culture of established GBM cell lines may somehow enrich for this phenotype, providing a poor reflection of its frequency within the well-appreciated heterogeneity of GBM. The fact that only 15% of our patient-derived GSC models appear to be αvβ3/Glut3 addicted suggests a similar portion of patients might thus be sensitive to αvβ3 antagonists. In this respect, our study reinforces the need to carefully consider whether biomarkers and drug sensitivity established using cell-based models will relate to the heterogeneity of GBM Identification of Glucose Glut3 Addicted Tumors While we are able to determine glucose/Glut3 addiction status using cell viability assays, we also identify these cells based on a genetic phenotype. Indeed, we find that αvβ3-positive glucose/Glut3 addicted vs. non-addicted tumors can be differentiated in terms of a molecular GBM subtype. Specifically, the glucose/Glut3 addicted tumors represent a subpopulation within the Proneural and Classical subgroups and can be further delineated based on their stem cell behavior. In contrast, a subpopulation of tumors in the Mesenchymal group tend to be positive for αvβ3/Glut3, yet surprisingly are not addicted to Glut3 and remain insensitive to αvβ3 antagonists. Thus, we estimate that 10-20% of GBM patients may show very significant responses to agents targeting αvβ3/Glut3. Indeed, a number of individual patients showed very significant, durable, yet unexplained responses to cilengitide (Nabors et al., 2007; Reardon et al., 2008). In the Mesenchymal subtype, we found an abundance of glycolytic genes and we found that all Mesenchymal patient-derived cells non-addicted to Glut3. Thus, the role of Glut3 may be negligible when other glycolytic genes are highly-expressed. Or, this subtype might be addicted to another glycolytic gene product, as suggested by Mao and co-workers (Mao P., 2013). At present, it is unclear why certain GBM tumors are, and/or become, addicted to Glut3, while others can circumvent this dependence.

Broader Implications for GBM Therapeutics

We report that among αvβ3/Glut3-expressing tumors, only a subpopulation is "addicted" to glucose/Glut3. Not only does this phenotype render them particularly sensitive to αvβ3 integrin inhibitors (including av integrin-targeting cyclic peptide cilengitide or the monoclonal αvβ3 antibody LM609), but we show that such tumors are also sensitive to PAK4 as well as YAP/TAZ inhibitors which suppress αvβ3-mediated Glut3 expression in GBM cells. While the importance of YAP/TAZ in GBM aggressiveness has been reported, our new findings provide some insights in its regulation, signaling, and function within a molecularly defined GBM subpopulation.

Aside from cilengitide, there are a number of αvβ3-targeted strategies in development for GBM, including GLPG0187, a small molecule antagonist of multiple integrins including αvβ3, αvβ5, αvβ6, and α5β1 (Cirkel et al., 2016), as well as approaches that use RGD peptides for αvβ3-targeted delivery of radionuclides (Jin et al., 2017), siRNA (He et al., 2017), and chemotherapy-loaded nanoparticles or nanogels (Chen et al., 2017; Fang et al., 2017). Considering that Glut3 addiction is also a feature of GBM cancer stem cells (Flavahan et al., 2013), targeting this phenotype with an αvβ3 antagonist has the potential to eradicate the most aggressive and drug resistant subpopulation within the tumor.

Figure Legends

FIG. 1. B3 levels correlate with poor survival in GBM and expression of genes involved in glucose metabolism:

(A) Hierarchical clustering of integrin β subunit expression correlated to a risk score predicting the patient survival.

(B) Kaplan-Meier analysis of Freije dataset for ITGB3
(B3) expression (n=42 B3 low, n=43 B3 high; P-value
(p)=0.03).

(C) Functional annotation clustering (series GSE4412) of
gene set enrichment analysis based on β3$^{high}$ versus
β3$^{low}$ expression. Graph shows the percent enrichment
for each family of genes.

(D) Kaplan-Meier analysis of Freije dataset for SLC2A3
(Glut3), ALDOC and PFKM expression. SLC2A3
(n=42 Glut3 low, n=43 Glut3 high; P-value=0.01);
ALDOC (n=43 ALDOC low, n=42 ALDOC high;
P-value=0.022); PFKM (n=43 PFKM low, n=42 PFKM
high; P-value=0.0007). See also figure S1, table S1, S2
and S3.

FIG. 2. The impact of integrin αvβ3 on GBM is attributed
to its regulation of Glut3 expression:

(A) Immunoblots show expression of indicated proteins
for U87MG, LN229 and LN18 GBM cells infected by
shRNA Control (Ctrl) or shβ3. Graph shows the fold
change of protein expression determined by densitom-
etry analysis.

(B) mRNA was determined by qPCR in U87MG, LN229
and LN18 infected by shRNA Control (shCtrl) or shβ3.

(C) Relative glucose uptake in U87MG, LN229 and LN18
cells with β3 knockdown compared to control (shCtrl).

(D) Bars represent the relative lactate production in
U87MG and LN229 cells with β3 knockdown com-
pared to control (shCtrl).

(E) Effect of β3 and Glut3 knockdown on anchorage-
independent growth of U87MG under high (4.5 g/l) or
low (0.4 or 0.8 g/L) glucose conditions.

(F) Effect of β3 and Glut3 knockdown on tumorsphere
formation of U87MG under low glucose conditions
(0.4 g/L).

(G) Flow cytometry was used to quantify β3$^{+}$ versus β3$^{+}$
as well as Glut3$^{+}$ versus Glut3$^{-}$ in a growth competition
assay under low glucose conditions (0.4 g/L).

(H) Effect of β3 and Glut3 knockdown on tumor growth
in vivo: U87MG shCtrl and U87MG β3 and Glut3
shRNA. (n=15 mice per group).

(I) Graph represents the fold change of β-galactosidase
positive cells versus the total cell number. Inverted
microscopy images of acidic senescence-associated
β-galactosidase staining in U87MG shCtrl and U87MG
β3 and Glut3 shRNA (n=5 fields counted per group).

(J) Cell-cycle analysis showing the percentage of cells in
G0/G1, S, and G2/M in U87MG cells with β3 and
Glut3 knockdown.

(K) Images show acidic senescence-associated β-galac-
tosidase staining, a marker of senescence, in mice
implanted with U87MG shCtrl, shβ3, shGlut3, or shβ3
with ectopic expression of Glut3.

(L) Flow cytometry was used to quantify U87MG shCtrl
(GFP−) versus U87MG shβ3-Glut3+ (GFP+) in a
growth competition assay.

(M) Effect of ectopic expression of Glut3 on U87MG β3
shRNA on anchorage-independence growth.

(N) Graph represents the fold change of β-galactosidase
positive cells versus the total cell number. Inverted
microscopy images of acidic senescence-associated
β-galactosidase staining in U87MG β3 shRNA over-
expressing Glut3 compare to U87MG shCtrl (n=5
fields counted per group).

(O) Effect of ectopic expression of Glut3 on tumor growth
in vivo: U87MG shCtrl and U87MG β3 and Glut3 shRNA. (n=15 mice per group). This experiment was
performed at the same time as the in vivo experiment
shown in FIG. 2H.

Data are represented as mean (n=3-5)±SEM (*p<0.05,
p<0.01 and *p<0.001). See also FIG. 13.

FIG. 3. β3 modulates Glut3 expression through PAK4-
YAP/TAZ axis:

(A) Kaplan-Meier analysis of Freije dataset for TAZ
expression (n=42 for β3 low and n=43 for β3 high;
P=0.03).

(B) Immunoblots show the effect of β3 knockdown on
protein expression of YAP and β3. Bars represent the
fold change of protein expression determined by den-
sitometry analysis. Data are represented as mean (n=3-
5)±SEM (*p<0.05, p<0.01 and *p<0.001).

(C) Graph shows the effect of β3 knockdown on mRNA
expression of YAP and TAZ determined by qRT-PCR,
displayed as fold change for gene expression normal-
ized to sh-control in U87MG (n=3), LN229 (n=3) and
U251 (n=2).

(D) Immunoblots show the effect of YAP/TAZ knock-
down on Glut3 protein expression, and the graph shows
the fold increase determined by densitometry analysis.
U87MG (n=3), LN229 (n=3) and U251 (n=2).

(E) Graph shows the effect of YAP/TAZ knockdown on
mRNA expression for Glut3, YAP and TAZ determined
by qRT-PCR, displayed as fold change of gene expres-
sion normalized to sh-control.

(F) Acidic senescence-associated β-galactosidase staining
in U87MG shCtrl versus YAP/TAZ shRNA.

(G) Effect of ectopic expression of YAP on U87MG β3
shRNA on anchorage-independent growth.

(H) Graph shows the fold change of protein expression in
U87MG (n=2) and LN229 (n=2) determined by den-
sitometry analysis.

(I) Acidic senescence-associated β-galactosidase staining
in U87MG shCtrl and PAK4 siRNA (n=3).

(J) Cell-cycle analysis showing the percentage of cells in
G0/G1, S, and G2/M in U87MG cells with PAK4
siRNA (n=3).

Data are represented as mean (n=2-5)±SEM (*p<0.05,
p<0.01 and *p<0.001). See also FIG. 13.

FIG. 4. Integrin αvβ3 is required for Glut3 expression in
patient-derived gliomaspheres that show heterogeneity in
Glut3 "addiction":

(A) Representative immunoblots show expression of β3,
Glut3, and TAZ in GSCs with a schematic representing
the decision tree for selecting GSCs based on β3/Glut3
expression (n=2).

(B) Immunoblots show effect of β3 knockdown on
expression of indicated proteins in Ge479 (n=3). Graph
represents the fold change of protein expression rela-
tive to sh-control determined by densitometry analysis.

(C) Effect of glucose concentration on cell viability
measured by CELLTITER-GLO™ in GSCs (n=3-5).

(D) Effect of Glut3 knockdown on cell viability measured
by CELLTITER-GLO™ in GSCs (n=3-4).

(E) Expression of glycolytic, pentose phosphate and mito-
chondrial oxidative phosphorylation (OXPHOS)
related genes were determined by qRT-PCR after β3 or
Glut3 knockdown in Ge479. Bars show the fold change
of gene expression normalized to sh-control. See also
figure S4.

FIG. 5. The mesenchymal subtype of GBM is enriched for
genes involved in glycolytic pathway and sensitive to αvβ3
antagonists, YAP and PAK4 inhibitors:

(A) Enrichment analysis of glycolytic genes for the Freije dataset. Compared to other subtypes (Other sub), the Mesenchymal subtype showed high expression of Glut3, HK3, PFKP, PGK1, LDHA, Glut5 and Glut10, and no or low expression of LDHB, PFKP and ALDOC.

(B) Kaplan-Meier analysis of Freije dataset for PGK1 expression (n=42 for β3 low and n=43 for β3 high; P=0.00000007).

(C) Enrichment analysis for β3, Glut3 (also found in FIG. 5A), YAP and TAZ.

(D) Effect of LM609 (αvβ3 function blocking antibody) and cilengitide (cyclic peptide antagonist of av integrins including αvβ3 and αvβ5) on cell viability measured by CELLTITER-GLO™ in GSCs.

(E) Effect of YAP inhibitor (Verteporfin) or PAK4 inhibitor (PF-03758309) on cell viability measured by CELLTITER-GLO™ in GSCs.

(F) Illustrates a schematic depicting the proposed model of Glut3 addiction in GBM. In contrast to established GBM cell lines that are uniformly B3/Glut3high and Glut3 addicted, patient-derived GSC models show heterogeneity in expression of β3/Glut3. Importantly, the population of β3/Glut3high GSC models can be further separated into Glut3 addicted vs. Glut3 non-addicted subsets based on a gene signature and/or molecular subtype. Only the β3/Glut3high GSC models with Proneural/Classical subtype markers are sensitive to inhibitors that target elements of the αvβ3/PAK4/YAP pathway.

(G) Schematically illustrates data identifying Glut3 addicted vs. Glut3 non-addicted samples using 96 signature genes. mRNA was determined by qRT-PCR (n=2) and Bio-Rad software has been used for analysis. Only the most significant genes are shown.

(H) Effect of LM609 (αvβ3 function blocking antibody) and cilengitide (cyclic peptide antagonist of av integrins including αvβ3 and αvβ5) on cell viability measured by CELLTITER-GLO™ in GSCs (n=3-5).

(I) Effect of YAP inhibitor (Verteporfin) or PAK4 inhibitor (PF-03758309) on cell viability measured by CELLTITER-GLO™ in GSCs (n=3-5).

Data are represented as mean (n=3-5)±SEM (*p<0.05. p<0.01 and *p<0.001). See also FIG. 16.

FIG. 6. Glut3 addiction has a molecularly defined signature: Glut3 addicted vs Glut3 non-addicted samples were identified using 115 signature genes, and FIG. 6 illustrates a schematic depicting an exemplary model of Glut3 addiction in GBM. FIG. 8A-B: Illustrates a table showing a list of genes that are differentially expressed based on β3$_{high}$ versus 33$_{low}$ expression for the Phillips (FIG. 8A) and Sun (FIG. 8B) datasets. Only the top 120 genes are shown, ranked from 1 to 120. Only genes with P<0.05 were considered for analysis.

FIG. 11: Illustrates an exemplary list of genes defining Glut3 addicted vs non-addicted signature. Only genes with adjusted p-value<0.01 have been considered for analysis. Genes highlighted in blue have been validated by qRT-PCR. Numbers highlighted in orange indicate genes consistent with GBM subtypes.

FIG. 12. β3 and Glut3 expression are correlated in several datasets.

FIG. 13. Relative to FIG. 2.

(A) Effect of β3 knockdown on U87MG, LN229 and LN18 cell viability in high (4.5 μg/L) vs low (1 μg/L) glucose measured by Alamar blue.

(B) Histological analysis of U87MG cells with shCtrl and shGlut3. Mice bearing U87MG shβ3 do not develop tumors. Tumors were stained for haematoxylin and eosin (H&E), 3 and Glut3.

(C) Cell cycle analysis showing the percentage of cells in G0/G1, S, and G2/M for U87MG cells with knockdown of Glut1 or Glut6.

(D) Histological analysis of U87MG with shCtrl or β3 shRNA along with ectopic expression of Glut3 (Glut3+). Tumors were stained for haematoxylin and eosin (H&E), β3 and Glut3.

(E) Graph represents the fold change of β-galactosidase positive cells versus the total cell number. Inverted microscopy images of acidic senescence-associated β-galactosidase staining in LN229 and LN18 Ctrl, 33 and Glut3 siRNA (n=5 fields counted per group) (n=3).

(F) Cell-cycle analysis showing the percentage of cells in G0/G1, S, and G2/M in LN229 and U251 cells with 33 and Glut3 knockdown (n=3).

(G) Flow cytometry was used to quantify γH2AX expression in LN229 cells with 3 and Glut3 knockdown. The graph shows the fold increase of γH2AX expression (n=2).

(H) Immunoblots show expression of 33 and Glut3 in U87MG with shCtrl, shGlut3 or 33 shRNA along with ectopic expression of Glut3 (Glut3+) (n=3-4). The graph shows the fold change determined by densitometry analysis. Data are represented as mean (n=3-5) ±SEM (*p<0.05, p<0.01 and *p<0.001).

FIG. 14. TAZ expression is correlated with poor survival and effect of YAP and PAK4 inhibitors, related to FIG. 3.

(A) Kaplan-Meier analysis of TCGA dataset for WWTR1 (TAZ) expression (n=269 β3 low, n=2639 β3 high; P=0.006).

(B) Effect of YAP inhibitor, Verteporfin on its target genes (CTGF and CYR61). Expression of CTGF, CYR61 and Glut3 were determined by qRT-PCR in LN229 (n=3) and U87MG (n=2). Graph shows the fold change for gene expression normalized to control.

(C) Effect of PAK4 inhibitor, PF-03758309 on the phosphorylation of PAK4 (pPAK4). Representative immunoblots show effect of PF-03758309 on expression of indicated proteins in U87MG (n=2).

(D) Graphically illustrates the effect of genetic knockdown of PAK4 on mRNA expression of Glut3, YAP, and integrin β3 for the LN229 and U87MG GBM cell lines. Graph shows the fold change for gene expression normalized to control siRNA.

(E) Representative immunoblots show expression of β3 and YAP in U87MG with shCtrl, shβ3, and shβ3 along with ectopic expression of YAP (YAP+) (n=2).

(F) Effect of PAK4 inhibitor, PF-03758309 on the phosphorylation of PAK4 (pPAK4). Representative immunoblots show effect of PF-03758309 on expression of indicated proteins in Ge479 (n=2-3).

(G) Effect of PAK4 knock down on indicated proteins in U87MG (n=2) and LN229 (n=2).

FIG. 15. GSCs are tumorigenic and multipotent, related to FIG. 4.

(A) Representative light micrograph showing H&E staining for Ge518 GSCs-derived tumor in immune-compromised mice (n=3). GSCs show invasive phenotype (right panel, top) and necrotic foci (right panel, bottom).

(B) GSCs are multipotent and can differentiate to form neurons (βIIITubulin) and astrocytes (GFAP). DAPI was used for nuclear counterstaining.

(C) GSCs express cancer stem cell markers (CD133, Oct4 and Nanog). mRNA expression were determined by qPCR in all GSCs and normalized to housekeeping genes (HKGs).

(D-E) Histological analysis of brain GBM tissue array (GL805c). Bar graphs represent β3 and Glut3 expression level detected on tumor cells for 70 specimens (D). Tumors were stained for haematoxylin and eosin (H&E), β3 and Glut3 (E).

(F) β3, TAZ and YAP mRNA were determined by qPCR for Ge479 (n=3).

(G) Representative immunoblots showing expression of indicated proteins when ectopically expressed β3 is GBM6 (n=2).

(H) β3 and Glut3 expression was determined by qPCR in all GBM lines.

(I-J) Graphically illustrate data showing the effect of 33 (FIG. 15I) and Glut3 (FIG. 15J) knockdown on mRNA expression of ITGB3 (β3) and SLC2A3 (Glut3) determined by qRT-PCR, displayed as fold change for gene expression normalized to siCtrl in Ge518, Ge269 and Ge479 (n=2-4).

FIG. 16. GSCs classification and enrichment analysis of glycolytic genes, relative to FIG. 5 and FIG. 10.

(A) mRNA was determined by qPCR in all GSCs. Several genes (listed in table 4) have been tested for each GBM subtypes. An enrichment score has been determined according to gene expression normalized to housekeeping genes.

(B) Enrichment analysis of glycolytic genes (HK2, ENO1, PFKM, GAPDH and ALDOA).

(C-F) Kaplan-Meier analysis of Freije dataset for (B) PFKL expression (n=42 β3 low, n=43 β3 high; P=0.041); (C) LDHA expression (n=42 β3 low, n=43 β3 high; P=0.006); (D) LDHB expression (n=42 β3 low, n=43 β3 high; P=0.03) and (E) GAPDH expression (n=42 β3 low, n=43 β3 high; P=0.008).

FIG. 17: (A) Schematic depicting Mayo Clinic sample request. Samples were requested based on their Glut3 addicted vs. non-addicted signature, and then analyzed for cell viability in presence of cilengitide and LM609; and, (B) Effect of LM609 (αvβ3 function blocking antibody) and cilengitide (cyclic peptide antagonist of av integrins including αvβ3 and αvβ5) on Mayo Clinic GSCs cell viability measured by CELLTITER-GLO™ (CellTiter-Glo) in GSCs (n=3-5, except n=2 for GBM150 and GBM85).

FIG. 18: Illustrates a table showing Glut3 addicted vs non-addicted signature for Mayo Clinic GSCs extracted from Next Generation Sequencing (NGS) data. M=Mesenchymal, C=Classical, P=Proneural and N=Neural.

FIG. 19: Illustrates the relative normalized expression of various mRNAs (as indicated in the Figure) in Glut3 addicted and Glut3 non-addicted samples, as determined by qRT-PCR (n=2), and Bio-Rad software has been used for analysis.

FIG. 20: (A) Effect of LM609 (αvβ3 function blocking antibody) and cilengitide (cyclic peptide antagonist of av integrins including αvβ3 and αvβ5) on cell viability of Ge479 knockdown for β3, PAK4 and YAP/TAZ measured by CELLTITER-GLO™ in GSCs (n=3-5). For Ge479 parental, the same data are displayed FIG. 5H; (B) Effect of LM609 (αvβ3 function blocking antibody) and cilengitide (cyclic peptide antagonist of av integrins including αvβ3 and αvβ5) on cell viability of GBM6 with ectopic expression of 33 measured by CELLTITER-GLO™ in GSCs (n=3-5). For GBM6 parental, the same data are displayed FIG. 5H.

FIG. 21: Graphically illustrates data showing the effect of Cilengitide on tumor growth. Mice bearing orthotopic Ge518 (Glut3 non-addicted) and Ge479 (Glut3 addicted) brain tumors were treated with vehicle or cilengitide (25 mg kg-1; 8 mice per group). Data are represented as mean (n=3-5)±SEM (*p<0.05, p<0.01 and *p<0.001).

FIG. 22: Illustrates images of histological analysis of Ge518 and Ge479 xenografts. Ge518 (n=2-3 mice) and Ge479 (n=3-4 mice) tumors were stained for haematoxylin and eosin (H&E), β3 (brown), Glut3 (blue) and CD31 (brown). Scale bar, 50 μm.

Tables

FIG. 7. β3 expression consistently predicts poor survival among several GBM datasets (Freije, Lee and TCGA).

FIG. 8C. List of genes differentially expressed based on $β3^{high}$ versus $β3^{low}$ expression. Only the top 180 genes are showed, ranked from 1 to 180. Only genes with a P-value <0.05 have been considered for analysis.

FIG. 9. Correlation between ALDOC, PFKM and Glut3 expression with GBM patient survival among several GBM datasets (Freije, Lee and TCGA).

FIG. 10. List of primers used for qRT-PCR.

FIG. 11. List of genes defining Glut3 addicted vs non-addicted signature. Only genes with a P-value <0.01 have been considered for analysis.

Material and Methods:

Cell Culture. GBM cell lines were cultured in DMEM supplemented with 10% fetal bovine serum, L-glutamine and antibiotics. All cell lines were routinely tested for mycoplasma. Ge269, 479, 518, 688, 738, 835, 885, 898, 904, 970.2 were gifts from Dr. Valérie Dutoit and Dr. Pierre-Yves Dietrich to Dr E. Cosset and cultured in DMEM/F12 with Glutamax supplemented with B27 supplement and b-FGF, EGF both at 10 ng/ml with antibiotics (GSC medium). GBM6 and GBM39 were gifts from Dr. Paul Mischel and cultured in GSC medium.

Chemicals. Verteporfin (YAP inhibitor) was purchased from Sigma and used at the concentration of 0.5-10 μM for 24 hours. PF-03758309 (PAK4 inhibitor) was purchased from Chemietek and used at the concentration of 50 nM-1000 nM for 24 hours.

Isolation and cultivation of gliomaspheres and GBM cells. Isolation of glioblastoma-initiating cells was performed as described (Cosset et al., 2016). Briefly, viable fragments of high-grade human GBM were transferred to a beaker containing 0.25% trypsin in 0.1 mM EDTA (4:1) and slowly stirred at 37° C. for 30-60 minutes. Dissociated cells were split and some of them were plated in 75-cm² tissue culture flasks at 2,500-5,000 cells per cm²) in DMEM/F-12 medium (1:1) containing N2 and B27 supplements (all from Invitrogen, Carlsbad, CA, http://www.invitrogen.com) supplemented with bFGF and EGF both at 10 ng/ml (Invitrogen). Once established, GSCs were maintained in GSC medium.

Multipotency. GSCs were plated on coverslips coated with poly-L-ornithine and were grown in DMEM complete medium for 2 weeks. Cells were fixed in 4% PFA and incubated overnight with the following antibodies: GFAP (Sigma-Aldrich) and anti-β-Tubulin (Covance). After washing, anti-mouse Alexa565 and anti-rabbit Alexa 488 were used as secondary antibodies. Nuclei were counterstained with DAPI. Image acquisition was done with a NIKON ECLIPSE C1™ Confocal microscope.

Soft agar assay. 4000 cells were seeded in 48-well plates containing 0.3% agar/DMEM medium no glucose with 10% dialyzed FBS on top of a bottom layer of 1% agar. 200 μl of additional DMEM medium with 10% dialyzed FBS±glucose (0-4.5 g/L) was added, and cells cultured for 15 days. Colonies were stained with 0.1% crystal violet/20% methanol/PBS and counted.

Cell viability assay. U87MG, LN229, and LN18 cells were seeded at 1K cells per well in black 96-well plates in DMEM medium (no glucose) with 10% dialyzed FBS±glucose (0-4.5 g/L). Cell viability was determined by Alamar Blue dye (Life Technologies) according to manufacturer's instructions. For GSCs, cells were seeded at 10K cells per well in white 96-well low attachment plates in GSC medium±glucose (0-4.5 g/L). Viable cell numbers were evaluated using a CELLTITER-GLO™ assay kit (Promega). Each condition consisted of, at least, three replicate wells and data were expressed as relative luciferase units or as the percentage of survival of control cells.

Cell transfection (small interfering RNA and plasmids). siRNAs against β3, Glut3, Glut1, Glut6 or PAK4 were transfected using lipofectamine 2000 (Invitrogen), a final concentration of 5 nM. Two non-targeting scramble siRNAs (Life Technologies) were used as control. The pcDNAGlut3 plasmid were kindly provided by Dr. Yosuke Maeda (Kumamoto University) and were transfected using Lipofectamine 3000 (Invitrogen). The transfection efficiency was monitored by qRT-PCR and/or immunoblotting. All transfections were performed according to the manufacturer's protocols.

Genetic knockdown and expression constructs. Cells were infected with shRNAs for vector control (shCtrl, Open Biosystems), Glut3 (Santa Cruz Biotechnology), β3 and PAK4 (Open Biosystems) or YAP/TAZ (provided by Dr. K-L Guan) using a lentiviral system. pLENTIβ3 was obtained by subcloning the human β3 cDNA of pENTRβ3 vector in the pLENTI expression vector. pRETROYAP was kindly provided by Dr. K-L Guan. Gene silencing or overexpressing was confirmed by either immunoblot analysis or qPCR analysis.

Tumorsphere formation assay. 1K cells were seeded in low attachment plates in DMEM with Glutamax supplemented with B27 supplement, 20 ng/ml of bFGF and EGF, and glucose (0.4-4.5 g/L). The number of tumorspheres was counted after 10-15 days.

Cell cycle and cell synchronization. Cells were synchronized by double-thymidine treatment. Medium was replaced with thymidine-free medium allowing cells to re-enter the cell cycle. After transfection, 100K cells were fixed in cold 70% ethanol, incubated overnight at −20° C., stained using propidium iodide, and subjected to flow cytometry analysis for cell cycle.

SA-β-galactosidase staining. 20K cells were seeded in DMEM complete medium for 5 days and stained with the senescence SA-β-galactosidase staining kit (Cell Signaling) according to the manufacturer's protocol.

Competition mixing assay. Cells co-cultured were seeded at a 1:1 ratio and maintained in DMEM complete medium or low glucose for 7 days. At Day 0 and Day 7, cells were analyzed by flow cytometry for stable expression of GFP or RFP/YFP.

Glucose uptake assay. Cells were seeded in a 6 well plates at a density of 300,000 cells per well in DMEM complete medium. On the next day, the cells were washed twice in PBS and incubated in serum-glucose free medium for 2 hours. The medium was then removed, the cells were incubated for 1 hour in DMEM medium with 1 g/L of glucose. The uptake was determined by using Glucose Assay Kit (Eton Bioscience) according to the manufacturer's protocol.

Lactate production assay. Cells were seeded in a 6 well plates at a density of 300,000 cells per well in DMEM complete medium. On the next day, the cells were washed twice in PBS and incubated in serum-glucose free medium for 2 hours. The medium was then removed, the cells were incubated for 1 hour in DMEM medium with 1 g/L of glucose. The uptake was determined by using L-Lactate assay Kit (Eton Bioscience) according to the manufacturer's protocol.

Reverse transcription quantitative PCR (RT-qPCR). Isolation of total RNA and miRNAs were performed by using RNeasy kit from Qiagen according to the manufacturer's instructions. RNA concentration was determined using a spectrometer. 500 ng of total RNA was used to synthesize cDNA using a TAKARA kit according to manufacturer's protocol. When not available, primer sequences were designed using Invitrogen primer design and primer3 tools, and are summarized in supplementary Table 4. Real-time PCR was performed using SYBR Green reagent and a Bio-Rad system (Applied Biosystems) according the manufacturer's instructions. Efficacy tests have been performed, and all primers have been validated prior utilization. The relative level of each sample was normalized to, at least, two housekeeping genes (EEF1A1, ALAS1, Cyclophilin A and/or Tuba2). RT-PCR reactions were carried out in technical and biological duplicates or triplicates, and the average cycle threshold (CT) values were determined.

GBM subtyping. GSCs gene expression has been assessed by qRT-PCR. All primers are listed in Supplemental Table 4 according to Proneural, Neural, Classical and Mesenchymal subtypes. Genes involved in the glycolytic, Pentose Phosphate Pathway (PPP) and mitochondrial oxidative phosphorylation (OXPHOS) pathways are listed as well.

Immunoblotting. Proteins were extracted in RIPA buffer and quantified using the Pierce BCA kit (Thermo Fisher). 10-30 μg of protein was boiled in NuPage buffer (Thermo Fisher) and loaded onto a denaturing SDS-polyacrylamide gel (10%), transferred to PVDF membranes and blotted with anti-mouse or -rabbit HRP-conjugated secondary antibodies (Bio-Rad). The following antibodies were used for immunoblotting: β3 (Cell Signaling), Glut3 (Santa Cruz Biotechnology), YAP (Santa Cruz) YAP-XP (cell signaling), TAZ (Cell Signaling), PAK4 and pPAK4 (Cell Signaling), and Vinculin and β-actin (Sigma-Aldrich) as loading controls.

Histological analysis (Immunochemistry and Immunofluorescence). For immunohistochemical staining of formalin-fixed paraffin-embedded tissues, antigen retrieval was performed in citrate buffer at pH 6.0 and 95° C. for 20 minutes. Sections were blocked then incubated overnight at 4° C. in primary antibody integrin αvβ3 (LM609) or β3 (Cell signaling), Glut3 (Santa Cruz Biotechnology), GFAP (cell signaling), βIIITubulin (Sigma-Aldrich), Nestin (Fisher Scientific), CD133 (Miltenyi Biotech) followed by biotin-conjugated anti-rabbit IgG and an avidin-biotin peroxidase detection system with 3,3'-diaminobenzidine substrate (Vector) then counterstained with hematoxylin. A Nikon Eclipse C1 Confocal microscope was used for imaging.

In vivo experiments. All experiments were performed according to the protocol S05018 and approved by the UCSD Institutional Animal Care and Use Committee. The number of mice used for each experiment is indicated in the corresponding figures.

Orthotopic brain tumor xenografts. Intracranial transplantation of U87MG or GSC (Ge518 and Ge479) into 6-8-week-old nu/nu nude immunocompromised mice (Charles River Labs) was performed in accordance with the UCSD Institutional Animal Care and Use Committee. U87MG cells bearing β3, Glut3 shRNA or shβ3 ectopically expressing Glut3 as well as shRNA control (15 mice per group) were orthotopically transplanted following washing and resuspension in PBS. Ge479 and Ge518 were orthotopically transplanted following washing and resuspension in DMEM/F12. Mice were treated with vehicle (PBS) or cilengitide (10 mg kg 1 or 30 mg kg 1; 8 mice per group) five days per week. Briefly, with a stereotaxic frame (Stoelting Co.), a small burr hole was made in the skull 2 mm anterior and 2 mm lateral to the bregma. A 31-gauge Hamilton needle/syringe was inserted 3 mm, and 0.25 μl/minute was dispensed ($10^5$ tumor cells in 2 μl media). A total of $1\times10^5$ and $3\times10^5$ cells in 2 μl was injected respectively for U87MG cells and GSCs respectively. Animals were monitored daily and those exhibiting signs of morbidity and/or development of neurological symptoms were euthanized.

Analysis of microarray data. The files for expression analysis were downloaded from GEO with the accession number GSE4412. Only the data obtained with Affymetrix Human Genome U133A Array (GPL96) was used. The sample description files were downloaded from the supplementary material of the article titled "Brain tumor initiating cells adapt to restricted nutrition through preferential glucose uptake". Microarray data was analyzed with R version 3.3.1 software. Differential expression for β3 and Glut3 was performed with the LIMMA™ package (version 3.28.21) and GBM subgroup enrichment calculations were performed using hypergeometric probability distribution (R function dhyper). The enrichment significance values were adjusted using the Benjamini-Hochberg method for each gene independently. Panther analysis was used for graphing differential gene expression analysis (Mi et al., 2016). MEM (Multi Experiment Matrix) was used for correlation between Glut3 and β3 expression (Adler et al., 2009). The StDev threshold for Glut3 was set to 0.29. Distance was measured by both Pearson and Spearman's rank correlation distance, and the betaMEM method was used to determine the P-value. Survexpress was used to generate Kaplan-Meier curves of β3, Glut3, ALDOC, PFKM and TAZ from Freije (GSE4412, GPL96, 85 samples), Lee (GSE13041, GPL96, 218 samples) and The Cancer Genoma Atlas (TCGA) (GBM-LGG and GBM, June 2016, 660 and 518 samples respectively) datasets. TCGA dataset has been harvested for generating the hierarchical cluster for all ITGBs and survival months has been used as censor with Cox survival analysis (Aguirre-Gamboa et al., 2013).

Statistics. All statistical analyses were performed using the Student paired t test. We also performed an analysis of variance applying a bivariate analysis. Significant P-values (p<0.05) is indicated in the text of the results and/or figure legends. Data are representative of results obtained in the indicated number of independent experiments. For in vivo experiments, all statistical analyses were carried out using PRISM™ software (GRAPHPAD™, GraphPad™). Chi-squared tests or t-tests were used to calculate statistical significance.

REFERENCES

Adler, P., et al. (2009). Mining for coexpression across hundreds of datasets using novel rank aggregation and visualization methods. Genome Biol 10, R139.

Aguirre-Gamboa, et al. (2013). SurvExpress: an online biomarker validation tool and database for cancer gene expression data using survival analysis. PLOS ONE 8, e74250.

Birsoy, K., et al. (2014). Metabolic determinants of cancer cell sensitivity to glucose limitation and biguanides. Nature 508, 108-112.

Boado, R. J., et al., (1994). Gene expression of GLUT3 and GLUT1 glucose transporters in human brain tumors. Brain Res Mol Brain Res 27, 51-57.

Brennan, C. W., et al. (2013). The somatic genomic landscape of glioblastoma. Cell 155, 462-477.

Chen, W., et al, (2017). Cyclo (RGD)-Decorated Reduction-Responsive Nanogels Mediate Targeted Chemotherapy of Integrin Overexpressing Human Glioblastoma In Vivo. Small (Weinheim an der Bergstrasse, Germany) 13.

Cheresh, D. A. (1987). Human endothelial cells synthesize and express an Arg-Gly-Asp-directed adhesion receptor involved in attachment to fibrinogen and von Willebrand factor. Proc Natl Acad Sci USA 84, 6471-6475.

Cirkel, G. A., et al. (2016). A dose escalating phase I study of GLPG0187, a broad spectrum integrin receptor antagonist, in adult patients with progressive high-grade glioma and other advanced solid malignancies. Investigational new drugs 34, 184-192.

Cosset, E., et al. (2016). Human tissue engineering allows the identification of active miRNA regulators of glioblastoma aggressiveness. Biomaterials 107, 74-87.

Desgrosellier, J. S., and Cheresh, D. A. (2010). Integrins in cancer: biological implications and therapeutic opportunities. Nat Rev Cancer 10, 9-22.

Desgrosellier, J. S., et al. (2014). Integrin alphavbeta3 drives slug activation and stemness in the pregnant and neoplastic mammary gland. Dev Cell 30, 295-308.

Fang, Y., Jiang, et al. (2017). Targeted glioma chemotherapy by cyclic RGD peptide-functionalized reversibly core-crosslinked multifunctional poly(ethylene glycol)-b-poly (epsilon-caprolactone) micelles. Acta biomaterialia 50, 396-406.

Flavahan, W. A., et al. (2013). Brain tumor initiating cells adapt to restricted nutrition through preferential glucose uptake. Nat Neurosci 16, 1373-1382.

Franovic, A., et al (2015). Glioblastomas require integrin alphavbeta3/PAK4 signaling to escape senescence. Cancer Res 75, 4466-4473.

Freije, W. A., et al (2004). Gene expression profiling of gliomas strongly predicts survival. Cancer Res 64, 6503-6510.

Gladson, C. L., et al. (1991). Glioblastoma expression of vitronectin and the alpha v beta 3 integrin. Adhesion mechanism for transformed glial cells. J Clin Invest 88, 1924-1932.

He, S., et al. (2017). A tumor-targeting cRGD-EGFR siRNA conjugate and its anti-tumor effect on glioblastoma in vitro and in vivo. Drug delivery 24, 471-481.

Jin, Z. H., et al. (2017). 67Cu-Radiolabeling of a multimeric RGD peptide for alpha Vbeta3 integrin-targeted radionuclide therapy: stability, therapeutic efficacy, and safety studies in mice. Nuclear medicine communications 38, 347-355.

Lathia, J. D., et al. (2015). Cancer stem cells in glioblastoma. Genes Dev 29, 1203-1217.

Mason, W. P. (2015). End of the road: confounding results of the CORE trial terminate the arduous journey of cilengitide for glioblastoma. Neuro-oncology 17, 634-635.

Mi, H., et al. (2016). PANTHER version 10: expanded protein families and functions, and analysis tools. Nucleic Acids Research 44, D336-D342.

Moroishi, T., Hansen, C. G., and Guan, K.-L. (2015). The emerging roles of YAP and TAZ in cancer. Nat Rev Cancer 15, 73-79.

Nabors, L. B., et al. (2007). Phase I and correlative biology study of cilengitide in patients with recurrent malignant glioma. J Clin Oncol 25, 1651-1657.

Noushmehr, H., et al. (2010). Identification of a CpG island methylator phenotype that defines a distinct subgroup of glioma. Cancer Cell 17, 510-522.

Nutt, C. L., et al. (2003). Gene expression-based classification of malignant gliomas correlates better with survival than histological classification. Cancer Res 63, 1602-1607.

Paolillo, M., Serra, M., and Schinelli, S. (2016). Integrins in glioblastoma: Still an attractive target? Pharmacol Res 113, 55-61.

Patronas, N. J., et al. (1985). Prediction of survival in glioma patients by means of positron emission tomography. J Neurosurg 62, 816-822.

Phillips, H. S., et al. (2006). Molecular subclasses of high-grade glioma predict prognosis, delineate a pattern of disease progression, and resemble stages in neurogenesis. Cancer Cell 9, 157-173.

Reardon, D. A., et al. (2008). Randomized phase II study of cilengitide, an integrin-targeting arginine-glycine-aspartic acid peptide, in recurrent glioblastoma multiforme. J Clin Oncol 26, 5610-5617.

Seguin, L., et al. (2014). An integrin beta (3)-KRAS-RalB complex drives tumour stemness and resistance to EGFR inhibition. Nat Cell Biol 16, 457-468.

Stupp, R., et al. (2014). Cilengitide combined with standard treatment for patients with newly diagnosed glioblastoma with methylated MGMT promoter (CENTRIC EORTC 26071-22072 study). The lancet oncology 15, 1100-1108.

Stupp, R., et al. (2005). Radiotherapy plus Concomitant and Adjuvant Temozolomide for Glioblastoma. New England Journal of Medicine 352, 987-996.

Verhaak, R. G., et al. (2010). Integrated genomic analysis identifies clinically relevant subtypes of glioblastoma characterized by abnormalities in PDGFRA, IDH1, EGFR, and NF1. Cancer Cell 17, 98-110.

Wang, W., et al. (2015). AMPK modulates Hippo pathway activity to regulate energy homeostasis. Nat Cell Biol 17, 490-499.

Weis, S. M., and Cheresh, D. A. (2011). Tumor angiogenesis: molecular pathways and therapeutic targets. Nature Medicine 17, 1359-1370.

Weller, M., et al. (2016). Cilengitide in newly diagnosed glioblastoma: biomarker expression and outcome. Oncotarget advance online.

A number of exemplary embodiments have been described. Nevertheless, it will be understood that various modifications may be made without departing from the spirit and scope of the invention. Accordingly, other embodiments are within the scope of the following claims.

---

What is claimed is:

1. A method for treating or ameliorating, or killing, or inducing into senescence, a tumor or a cancer cell in an individual in need thereof, the method comprising:

(a) selecting an individual in need thereof who will be sensitive to a treatment inhibiting the integrin avb3 (αvβ3) pathway using a method comprising:

(i) selecting an individual having a tumor or a cancer cell that expresses both avb3+ and Glut3+, and (ii) from individuals selected in step (a) (i), further selecting an individual having a tumor or cancer cell that is Glut-3 addicted, wherein a tumor or a cancer cell is Glut-3 addicted if the tumor or the cancer cell expresses an mRNA or a protein marker consistent with a Classical or Proneural subtype, wherein the mRNA or a protein marker consistent with a Classical or Proneural subtype comprises an EGFR, GLI1, NES, DLL3 or OLIG2 gene transcript or an EGFR, GLI1, NES, DLL3 or OLIG2 protein; and (b) administering to the selected individual from step (a) (ii) a treatment inhibiting the αvβ3 pathway.

2. The method of claim 1, wherein the treatment inhibits avb3, Glut3, PAK4, or YAP/TAZ.

3. The method of claim 1, wherein the treatment comprises administering to the individual in need thereof cilengitide (or, 2-[(2S,5R,8S,115)-5-benzyl-11-{3-[(diaminomethylidene)amino]propyl}-7-methyl-3,6,9,12,15-pentaoxo-8-(propan-2-yl)-1,4,7,10,13-pentaazacyclopentadecan-2-yl] acetic acid).

4. The method of claim 1, wherein the tumor or cancer cell is a glioblastoma (GBM) tumor or a GBM cancer cell.

5. The method of claim 1, wherein the tumor or cancer cell is a melanoma or a primitive neuroectodermal tumor (PNET).

6. The method of claim 1, wherein determining if the tumor or the cancer cell expresses both avb3+ and Glut3+ is by a method comprising using an antibody that specifically binds to a protein of the integrin avb3 pathway.

7. The method of claim 6, wherein the antibody that specifically binds to a protein of the integrin avb3 pathway comprises: an avb3, Glut3, PAK4, or YAP/TAZ binding antibody.

8. A method for treating or ameliorating, or killing, or inducing into senescence, a melanoma or a primitive neuroectodermal tumor (PNET) in an individual in need thereof, the method comprising:

(a) selecting an individual in need thereof who will be sensitive to a treatment inhibiting the integrin avb3 (αvβ3) pathway using a method comprising:

(i) selecting an individual having a melanoma or a PNET that expresses both avb3+ and Glut3+, and (ii) from individuals selected in step (i), further selecting an individual having a melanoma or a PNET that is Glut-3 addicted; and (b) administering to the selected individual from step (a)
(ii) a treatment inhibiting the αvβ3 pathway.

9. The method of claim 8, wherein the melanoma or the PNET is Glut-3 addicted if:

(1) the melanoma or the PNET expresses an mRNA or a protein marker consistent with a Classical or Proneural subtype, wherein the mRNA or a protein marker consistent with a Classical or Proneural subtype comprises an EGFR, GLI1, NES, DLL3 or OLIG2 gene transcript or an EGFR, GLI1, NES, DLL3 or OLIG2 protein, or (2) the melanoma or the PNET expresses an mRNA or a protein consistent with a Glut3 addicted gene signature.

\* \* \* \* \*

SEQUENCE LISTING

```
Sequence total quantity: 151
SEQ ID NO: 1              moltype = DNA  length = 20
FEATURE                   Location/Qualifiers
misc_feature              1..20
                          note = Synthetic: Cyclo FWD
source                    1..20
                          mol_type = other DNA
                          organism = synthetic construct
SEQUENCE: 1
caggtcctgg catcttgtcc                                              20

SEQ ID NO: 2              moltype = DNA  length = 20
FEATURE                   Location/Qualifiers
misc_feature              1..20
                          note = Synthetic: Cyclo REV
source                    1..20
                          mol_type = other DNA
                          organism = synthetic construct
SEQUENCE: 2
ttgctggtct tgccattcct                                              20

SEQ ID NO: 3              moltype = DNA  length = 19
FEATURE                   Location/Qualifiers
misc_feature              1..19
                          note = Synthetic: Tuba2 FWD
source                    1..19
                          mol_type = other DNA
                          organism = synthetic construct
SEQUENCE: 3
aggagctggc aagcatgtg                                               19

SEQ ID NO: 4              moltype = DNA  length = 19
FEATURE                   Location/Qualifiers
misc_feature              1..19
                          note = Synthetic: Tuba2 REV
source                    1..19
                          mol_type = other DNA
                          organism = synthetic construct
SEQUENCE: 4
cggtgcgaac ttcatcgat                                               19

SEQ ID NO: 5              moltype = DNA  length = 20
FEATURE                   Location/Qualifiers
misc_feature              1..20
```

```
                              note = Synthetic: ALAS1 FWD
source                        1..20
                              mol_type = other DNA
                              organism = synthetic construct
SEQUENCE: 5
ctcaccacac accccagatg                                                        20

SEQ ID NO: 6         moltype = DNA   length = 19
FEATURE              Location/Qualifiers
misc_feature         1..19
                     note = Synthetic: ALAS1 REV
source               1..19
                     mol_type = other DNA
                     organism = synthetic construct
SEQUENCE: 6
agttccagcc ccacttgct                                                         19

SEQ ID NO: 7         moltype = DNA   length = 21
FEATURE              Location/Qualifiers
misc_feature         1..21
                     note = Synthetic: EEF1A1 FWD
source               1..21
                     mol_type = other DNA
                     organism = synthetic construct
SEQUENCE: 7
agcaaaaatg acccaccaat g                                                      21

SEQ ID NO: 8         moltype = DNA   length = 20
FEATURE              Location/Qualifiers
misc_feature         1..20
                     note = Synthetic: EEF1A1 REV
source               1..20
                     mol_type = other DNA
                     organism = synthetic construct
SEQUENCE: 8
ggcctggatg gttcaggata                                                        20

SEQ ID NO: 9         moltype = DNA   length = 24
FEATURE              Location/Qualifiers
misc_feature         1..24
                     note = Synthetic: SLC2A1 FWD
source               1..24
                     mol_type = other DNA
                     organism = synthetic construct
SEQUENCE: 9
tatcgtcaac acggccttca ctgt                                                   24

SEQ ID NO: 10        moltype = DNA   length = 24
FEATURE              Location/Qualifiers
misc_feature         1..24
                     note = Synthetic: SLC2A1 REV
source               1..24
                     mol_type = other DNA
                     organism = synthetic construct
SEQUENCE: 10
aacagctcct cgggtgtctt atca                                                   24

SEQ ID NO: 11        moltype = DNA   length = 24
FEATURE              Location/Qualifiers
misc_feature         1..24
                     note = Synthetic: SLC2A2 FWD
source               1..24
                     mol_type = other DNA
                     organism = synthetic construct
SEQUENCE: 11
caaccattgg agttggcgct gtaa                                                   24

SEQ ID NO: 12        moltype = DNA   length = 24
FEATURE              Location/Qualifiers
misc_feature         1..24
                     note = Synthetic: SLC2A2 REV
source               1..24
                     mol_type = other DNA
                     organism = synthetic construct
SEQUENCE: 12
aggtccacag aagtccgcaa tgta                                                   24

SEQ ID NO: 13        moltype = DNA   length = 20
FEATURE              Location/Qualifiers
```

-continued

```
misc_feature          1..20
                      note = Synthetic: SLC2A3 FWD
source                1..20
                      mol_type = other DNA
                      organism = synthetic construct
SEQUENCE: 13
tccacgctca tgactgtttc                                                    20

SEQ ID NO: 14         moltype = DNA  length = 20
FEATURE               Location/Qualifiers
misc_feature          1..20
                      note = Synthetic: SLC2A3 REV
source                1..20
                      mol_type = other DNA
                      organism = synthetic construct
SEQUENCE: 14
gcctggtcca atttcaaaga                                                    20

SEQ ID NO: 15         moltype = DNA  length = 19
FEATURE               Location/Qualifiers
misc_feature          1..19
                      note = Synthetic: SLC2A6 FWD
source                1..19
                      mol_type = other DNA
                      organism = synthetic construct
SEQUENCE: 15
cggaagctga gcatcatgt                                                     19

SEQ ID NO: 16         moltype = DNA  length = 21
FEATURE               Location/Qualifiers
misc_feature          1..21
                      note = Synthetic: SLC2A6 REV
source                1..21
                      mol_type = other DNA
                      organism = synthetic construct
SEQUENCE: 16
gggagcaatc tcagacacgt a                                                  21

SEQ ID NO: 17         moltype = DNA  length = 21
FEATURE               Location/Qualifiers
misc_feature          1..21
                      note = Synthetic: ITGB3 FWD
source                1..21
                      mol_type = other DNA
                      organism = synthetic construct
SEQUENCE: 17
gtgacctgaa ggagaatctg c                                                  21

SEQ ID NO: 18         moltype = DNA  length = 21
FEATURE               Location/Qualifiers
misc_feature          1..21
                      note = Synthetic: ITGB3 REV
source                1..21
                      mol_type = other DNA
                      organism = synthetic construct
SEQUENCE: 18
tcactcactg ggaactcgat g                                                  21

SEQ ID NO: 19         moltype = DNA  length = 20
FEATURE               Location/Qualifiers
misc_feature          1..20
                      note = Synthetic: CD133 FWD
source                1..20
                      mol_type = other DNA
                      organism = synthetic construct
SEQUENCE: 19
actcccataa agctggaccc                                                    20

SEQ ID NO: 20         moltype = DNA  length = 23
FEATURE               Location/Qualifiers
misc_feature          1..23
                      note = Synthetic:
source                1..23
                      mol_type = other DNA
                      organism = synthetic construct
SEQUENCE: 20
tcaattttgg attcatatgc ctt                                                23

SEQ ID NO: 21         moltype = DNA  length = 22
```

-continued

```
FEATURE                Location/Qualifiers
misc_feature           1..22
                       note = Synthetic: Oct4 FWD
source                 1..22
                       mol_type = other DNA
                       organism = synthetic construct
SEQUENCE: 21
tctcccatgc attcaaactg ag                                        22

SEQ ID NO: 22          moltype = DNA   length = 22
FEATURE                Location/Qualifiers
misc_feature           1..22
                       note = Synthetic: Oct4 REV
source                 1..22
                       mol_type = other DNA
                       organism = synthetic construct
SEQUENCE: 22
cctttgtgtt cccaattcct tc                                        22

SEQ ID NO: 23          moltype = DNA   length = 22
FEATURE                Location/Qualifiers
misc_feature           1..22
                       note = Synthetic: Nanog FWD
source                 1..22
                       mol_type = other DNA
                       organism = synthetic construct
SEQUENCE: 23
tctcccatgc attcaaactg ag                                        22

SEQ ID NO: 24          moltype = DNA   length = 22
FEATURE                Location/Qualifiers
misc_feature           1..22
                       note = Synthetic: Nanog REV
source                 1..22
                       mol_type = other DNA
                       organism = synthetic construct
SEQUENCE: 24
cccacttctg cagagaatag tg                                        22

SEQ ID NO: 25          moltype = DNA   length = 20
FEATURE                Location/Qualifiers
misc_feature           1..20
                       note = Synthetic: GFAP FWD
source                 1..20
                       mol_type = other DNA
                       organism = synthetic construct
SEQUENCE: 25
aagagatccg cacgcagtat                                           20

SEQ ID NO: 26          moltype = DNA   length = 20
FEATURE                Location/Qualifiers
misc_feature           1..20
                       note = Synthetic: GFAP REV
source                 1..20
                       mol_type = other DNA
                       organism = synthetic construct
SEQUENCE: 26
aggtcaagga ctgcaactgg                                           20

SEQ ID NO: 27          moltype = DNA   length = 20
FEATURE                Location/Qualifiers
misc_feature           1..20
                       note = Synthetic: Tubb3 FWD
source                 1..20
                       mol_type = other DNA
                       organism = synthetic construct
SEQUENCE: 27
cggtggtgga accctacaac                                           20

SEQ ID NO: 28          moltype = DNA   length = 19
FEATURE                Location/Qualifiers
misc_feature           1..19
                       note = Synthetic: Tubb3 REV
source                 1..19
                       mol_type = other DNA
                       organism = synthetic construct
SEQUENCE: 28
aggtggtgac tccgctcat                                            19
```

-continued

```
SEQ ID NO: 29           moltype = DNA   length = 22
FEATURE                 Location/Qualifiers
misc_feature            1..22
                        note = Synthetic: hYAP FWD
source                  1..22
                        mol_type = other DNA
                        organism = synthetic construct
SEQUENCE: 29
ccaaggcttg accctcgttt tg                                        22

SEQ ID NO: 30           moltype = DNA   length = 22
FEATURE                 Location/Qualifiers
misc_feature            1..22
                        note = Synthetic: hYAP REV
source                  1..22
                        mol_type = other DNA
                        organism = synthetic construct
SEQUENCE: 30
tcgcatctgt tgctgctggt tg                                        22

SEQ ID NO: 31           moltype = DNA   length = 22
FEATURE                 Location/Qualifiers
misc_feature            1..22
                        note = Synthetic: hTAZ FWD
source                  1..22
                        mol_type = other DNA
                        organism = synthetic construct
SEQUENCE: 31
tcaccaacac cagcagcaga tg                                        22

SEQ ID NO: 32           moltype = DNA   length = 23
FEATURE                 Location/Qualifiers
misc_feature            1..23
                        note = Synthetic: hTAZ REV
source                  1..23
                        mol_type = other DNA
                        organism = synthetic construct
SEQUENCE: 32
gcattctctg aagccgcagt ttc                                       23

SEQ ID NO: 33           moltype = DNA   length = 19
FEATURE                 Location/Qualifiers
misc_feature            1..19
                        note = Synthetic: PISD FWD
source                  1..19
                        mol_type = other DNA
                        organism = synthetic construct
SEQUENCE: 33
ccaccgactg gactgtgtc                                            19

SEQ ID NO: 34           moltype = DNA   length = 20
FEATURE                 Location/Qualifiers
misc_feature            1..20
                        note = Synthetic: PISD REV
source                  1..20
                        mol_type = other DNA
                        organism = synthetic construct
SEQUENCE: 34
ccgctcgtta tggcagaaga                                           20

SEQ ID NO: 35           moltype = DNA   length = 20
FEATURE                 Location/Qualifiers
misc_feature            1..20
                        note = Synthetic: PISD REV
source                  1..20
                        mol_type = other DNA
                        organism = synthetic construct
SEQUENCE: 35
ccgatgggct aatcacgctg                                           20

SEQ ID NO: 36           moltype = DNA   length = 20
FEATURE                 Location/Qualifiers
misc_feature            1..20
                        note = Synthetic: ACAD9 FWD
source                  1..20
                        mol_type = other DNA
                        organism = synthetic construct
SEQUENCE: 36
agttcttggg acccgtggaa                                           20
```

```
SEQ ID NO: 37          moltype = DNA   length = 23
FEATURE                Location/Qualifiers
misc_feature           1..23
                       note = Synthetic: ACAD9 REV
source                 1..23
                       mol_type = other DNA
                       organism = synthetic construct
SEQUENCE: 37
gtcttgagta catggtgttg gag                                        23

SEQ ID NO: 38          moltype = DNA   length = 21
FEATURE                Location/Qualifiers
misc_feature           1..21
                       note = Synthetic: HK3 FWD
source                 1..21
                       mol_type = other DNA
                       organism = synthetic construct
SEQUENCE: 38
ggacaggagc accctcattt c                                          21

SEQ ID NO: 39          moltype = DNA   length = 21
FEATURE                Location/Qualifiers
misc_feature           1..21
                       note = Synthetic: HK3 REV
source                 1..21
                       mol_type = other DNA
                       organism = synthetic construct
SEQUENCE: 39
cctccgaatg gcatctctca g                                          21

SEQ ID NO: 40          moltype = DNA   length = 20
FEATURE                Location/Qualifiers
misc_feature           1..20
                       note = Synthetic: HK2 FWD
source                 1..20
                       mol_type = other DNA
                       organism = synthetic construct
SEQUENCE: 40
gagccaccac tcaccctact                                            20

SEQ ID NO: 41          moltype = DNA   length = 19
FEATURE                Location/Qualifiers
misc_feature           1..19
                       note = Synthetic: HK2 REV
source                 1..19
                       mol_type = other DNA
                       organism = synthetic construct
SEQUENCE: 41
ccaggcattc ggcaatgtg                                             19

SEQ ID NO: 42          moltype = DNA   length = 23
FEATURE                Location/Qualifiers
misc_feature           1..23
                       note = Synthetic: HK1 FWD
source                 1..23
                       mol_type = other DNA
                       organism = synthetic construct
SEQUENCE: 42
gctctccgat gaaactctca tag                                        23

SEQ ID NO: 43          moltype = DNA   length = 21
FEATURE                Location/Qualifiers
misc_feature           1..21
                       note = Synthetic: HK1 REV
source                 1..21
                       mol_type = other DNA
                       organism = synthetic construct
SEQUENCE: 43
ggaccttacg aatgttggca a                                          21

SEQ ID NO: 44          moltype = DNA   length = 21
FEATURE                Location/Qualifiers
misc_feature           1..21
                       note = Synthetic: GPI FWD
source                 1..21
                       mol_type = other DNA
                       organism = synthetic construct
SEQUENCE: 44
```

-continued

```
caaggaccgc ttcaaccact t                                                21

SEQ ID NO: 45          moltype = DNA   length = 21
FEATURE                Location/Qualifiers
misc_feature           1..21
                       note = Synthetic: GPI REV
source                 1..21
                       mol_type = other DNA
                       organism = synthetic construct
SEQUENCE: 45
ccaggatggg tgtgtttgac c                                                21

SEQ ID NO: 46          moltype = DNA   length = 19
FEATURE                Location/Qualifiers
misc_feature           1..19
                       note = Synthetic: ALDOC FWD
source                 1..19
                       mol_type = other DNA
                       organism = synthetic construct
SEQUENCE: 46
atgcctcact cgtacccag                                                   19

SEQ ID NO: 47          moltype = DNA   length = 21
FEATURE                Location/Qualifiers
misc_feature           1..21
                       note = Synthetic: ALDOC REV
source                 1..21
                       mol_type = other DNA
                       organism = synthetic construct
SEQUENCE: 47
tttccacccc aatttggctc a                                                21

SEQ ID NO: 48          moltype = DNA   length = 20
FEATURE                Location/Qualifiers
misc_feature           1..20
                       note = Synthetic: PFKP FWD
source                 1..20
                       mol_type = other DNA
                       organism = synthetic construct
SEQUENCE: 48
gcatgggtat ctacgtgggg                                                  20

SEQ ID NO: 49          moltype = DNA   length = 20
FEATURE                Location/Qualifiers
misc_feature           1..20
                       note = Synthetic: PFKP REV
source                 1..20
                       mol_type = other DNA
                       organism = synthetic construct
SEQUENCE: 49
ctctgcgatg tttgagcctc                                                  20

SEQ ID NO: 50          moltype = DNA   length = 19
FEATURE                Location/Qualifiers
misc_feature           1..19
                       note = Synthetic: TPI1 FWD
source                 1..19
                       mol_type = other DNA
                       organism = synthetic construct
SEQUENCE: 50
ctcatcggca ctctgaacg                                                   19

SEQ ID NO: 51          moltype = DNA   length = 23
FEATURE                Location/Qualifiers
misc_feature           1..23
                       note = Synthetic: TPI1 REV
source                 1..23
                       mol_type = other DNA
                       organism = synthetic construct
SEQUENCE: 51
gcgaagtcga tataggcagt agg                                              23

SEQ ID NO: 52          moltype = DNA   length = 22
FEATURE                Location/Qualifiers
misc_feature           1..22
                       note = Synthetic: Gapdh FWD
source                 1..22
                       mol_type = other DNA
                       organism = synthetic construct
```

-continued

```
SEQUENCE: 52
gcacaagagg aagagagaga cc                                              22

SEQ ID NO: 53          moltype = DNA  length = 20
FEATURE                Location/Qualifiers
misc_feature           1..20
                       note = Synthetic: Gapdh REV
source                 1..20
                       mol_type = other DNA
                       organism = synthetic construct
SEQUENCE: 53
aggggagatt cagtgtggtg                                                 20

SEQ ID NO: 54          moltype = DNA  length = 21
FEATURE                Location/Qualifiers
misc_feature           1..21
                       note = Synthetic: PGK1 FWD
source                 1..21
                       mol_type = other DNA
                       organism = synthetic construct
SEQUENCE: 54
gaacaaggtt aaagccgagc c                                               21

SEQ ID NO: 55          moltype = DNA  length = 21
FEATURE                Location/Qualifiers
misc_feature           1..21
                       note = Synthetic: PGK1 REV
source                 1..21
                       mol_type = other DNA
                       organism = synthetic construct
SEQUENCE: 55
gtggcagatt gactcctacc a                                               21

SEQ ID NO: 56          moltype = DNA  length = 21
FEATURE                Location/Qualifiers
misc_feature           1..21
                       note = Synthetic: PKM2 FWD
source                 1..21
                       mol_type = other DNA
                       organism = synthetic construct
SEQUENCE: 56
atgtcgaagc cccatagtga a                                               21

SEQ ID NO: 57          moltype = DNA  length = 21
FEATURE                Location/Qualifiers
misc_feature           1..21
                       note = Synthetic: PKM2 REV
source                 1..21
                       mol_type = other DNA
                       organism = synthetic construct
SEQUENCE: 57
tgggtggtga atcaatgtcc a                                               21

SEQ ID NO: 58          moltype = DNA  length = 20
FEATURE                Location/Qualifiers
misc_feature           1..20
                       note = Synthetic: ENO1 FWD
source                 1..20
                       mol_type = other DNA
                       organism = synthetic construct
SEQUENCE: 58
gccgtgaacg agaagtcctg                                                 20

SEQ ID NO: 59          moltype = DNA  length = 19
FEATURE                Location/Qualifiers
misc_feature           1..19
                       note = Synthetic: ENO1 REV
source                 1..19
                       mol_type = other DNA
                       organism = synthetic construct
SEQUENCE: 59
acgcctgaag agactcggt                                                  19

SEQ ID NO: 60          moltype = DNA  length = 21
FEATURE                Location/Qualifiers
misc_feature           1..21
                       note = Synthetic: ALDOA FWD
source                 1..21
                       mol_type = other DNA
```

```
                        organism = synthetic construct
SEQUENCE: 60
atgccctacc aatatccagc a                                            21

SEQ ID NO: 61          moltype = DNA  length = 20
FEATURE                Location/Qualifiers
misc_feature           1..20
                       note = Synthetic: ALDOA REV
source                 1..20
                       mol_type = other DNA
                       organism = synthetic construct
SEQUENCE: 61
gctcccagtg gactcatctg                                             20

SEQ ID NO: 62          moltype = DNA  length = 19
FEATURE                Location/Qualifiers
misc_feature           1..19
                       note = Synthetic: G6PD FWD
source                 1..19
                       mol_type = other DNA
                       organism = synthetic construct
SEQUENCE: 62
cgaggccgtc accaagaac                                              19

SEQ ID NO: 63          moltype = DNA  length = 20
FEATURE                Location/Qualifiers
misc_feature           1..20
                       note = Synthetic: G6PD REV
source                 1..20
                       mol_type = other DNA
                       organism = synthetic construct
SEQUENCE: 63
gtagtggtcg atgcggtaga                                             20

SEQ ID NO: 64          moltype = DNA  length = 20
FEATURE                Location/Qualifiers
misc_feature           1..20
                       note = Synthetic: PGLS FWD
source                 1..20
                       mol_type = other DNA
                       organism = synthetic construct
SEQUENCE: 64
ggagcctcgt ctcgatgcta                                             20

SEQ ID NO: 65          moltype = DNA  length = 19
FEATURE                Location/Qualifiers
misc_feature           1..19
                       note = Synthetic: PGLS REV
source                 1..19
                       mol_type = other DNA
                       organism = synthetic construct
SEQUENCE: 65
gagagaagat gcgtccggt                                              19

SEQ ID NO: 66          moltype = DNA  length = 19
FEATURE                Location/Qualifiers
misc_feature           1..19
                       note = Synthetic: PDG FWD
source                 1..19
                       mol_type = other DNA
                       organism = synthetic construct
SEQUENCE: 66
atggcccaag ctgacatcg                                              19

SEQ ID NO: 67          moltype = DNA  length = 21
FEATURE                Location/Qualifiers
misc_feature           1..21
                       note = Synthetic: PGD REV
source                 1..21
                       mol_type = other DNA
                       organism = synthetic construct
SEQUENCE: 67
aaagccgtgg tcattcatgt t                                           21

SEQ ID NO: 68          moltype = DNA  length = 20
FEATURE                Location/Qualifiers
misc_feature           1..20
                       note = Synthetic: TKT FWD
source                 1..20
```

```
                        mol_type = other DNA
                        organism = synthetic construct
SEQUENCE: 68
tccacaccat gcgctacaag                                                       20

SEQ ID NO: 69           moltype = DNA   length = 21
FEATURE                 Location/Qualifiers
misc_feature            1..21
                        note = Synthetic: TKT REV
source                  1..21
                        mol_type = other DNA
                        organism = synthetic construct
SEQUENCE: 69
caagtcggag ctgatcttcc t                                                     21

SEQ ID NO: 70           moltype = DNA   length = 19
FEATURE                 Location/Qualifiers
misc_feature            1..19
                        note = Synthetic: TALDO1 FWD
source                  1..19
                        mol_type = other DNA
                        organism = synthetic construct
SEQUENCE: 70
ctcacccgtg aagcgtcag                                                        19

SEQ ID NO: 71           moltype = DNA   length = 20
FEATURE                 Location/Qualifiers
misc_feature            1..20
                        note = Synthetic: TALDO1 REV
source                  1..20
                        mol_type = other DNA
                        organism = synthetic construct
SEQUENCE: 71
gttggtggta gcatcctggg                                                       20

SEQ ID NO: 72           moltype = DNA   length = 21
FEATURE                 Location/Qualifiers
misc_feature            1..21
                        note = Synthetic: SYT1 FWD
source                  1..21
                        mol_type = other DNA
                        organism = synthetic construct
SEQUENCE: 72
gtgagcgaga gtcaccatga g                                                     21

SEQ ID NO: 73           moltype = DNA   length = 19
FEATURE                 Location/Qualifiers
misc_feature            1..19
                        note = Synthetic: SYT1 REV
source                  1..19
                        mol_type = other DNA
                        organism = synthetic construct
SEQUENCE: 73
cccacggtgg caatggaat                                                        19

SEQ ID NO: 74           moltype = DNA   length = 21
FEATURE                 Location/Qualifiers
misc_feature            1..21
                        note = Synthetic: SYT5 FWD
source                  1..21
                        mol_type = other DNA
                        organism = synthetic construct
SEQUENCE: 74
agacgctgaa ccctcacttt g                                                     21

SEQ ID NO: 75           moltype = DNA   length = 19
FEATURE                 Location/Qualifiers
misc_feature            1..19
                        note = Synthetic: SYT5 REV
source                  1..19
                        mol_type = other DNA
                        organism = synthetic construct
SEQUENCE: 75
cgaagtcgta caccgccat                                                        19

SEQ ID NO: 76           moltype = DNA   length = 20
FEATURE                 Location/Qualifiers
misc_feature            1..20
                        note = Synthetic: SLC12A5 FWD
```

-continued

```
source                    1..20
                          mol_type = other DNA
                          organism = synthetic construct
SEQUENCE: 76
tgctcctgta cgatgctcac                                              20

SEQ ID NO: 77             moltype = DNA   length = 19
FEATURE                   Location/Qualifiers
misc_feature              1..19
                          note = Synthetic: SLC12A5 REV
source                    1..19
                          mol_type = other DNA
                          organism = synthetic construct
SEQUENCE: 77
gctcctgcaa aggtagtgc                                               19

SEQ ID NO: 78             moltype = DNA   length = 21
FEATURE                   Location/Qualifiers
misc_feature              1..21
                          note = Synthetic: PACSIN1 FWD
source                    1..21
                          mol_type = other DNA
                          organism = synthetic construct
SEQUENCE: 78
gaacagcaag acggagcaat c                                            21

SEQ ID NO: 79             moltype = DNA   length = 20
FEATURE                   Location/Qualifiers
misc_feature              1..20
                          note = Synthetic: PACSIN1 REV
source                    1..20
                          mol_type = other DNA
                          organism = synthetic construct
SEQUENCE: 79
gaccagccgc ttttcctcaa                                              20

SEQ ID NO: 80             moltype = DNA   length = 20
FEATURE                   Location/Qualifiers
misc_feature              1..20
                          note = Synthetic: RGS4 FWD
source                    1..20
                          mol_type = other DNA
                          organism = synthetic construct
SEQUENCE: 80
acatcggcta ggtttcctgc                                              20

SEQ ID NO: 81             moltype = DNA   length = 23
FEATURE                   Location/Qualifiers
misc_feature              1..23
                          note = Synthetic: RGS4 REV
source                    1..23
                          mol_type = other DNA
                          organism = synthetic construct
SEQUENCE: 81
gttgtgggaa gaattgtgtt cac                                          23

SEQ ID NO: 82             moltype = DNA   length = 21
FEATURE                   Location/Qualifiers
misc_feature              1..21
                          note = Synthetic: MAL2 FWD
source                    1..21
                          mol_type = other DNA
                          organism = synthetic construct
SEQUENCE: 82
gtccgtgaca gcgtttttct t                                            21

SEQ ID NO: 83             moltype = DNA   length = 23
FEATURE                   Location/Qualifiers
misc_feature              1..23
                          note = Synthetic: MAL2 REV
source                    1..23
                          mol_type = other DNA
                          organism = synthetic construct
SEQUENCE: 83
aattgaggct gctacgttta tgt                                          23

SEQ ID NO: 84             moltype = DNA   length = 20
FEATURE                   Location/Qualifiers
misc_feature              1..20
```

```
                        note = Synthetic: DLL3 FWD
source                  1..20
                        mol_type = other DNA
                        organism = synthetic construct
SEQUENCE: 84
cactcccgga tgcactcaac                                              20

SEQ ID NO: 85           moltype = DNA   length = 21
FEATURE                 Location/Qualifiers
misc_feature            1..21
                        note = Synthetic: DLL3 REV
source                  1..21
                        mol_type = other DNA
                        organism = synthetic construct
SEQUENCE: 85
gattccaatc tacggacgag c                                            21

SEQ ID NO: 86           moltype = DNA   length = 20
FEATURE                 Location/Qualifiers
misc_feature            1..20
                        note = Synthetic: DCX FWD
source                  1..20
                        mol_type = other DNA
                        organism = synthetic construct
SEQUENCE: 86
gacagcccac tcttttgagc                                              20

SEQ ID NO: 87           moltype = DNA   length = 20
FEATURE                 Location/Qualifiers
misc_feature            1..20
                        note = Synthetic: DCX REV
source                  1..20
                        mol_type = other DNA
                        organism = synthetic construct
SEQUENCE: 87
tgggtttccc ttcatgactc                                              20

SEQ ID NO: 88           moltype = DNA   length = 20
FEATURE                 Location/Qualifiers
misc_feature            1..20
                        note = Synthetic: OLIG2 FWD
source                  1..20
                        mol_type = other DNA
                        organism = synthetic construct
SEQUENCE: 88
cagaagcgct gatggtcata                                              20

SEQ ID NO: 89           moltype = DNA   length = 20
FEATURE                 Location/Qualifiers
misc_feature            1..20
                        note = Synthetic: OLIG2 REV
source                  1..20
                        mol_type = other DNA
                        organism = synthetic construct
SEQUENCE: 89
tcggcagttt tgggttattc                                              20

SEQ ID NO: 90           moltype = DNA   length = 21
FEATURE                 Location/Qualifiers
misc_feature            1..21
                        note = Synthetic: ERBB3 FWD
source                  1..21
                        mol_type = other DNA
                        organism = synthetic construct
SEQUENCE: 90
ggtgatgggg aaccttgaga t                                            21

SEQ ID NO: 91           moltype = DNA   length = 22
FEATURE                 Location/Qualifiers
misc_feature            1..22
                        note = Synthetic: ERBB3 REV
source                  1..22
                        mol_type = other DNA
                        organism = synthetic construct
SEQUENCE: 91
ctgtcacttc tcgaatccac tg                                           22

SEQ ID NO: 92           moltype = DNA   length = 21
FEATURE                 Location/Qualifiers
```

```
misc_feature          1..21
                      note = Synthetic: PDGFRA FWD
source                1..21
                      mol_type = other DNA
                      organism = synthetic construct
SEQUENCE: 92
tggcagtacc ccatgtctga a                                          21

SEQ ID NO: 93         moltype = DNA  length = 21
FEATURE               Location/Qualifiers
misc_feature          1..21
                      note = Synthetic: PDGFRA REV
source                1..21
                      mol_type = other DNA
                      organism = synthetic construct
SEQUENCE: 93
ccaagaccgt cacaaaaagg c                                          21

SEQ ID NO: 94         moltype = DNA  length = 23
FEATURE               Location/Qualifiers
misc_feature          1..23
                      note = Synthetic: P2RX7 FWD
source                1..23
                      mol_type = other DNA
                      organism = synthetic construct
SEQUENCE: 94
tatgagacga acaaagtcac tcg                                        23

SEQ ID NO: 95         moltype = DNA  length = 23
FEATURE               Location/Qualifiers
misc_feature          1..23
                      note = Synthetic: P2RX7 REV
source                1..23
                      mol_type = other DNA
                      organism = synthetic construct
SEQUENCE: 95
gcaaagcaaa cgtaggaaaa gat                                        23

SEQ ID NO: 96         moltype = DNA  length = 21
FEATURE               Location/Qualifiers
misc_feature          1..21
                      note = Synthetic: BMP2 FWD
source                1..21
                      mol_type = other DNA
                      organism = synthetic construct
SEQUENCE: 96
actaccagaa acgagtggga a                                          21

SEQ ID NO: 97         moltype = DNA  length = 21
FEATURE               Location/Qualifiers
misc_feature          1..21
                      note = Synthetic: BMP2 REV
source                1..21
                      mol_type = other DNA
                      organism = synthetic construct
SEQUENCE: 97
gcatctgttc tcggaaaacc t                                          21

SEQ ID NO: 98         moltype = DNA  length = 26
FEATURE               Location/Qualifiers
misc_feature          1..26
                      note = Synthetic: SOX2-FWD
source                1..26
                      mol_type = other DNA
                      organism = synthetic construct
SEQUENCE: 98
gggaaatggg aggggtgcaa aagagg                                     26

SEQ ID NO: 99         moltype = DNA  length = 26
FEATURE               Location/Qualifiers
misc_feature          1..26
                      note = Synthetic: SOX-2-REV
source                1..26
                      mol_type = other DNA
                      organism = synthetic construct
SEQUENCE: 99
ttgcgtgagt gtggatggga ttggtg                                     26

SEQ ID NO: 100        moltype = DNA  length = 20
```

```
FEATURE              Location/Qualifiers
misc_feature         1..20
                     note = Synthetic: CD44 FWD
source               1..20
                     mol_type = other DNA
                     organism = synthetic construct
SEQUENCE: 100
aaggtggagc aaacacaacc                                             20

SEQ ID NO: 101       moltype = DNA   length = 20
FEATURE              Location/Qualifiers
misc_feature         1..20
                     note = Synthetic: CD44 REV
source               1..20
                     mol_type = other DNA
                     organism = synthetic construct
SEQUENCE: 101
agctttttct tctgcccaca                                             20

SEQ ID NO: 102       moltype = DNA   length = 20
FEATURE              Location/Qualifiers
misc_feature         1..20
                     note = Synthetic: YKL40 FWD
source               1..20
                     mol_type = other DNA
                     organism = synthetic construct
SEQUENCE: 102
tcaagaacag gaaccccaac                                             20

SEQ ID NO: 103       moltype = DNA   length = 20
FEATURE              Location/Qualifiers
misc_feature         1..20
                     note = Synthetic: YKL40 REV
source               1..20
                     mol_type = other DNA
                     organism = synthetic construct
SEQUENCE: 103
aaattcggcc ttcatttcct                                             20

SEQ ID NO: 104       moltype = DNA   length = 17
FEATURE              Location/Qualifiers
misc_feature         1..17
                     note = Synthetic: MET FWD
source               1..17
                     mol_type = other DNA
                     organism = synthetic construct
SEQUENCE: 104
ccccaccctt tgttcag                                                17

SEQ ID NO: 105       moltype = DNA   length = 17
FEATURE              Location/Qualifiers
misc_feature         1..17
                     note = Synthetic: MET REV
source               1..17
                     mol_type = other DNA
                     organism = synthetic construct
SEQUENCE: 105
tcagccttgt ccctcct                                                17

SEQ ID NO: 106       moltype = DNA   length = 20
FEATURE              Location/Qualifiers
misc_feature         1..20
                     note = Synthetic: RelB FWD
source               1..20
                     mol_type = other DNA
                     organism = synthetic construct
SEQUENCE: 106
tgaatgtggt gaggatctgc                                             20

SEQ ID NO: 107       moltype = DNA   length = 20
FEATURE              Location/Qualifiers
misc_feature         1..20
                     note = Synthetic: RelB REV
source               1..20
                     mol_type = other DNA
                     organism = synthetic construct
SEQUENCE: 107
cgcagctctg atgtgtttgt                                             20
```

-continued

```
SEQ ID NO: 108          moltype = DNA   length = 21
FEATURE                 Location/Qualifiers
misc_feature            1..21
                        note = Synthetic: LGALS3 FWD
source                  1..21
                        mol_type = other DNA
                        organism = synthetic construct
SEQUENCE: 108
gtgaagccca atgcaaacag a                                        21

SEQ ID NO: 109          moltype = DNA   length = 21
FEATURE                 Location/Qualifiers
misc_feature            1..21
                        note = Synthetic: LGALS3 REV
source                  1..21
                        mol_type = other DNA
                        organism = synthetic construct
SEQUENCE: 109
agcgtgggtt aaagtggaag g                                        21

SEQ ID NO: 110          moltype = DNA   length = 21
FEATURE                 Location/Qualifiers
misc_feature            1..21
                        note = Synthetic: LOX FWD
source                  1..21
                        mol_type = other DNA
                        organism = synthetic construct
SEQUENCE: 110
cctactacat ccaggcgtcc a                                        21

SEQ ID NO: 111          moltype = DNA   length = 25
FEATURE                 Location/Qualifiers
misc_feature            1..25
                        note = Synthetic: LOX REV
source                  1..25
                        mol_type = other DNA
                        organism = synthetic construct
SEQUENCE: 111
cataatctct gacatctgcc cctgt                                    25

SEQ ID NO: 112          moltype = DNA   length = 22
FEATURE                 Location/Qualifiers
misc_feature            1..22
                        note = Synthetic: THBS1 FWD
source                  1..22
                        mol_type = other DNA
                        organism = synthetic construct
SEQUENCE: 112
tgctatcaca acggagttca gt                                       22

SEQ ID NO: 113          moltype = DNA   length = 22
FEATURE                 Location/Qualifiers
misc_feature            1..22
                        note = Synthetic: THBS1 REV
source                  1..22
                        mol_type = other DNA
                        organism = synthetic construct
SEQUENCE: 113
gcaggacacc tttttgcaga tg                                       22

SEQ ID NO: 114          moltype = DNA   length = 20
FEATURE                 Location/Qualifiers
misc_feature            1..20
                        note = Synthetic: LAMB1 FWD
source                  1..20
                        mol_type = other DNA
                        organism = synthetic construct
SEQUENCE: 114
cacaagcccg aaccctactg                                          20

SEQ ID NO: 115          moltype = DNA   length = 23
FEATURE                 Location/Qualifiers
misc_feature            1..23
                        note = Synthetic: LAMB1 REV
source                  1..23
                        mol_type = other DNA
                        organism = synthetic construct
SEQUENCE: 115
gaccacattt tcaatgagat ggc                                      23
```

```
SEQ ID NO: 116          moltype = DNA   length = 23
FEATURE                 Location/Qualifiers
misc_feature            1..23
                        note = Synthetic: DAB2 FWD
source                  1..23
                        mol_type = other DNA
                        organism = synthetic construct
SEQUENCE: 116
gtagaaacaa gtgcaaccaa tgg                                        23

SEQ ID NO: 117          moltype = DNA   length = 22
FEATURE                 Location/Qualifiers
misc_feature            1..22
                        note = Synthetic: DAB2 REV
source                  1..22
                        mol_type = other DNA
                        organism = synthetic construct
SEQUENCE: 117
gcctttgaac cttgctaaga ga                                         22

SEQ ID NO: 118          moltype = DNA   length = 21
FEATURE                 Location/Qualifiers
misc_feature            1..21
                        note = Synthetic: S100A4 FWD
source                  1..21
                        mol_type = other DNA
                        organism = synthetic construct
SEQUENCE: 118
gatgagcaac ttggacagca a                                          21

SEQ ID NO: 119          moltype = DNA   length = 21
FEATURE                 Location/Qualifiers
misc_feature            1..21
                        note = Synthetic: S100A4 REV
source                  1..21
                        mol_type = other DNA
                        organism = synthetic construct
SEQUENCE: 119
ctgggctgct tatctgggaa g                                          21

SEQ ID NO: 120          moltype = DNA   length = 20
FEATURE                 Location/Qualifiers
misc_feature            1..20
                        note = Synthetic: COL1A2 FWD
source                  1..20
                        mol_type = other DNA
                        organism = synthetic construct
SEQUENCE: 120
gagcggtaac aagggtgagc                                            20

SEQ ID NO: 121          moltype = DNA   length = 20
FEATURE                 Location/Qualifiers
misc_feature            1..20
                        note = Synthetic: COL1A2 REV
source                  1..20
                        mol_type = other DNA
                        organism = synthetic construct
SEQUENCE: 121
cttccccatt agggcctctc                                            20

SEQ ID NO: 122          moltype = DNA   length = 22
FEATURE                 Location/Qualifiers
misc_feature            1..22
                        note = Synthetic: MMP9 FWD
source                  1..22
                        mol_type = other DNA
                        organism = synthetic construct
SEQUENCE: 122
tgtaccgcta tggttacact cg                                         22

SEQ ID NO: 123          moltype = DNA   length = 19
FEATURE                 Location/Qualifiers
misc_feature            1..19
                        note = Synthetic: MMP9 REV
source                  1..19
                        mol_type = other DNA
                        organism = synthetic construct
SEQUENCE: 123
```

-continued

```
ggcagggaca gttgcttct                                                    19

SEQ ID NO: 124        moltype = DNA   length = 21
FEATURE               Location/Qualifiers
misc_feature          1..21
                      note = Synthetic: VEGFA FWD
source                1..21
                      mol_type = other DNA
                      organism = synthetic construct
SEQUENCE: 124
agggcagaat catcacgaag t                                                  21

SEQ ID NO: 125        moltype = DNA   length = 20
FEATURE               Location/Qualifiers
misc_feature          1..20
                      note = Synthetic: VEGFA REV
source                1..20
                      mol_type = other DNA
                      organism = synthetic construct
SEQUENCE: 125
agggtctcga ttggatggca                                                    20

SEQ ID NO: 126        moltype = DNA   length = 21
FEATURE               Location/Qualifiers
misc_feature          1..21
                      note = Synthetic: IGFBP2 FWD
source                1..21
                      mol_type = other DNA
                      organism = synthetic construct
SEQUENCE: 126
gacaatggcg atgaccactc a                                                  21

SEQ ID NO: 127        moltype = DNA   length = 21
FEATURE               Location/Qualifiers
misc_feature          1..21
                      note = Synthetic: IGFBP2 REV
source                1..21
                      mol_type = other DNA
                      organism = synthetic construct
SEQUENCE: 127
cagctccttc atacccgact t                                                  21

SEQ ID NO: 128        moltype = DNA   length = 21
FEATURE               Location/Qualifiers
misc_feature          1..21
                      note = Synthetic: Gli2 FWD
source                1..21
                      mol_type = other DNA
                      organism = synthetic construct
SEQUENCE: 128
ctgcctccga gaagcaagaa g                                                  21

SEQ ID NO: 129        moltype = DNA   length = 20
FEATURE               Location/Qualifiers
misc_feature          1..20
                      note = Synthetic: Gli2 REV
source                1..20
                      mol_type = other DNA
                      organism = synthetic construct
SEQUENCE: 129
gcatggaatg gtggcaagag                                                    20

SEQ ID NO: 130        moltype = DNA   length = 20
FEATURE               Location/Qualifiers
misc_feature          1..20
                      note = Synthetic: EGFR FWD
source                1..20
                      mol_type = other DNA
                      organism = synthetic construct
SEQUENCE: 130
cagcgctacc ttgtcattca                                                    20

SEQ ID NO: 131        moltype = DNA   length = 20
FEATURE               Location/Qualifiers
misc_feature          1..20
                      note = Synthetic: EGFR REV
source                1..20
                      mol_type = other DNA
                      organism = synthetic construct
```

```
SEQUENCE: 131
agctttgcag cccatttcta                                                    20

SEQ ID NO: 132       moltype = DNA   length = 21
FEATURE              Location/Qualifiers
misc_feature         1..21
                     note = Synthetic: ACSBG1 FWD
source               1..21
                     mol_type = other DNA
                     organism = synthetic construct
SEQUENCE: 132
acactgtgca tcggatgttc t                                                  21

SEQ ID NO: 133       moltype = DNA   length = 21
FEATURE              Location/Qualifiers
misc_feature         1..21
                     note = Synthetic: ACSBG1 REV
source               1..21
                     mol_type = other DNA
                     organism = synthetic construct
SEQUENCE: 133
aggagatgtg ttcccacttg t                                                  21

SEQ ID NO: 134       moltype = DNA   length = 19
FEATURE              Location/Qualifiers
misc_feature         1..19
                     note = Synthetic: IGF2 FWD
source               1..19
                     mol_type = other DNA
                     organism = synthetic construct
SEQUENCE: 134
gtggcatcgt tgaggagtg                                                     19

SEQ ID NO: 135       moltype = DNA   length = 19
FEATURE              Location/Qualifiers
misc_feature         1..19
                     note = Synthetic: IGF2 REV
source               1..19
                     mol_type = other DNA
                     organism = synthetic construct
SEQUENCE: 135
cacgtccctc tcggacttg                                                     19

SEQ ID NO: 136       moltype = DNA   length = 20
FEATURE              Location/Qualifiers
misc_feature         1..20
                     note = Synthetic: Nestin FWD
source               1..20
                     mol_type = other DNA
                     organism = synthetic construct
SEQUENCE: 136
ggaagagaac ctgggaaagg                                                    20

SEQ ID NO: 137       moltype = DNA   length = 20
FEATURE              Location/Qualifiers
misc_feature         1..20
                     note = Synthetic: Nestin REV
source               1..20
                     mol_type = other DNA
                     organism = synthetic construct
SEQUENCE: 137
cttggtcctt ctccaccgta                                                    20

SEQ ID NO: 138       moltype = DNA   length = 19
FEATURE              Location/Qualifiers
misc_feature         1..19
                     note = Synthetic: shh FWD
source               1..19
                     mol_type = other DNA
                     organism = synthetic construct
SEQUENCE: 138
ctcgctgctg gtatgctcg                                                     19

SEQ ID NO: 139       moltype = DNA   length = 21
FEATURE              Location/Qualifiers
misc_feature         1..21
                     note = Synthetic: shh REV
source               1..21
                     mol_type = other DNA
```

-continued

```
                            organism = synthetic construct
SEQUENCE: 139
atcgctcgga gtttctggag a                                              21

SEQ ID NO: 140            moltype = DNA   length = 21
FEATURE                   Location/Qualifiers
misc_feature              1..21
                          note = Synthetic: Notch3 FWD
source                    1..21
                          mol_type = other DNA
                          organism = synthetic construct
SEQUENCE: 140
cgtggcttct ttctactgtg c                                              21

SEQ ID NO: 141            moltype = DNA   length = 21
FEATURE                   Location/Qualifiers
misc_feature              1..21
                          note = Synthetic: Notch3 REV
source                    1..21
                          mol_type = other DNA
                          organism = synthetic construct
SEQUENCE: 141
cgttcaccgg atttgtgtca c                                              21

SEQ ID NO: 142            moltype = DNA   length = 19
FEATURE                   Location/Qualifiers
misc_feature              1..19
                          note = Synthetic: GAS1 FWD
source                    1..19
                          mol_type = other DNA
                          organism = synthetic construct
SEQUENCE: 142
atgccgcacc gtcattgag                                                 19

SEQ ID NO: 143            moltype = DNA   length = 21
FEATURE                   Location/Qualifiers
misc_feature              1..21
                          note = Synthetic: GAS1 REV
source                    1..21
                          mol_type = other DNA
                          organism = synthetic construct
SEQUENCE: 143
tcatcgtagt agtcgtccag g                                              21

SEQ ID NO: 144            moltype = DNA   length = 21
FEATURE                   Location/Qualifiers
misc_feature              1..21
                          note = Synthetic: MCM2 FWD
source                    1..21
                          mol_type = other DNA
                          organism = synthetic construct
SEQUENCE: 144
ccgtgacctt ccaccatttg a                                              21

SEQ ID NO: 145            moltype = DNA   length = 21
FEATURE                   Location/Qualifiers
misc_feature              1..21
                          note = Synthetic: MCM2 REV
source                    1..21
                          mol_type = other DNA
                          organism = synthetic construct
SEQUENCE: 145
ggtagtccct ttccatgcca t                                              21

SEQ ID NO: 146            moltype = DNA   length = 20
FEATURE                   Location/Qualifiers
misc_feature              1..20
                          note = Synthetic: CENPF FWD
source                    1..20
                          mol_type = other DNA
                          organism = synthetic construct
SEQUENCE: 146
ctctcccgtc aacagcgttc                                                20

SEQ ID NO: 147            moltype = DNA   length = 22
FEATURE                   Location/Qualifiers
misc_feature              1..22
                          note = Synthetic: CENPF REV
source                    1..22
```

-continued

```
                        mol_type = other DNA
                        organism = synthetic construct
SEQUENCE: 147
gttgtgcata ttcttggctt gc                                    22

SEQ ID NO: 148         moltype = DNA  length = 22
FEATURE                Location/Qualifiers
misc_feature           1..22
                        note = Synthetic: TOP2A FWD
source                 1..22
                        mol_type = other DNA
                        organism = synthetic construct
SEQUENCE: 148
ttaatgctgc ggacaacaaa ca                                    22

SEQ ID NO: 149         moltype = DNA  length = 22
FEATURE                Location/Qualifiers
misc_feature           1..22
                        note = Synthetic: TOP2A REV
source                 1..22
                        mol_type = other DNA
                        organism = synthetic construct
SEQUENCE: 149
cgaccacctg tcactttctt tt                                    22

SEQ ID NO: 150         moltype = DNA  length = 21
FEATURE                Location/Qualifiers
misc_feature           1..21
                        note = Synthetic: KCNF1 FWD
source                 1..21
                        mol_type = other DNA
                        organism = synthetic construct
SEQUENCE: 150
gccagcgacg acatagagat a                                     21

SEQ ID NO: 151         moltype = DNA  length = 20
FEATURE                Location/Qualifiers
misc_feature           1..20
                        note = Synthetic: KCNF1 REV
source                 1..20
                        mol_type = other DNA
                        organism = synthetic construct
SEQUENCE: 151
ccagccaagc agttgatgag                                       20
```